US012702715B2

(12) United States Patent
Disney

(10) Patent No.: US 12,702,715 B2
(45) Date of Patent: Aug. 11, 2026

(54) TARGETED RNA DEGRADATION ALLOWS PRECISION REPURPOSING OF PROTEIN-TARGETED SMALL MOLECULE MEDICINES TO RNA

(71) Applicant: University of Florida Research Foundation, Incorporated, Gainesville, FL (US)

(72) Inventor: Matthew D. Disney, Jupiter, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 763 days.

(21) Appl. No.: 18/018,856

(22) PCT Filed: Jul. 30, 2021

(86) PCT No.: PCT/US2021/043937

§ 371 (c)(1),
(2) Date: Jan. 30, 2023

(87) PCT Pub. No.: WO2022/026851

PCT Pub. Date: Feb. 3, 2022

(65) Prior Publication Data

US 2023/0302139 A1 Sep. 28, 2023

Related U.S. Application Data

(60) Provisional application No. 62/706,108, filed on Jul. 31, 2020.

(51) Int. Cl.
*A61K 47/54* (2017.01)
*A61P 35/00* (2006.01)

(52) U.S. Cl.
CPC ............ *A61K 47/545* (2017.08); *A61P 35/00* (2018.01)

(58) Field of Classification Search
CPC ........ A61K 47/545; A61K 47/55; A61P 35/00
See application file for complete search history.

(56) References Cited

U.S. PATENT DOCUMENTS

| | | | | |
|---|---|---|---|---|
| 9,545,402 | B2 * | 1/2017 | Thakur | A61P 35/02 |
| 2015/0258216 | A1 * | 9/2015 | Rosin-Arbesfeld | C12N 15/85 536/23.6 |
| 2020/0055917 | A1 | 2/2020 | Corey | |
| 2020/0069720 | A1 * | 3/2020 | Thum | A61P 13/12 |

FOREIGN PATENT DOCUMENTS

| | | | |
|---|---|---|---|
| WO | 2012/001074 | A2 | 1/2012 |
| WO | WO 2024/097855 | A2 | 5/2024 |

OTHER PUBLICATIONS

Ding, et al., Bioconjugate Chemistry, v.10, pp. 395-400; 1999. (Year: 1999).*

Wikipedia: https://en.wikipedia.org/wiki/Streptavidin; accessed Oct. 2, 2025 (Year: 2025).*

Wilber, et al.; Biomolecular Engineering, v16, pp. 113-118; 1999. (Year: 1999).*

International Search Report and Written Opinion for App. No. PCT/US2021/043937 mailed Dec. 2, 2021.

Zhang et al., Reprogramming of Protein-Targeted Small-Molecule Medicines to RNA by Ribonuclease Recruitment. J Am Chem Soc. Aug. 25, 2021;143(33):13044-13055. doi: 10.1021/jacs.1c02248. Epub Aug. 13, 2021.

Bartel, MicroRNAs: genomics, biogenesis, mechanism, and function. Cell. Jan. 23, 2004;116(2):281-97. doi: 10.1016/s0092-8674(04)00045-5.

Bartel, MicroRNAs: target recognition and regulatory functions. Cell. Jan. 23, 2009;136(2):215-33. doi: 10.1016/j.cell.2009.01.002.

Bose et al., Selective inhibition of miR-21 by phage display screened peptide. Nucleic Acids Res. Apr. 30, 2015;43(8):4342-52. doi: 10.1093/nar/gkv185. Epub Mar. 30, 2015.

Chakrabarti et al., New insights into the role of RNase L in innate immunity. J Interferon Cytokine Res. Jan. 2011;31(1):49-57. doi: 10.1089/jir.2010.0120. Epub Dec. 29, 2010.

Choi et al., Phase II Study of Dovitinib in Patients with Castration-Resistant Prostate Cancer (KCSG-GU11-05). Cancer Res Treat. Oct. 2018;50(4):1252-1259. doi: 10.4143/crt.2017.438. Epub Jan. 2, 2018.

Cosgrove et al., Collagen COL4A3 knockout: a mouse model for autosomal Alport syndrome. Genes Dev. Dec. 1, 1996;10(23):2981-92. doi: 10.1101/gad.10.23.2981.

Costales et al., Small Molecule Targeted Recruitment of a Nuclease to RNA. J Am Chem Soc. Jun. 6, 2018;140(22):6741-6744. doi: 10.1021/jacs.8b01233. Epub May 24, 2018. Author manuscript, 8 pages.

Costales et al., Small-molecule targeted recruitment of a nuclease to cleave an oncogenic RNA in a mouse model of metastatic cancer. Proc Natl Acad Sci U S A. Feb. 4, 2020;117(5):2406-2411. doi: 10.1073/pnas.1914286117. Epub Jan. 21, 2020. Erratum in: Proc Natl Acad Sci U S A. May 3, 2022;119(18):e2204149119. doi: 10.1073/pnas.2204149119.

Costales et al., Targeted Degradation of a Hypoxia-Associated Non-coding RNA Enhances the Selectivity of a Small Molecule Interacting with RNA. Cell Chem Biol. Aug. 15, 2019;26(8):1180-1186.e5. doi: 10.1016/j.chembiol.2019.04.008. Epub May 23, 2019.

Crews, Feeding the machine: mechanisms of proteasome-catalyzed degradation of ubiquitinated proteins. Curr Opin Chem Biol. Oct. 2003;7(5):534-9. doi: 10.1016/j.cbpa.2003.08.002.

Disney et al., Two-dimensional combinatorial screening identifies specific aminoglycoside-RNA internal loop partners. J Am Chem Soc. Aug. 20, 2008;130(33):11185-94. doi: 10.1021/ja803234t. Epub Jul. 25, 2008.

(Continued)

*Primary Examiner* — Jeffrey S Lundgren
*Assistant Examiner* — W. Justin Youngblood
(74) *Attorney, Agent, or Firm* — Wolf, Greenfield & Sacks, P.C.

(57) ABSTRACT

The protein targeted medicine, Dovitinib, has been repurposed to target a non-coding RNA by using selection and computational drug design via Inforna. Selectivity was achieved for pre-miR-21 by endowing the medicine with the ability to recruit RNA quality control enzymes to cleave the target.

22 Claims, 51 Drawing Sheets

Specification includes a Sequence Listing.

(56) References Cited

OTHER PUBLICATIONS

Esquela-Kerscher et al., Oncomirs—microRNAs with a role in cancer. Nat Rev Cancer. Apr. 2006;6(4):259-69. doi: 10.1038/nrc1840.
Gomez et al., Anti-microRNA-21 oligonucleotides prevent Alport nephropathy progression by stimulating metabolic pathways. J Clin Invest. Jan. 2015; 125(1):141-56. doi: 10.1172/JCI75852. Epub Nov. 21, 2014.
Hampf et al., A protocol for combined Photinus and Renilla luciferase quantification compatible with protein assays. Anal Biochem. Sep. 1, 2006;356(1):94-9. doi: 10.1016/j.ab.2006.04.046. Epub May 12, 2006.
Han et al., Innate immune messenger 2-5A tethers human RNase L into active high-order complexes. Cell Rep. Oct. 25, 2012;2(4):902-13. doi: 10.1016/j.celrep.2012.09.004. Epub Oct. 19, 2012.
Hudson et al., Alport's syndrome, Goodpasture's syndrome, and type IV collagen. N Engl J Med. Jun. 19, 2003;348(25):2543-56. doi: 10.1056/NEJMra022296.
Janes et al., The ReFRAME library as a comprehensive drug repurposing library and its application to the treatment of cryptosporidiosis. Proc Natl Acad Sci U S A. Oct. 16, 2018;115(42):10750-10755. doi: 10.1073/pnas.1810137115. Epub Oct. 3, 2018.
Krichevsky et al., miR-21: a small multi-faceted RNA. J Cell Mol Med. Jan. 2009;13(1):39-53. doi: 10.1111/j.1582-4934.2008.00556.x.
Liu et al., Analysis of secondary structural elements in human microRNA hairpin precursors. BMC Bioinformatics. Mar. 1, 2016;17:112. doi: 10.1186/s12859-016-0960-6.
Ma et al., Loss of the miR-21 allele elevates the expression of its target genes and reduces tumorigenesis. Proc Natl Acad Sci U S A. Jun. 21, 2011;108(25):10144-9. doi: 10.1073/pnas.1103735108. Epub Jun. 6, 2011.
Medina et al., OncomiR addiction in an in vivo model of microRNA-21-induced pre-B-cell lymphoma. Nature. Sep. 2, 2010;467(7311):86-90. doi: 10.1038/nature09284. Epub Aug. 8, 2010.
Mortison et al., Tetracyclines Modify Translation by Targeting Key Human IRNA Substructures. Cell Chem Biol. Dec. 20, 2018;25(12):1506-1518.e13. doi: 10.1016/j.chembiol.2018.09.010. Epub Oct. 11, 2018.
Ozawa et al., The role of CH/x interactions in the high affinity binding of streptavidin and biotin. J Mol Graph Model. Aug. 2017;75:117-124. doi: 10.1016/j.jmgm.2017.05.002. Epub May 5, 2017.
Parker et al., Ligand and Target Discovery by Fragment-Based Screening in Human Cells. Cell. Jan. 26, 2017;168(3):527-541.e29. doi: 10.1016/j.cell.2016.12.029. Epub Jan. 19, 2017.
Pushpakom et al., Drug repurposing: progress, challenges and recommendations. Nat Rev Drug Discov. Jan. 2019;18(1):41-58. doi: 10.1038/nrd.2018.168. Epub Oct. 12, 2018.
Renhowe et al., Design, structure-activity relationships and in vivo characterization of 4-amino-3-benzimidazol-2-ylhydroquinolin-2-ones: a novel class of receptor tyrosine kinase inhibitors. J Med Chem. Jan. 22, 2009;52(2):278-92. doi: 10.1021/jm800790t.
Riva et al., Discovery of SARS-CoV-2 antiviral drugs through large-scale compound repurposing. Nature. Oct. 2020;586(7827):113-119. doi: 10.1038/s41586-020-2577-1. Epub Jul. 24, 2020. Erratum in: Nature. Jul. 2024;631(8019):E3. doi: 10.1038/s41586-024-07659-8.
Sakamoto et al., Discovery of peptidic miR-21 processing inhibitor by mirror image phage display: A novel method to generate RNA binding D-peptides. Bioorg Med Chem Lett. Feb. 15, 2017;27(4):826-828. doi: 10.1016/j.bmcl.2017.01.023. Epub Jan. 10, 2017.
Sakamoto et al., Protacs: chimeric molecules that target proteins to the Skp1-Cullin-F box complex for ubiquitination and degradation. Proc Natl Acad Sci U S A. Jul. 17, 2001;98(15):8554-9. doi: 10.1073/pnas.141230798. Epub Jul. 3, 2001.
Shortridge et al., A Macrocyclic Peptide Ligand Binds the Oncogenic MicroRNA-21 Precursor and Suppresses Dicer Processing. ACS Chem Biol. Jun. 16, 2017;12(6):1611-1620. doi: 10.1021/acschembio.7b00180. Epub May 2, 2017. Author manuscript, 24 pages.
Silverman, Viral encounters with 2',5'-oligoadenylate synthetase and RNase L during the interferon antiviral response. J Virol. Dec. 2007;81(23):12720-9. doi: 10.1128/JVI.01471-07. Epub Sep. 5, 2007.
Tran et al., Identifying the preferred RNA motifs and chemotypes that interact by probing millions of combinations. Nat Commun. 2012;3:1125. doi: 10.1038/ncomms2119. Author manuscript, 22 pages.
Trudel et al., CHIR-258, a novel, multitargeted tyrosine kinase inhibitor for the potential treatment of t(4;14) multiple myeloma. Blood. Apr. 1, 2005;105(7):2941-8. doi: 10.1182/blood-2004-10-3913. Epub Dec. 14, 2004.
Velagapudi et al., A cross-linking approach to map small molecule-RNA binding sites in cells. Bioorg Med Chem Lett. Jun. 15, 2019;29(12):1532-1536. doi: 10.1016/j.bmcl.2019.04.001. Epub Apr. 2, 2019. Author manuscript, 9 pages.
Velagapudi et al., Approved Anti-cancer Drugs Target Oncogenic Non-coding RNAs. Cell Chem Biol. Sep. 20, 2018;25(9):1086-1094.e7. doi: 10.1016/j.chembiol.2018.05.015. Epub Jun. 28, 2018.
Velagapudi et al., Defining RNA-Small Molecule Affinity Landscapes Enables Design of a Small Molecule Inhibitor of an Oncogenic Noncoding RNA. ACS Cent Sci. Mar. 2, 20172;3(3):205-216. doi: 10.1021/acscentsci.7b00009. Epub Mar. 6, 2017.
Velagapudi et al., Sequence-based design of bioactive small molecules that target precursor microRNAs. Nat Chem Biol. Apr. 2014;10(4):291-7. doi: 10.1038/nchembio.1452. Epub Feb. 9, 2014. Author manuscript, 23 pages.
Ventura et al., Targeted deletion reveals essential and overlapping functions of the miR-17 through 92 family of miRNA clusters. Cell. Mar. 7, 2008;132(5):875-86. doi: 10.1016/j.cell.2008.02.019.
Wang et al., Mechanistic studies of a small-molecule modulator of SMN2 splicing. Proc Natl Acad Sci U S A. May 15, 2018;115(20):E4604-E4612. doi: 10.1073/pnas.1800260115. Epub Apr. 30, 2018.
Yan et al., Regulating miRNA-21 Biogenesis By Bifunctional Small Molecules. J Am Chem Soc. Apr. 12, 2017;139(14):4987-4990. doi: 10.1021/jacs.7b00610. Epub Mar. 29, 2017. Author manuscript, 11 pages.
Yang et al., Mouse models for tumor metastasis. Methods Mol Biol. 2012;928:221-8. doi: 10.1007/978-1-62703-008-3_17. Author manuscript, 6 pages.
Zhang et al., A Simple Statistical Parameter for Use in Evaluation and Validation of High Throughput Screening Assays. J Biomol Screen. 1999;4(2):67-73. doi: 10.1177/108705719900400206.

* cited by examiner

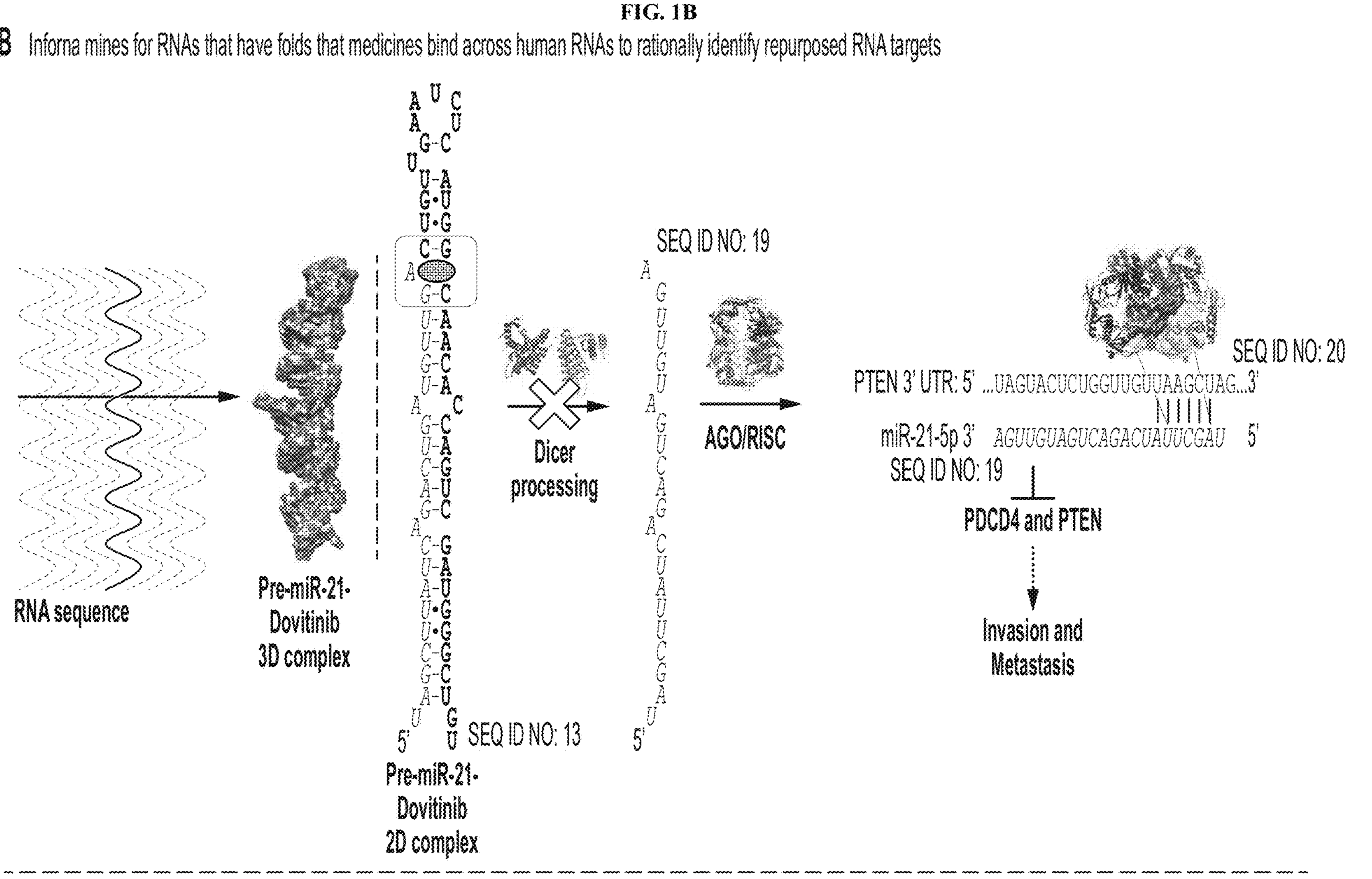
FIG. 1B
B Inforna mines for RNAs that have folds that medicines bind across human RNAs to rationally identify repurposed RNA targets
RNA sequence
Pre-miR-21-
Dovitinib
3D complex
SEQ ID NO: 13
Pre-miR-21-
Dovitinib
2D complex
Dicer
processing
SEQ ID NO: 19
AGO/RISC
SEQ ID NO: 20
PTEN 3' UTR: 5' ...UAGUACUCUGGUUGUUAAGCUAG...3'
miR-21-5p 3' AGUUGUAGUCAGACUAUUCGAU 5'
SEQ ID NO: 19
PDCD4 and PTEN
Invasion and
Metastasis Delparantag Metiazinic
Acid Dovitinib 1

Dovitinib-RIBOTAC 2

Dovitinib-PROTAC 3

Protein
selective
RNA
selective
3
1
Me
2
2500-fold change
in selectivity
$IC_{50}$ (M) for miR-21
functional inhibition
$10^{-5}$
$10^{-6}$
$10^{-7}$
$10^{-8}$
$10^{-7}$
$10^{-6}$
$10^{-5}$
$IC_{50}$ (M) for RTK
functional inhibition Vehicle
1
2
miR-21 FISH
pERK IHC
ERK IHC
500 μm
Normalized miR-21 Intensity
Normalized pERK Intensity
Normalized ERK Intensity
1.0
0.5
*

[1], μM
0 0.2 1 5 20 100 T1 No Dicer Untreated RNA
G28
G25
G21
C23
0 0.2 1 5 20 100 No Dicer T1 HO
U24
Pre-miR-21
Wild Type (WT)
Pre-miR-21 WT
Pre-miR-21 Dicer Site Mutant
Normalized Cleavage
1.0
0.5
0.0
[1], μM 0.2 1 5 20 100
**
***
***
Pre-miR-21
Dicer Site
Base pair Mutant
Pre-miR-21 Wild Type = SEQ ID NO: 13
Pre-miR-21 Dicer Site Base Pair Mutant = SEQ ID NO: 14

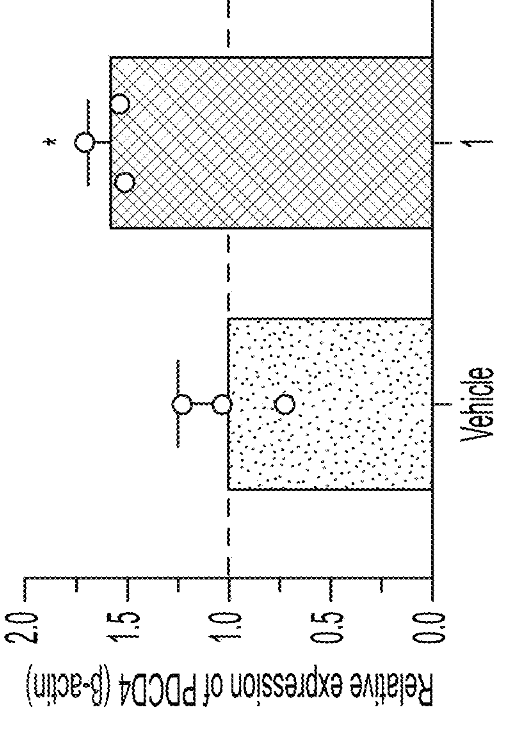
FIG. 11D
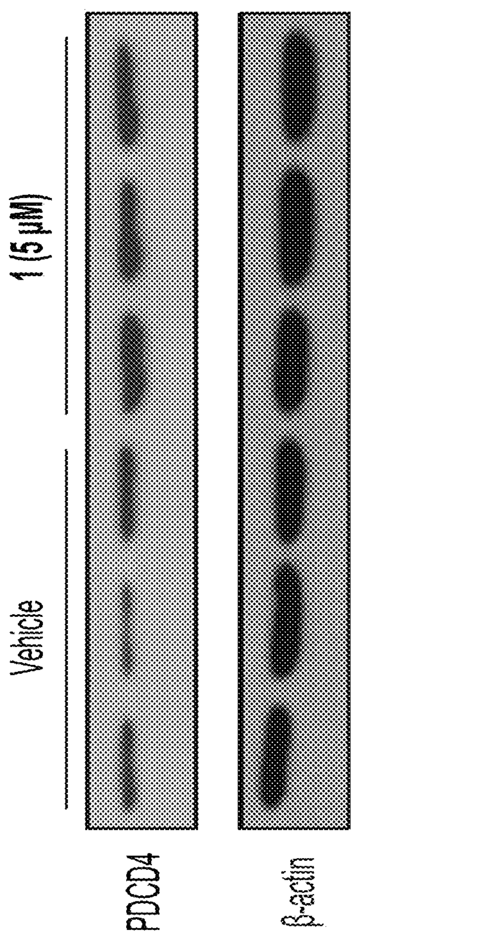

SEQ ID NO: 13

Pre-miR-21
Wild Type

SEQ ID NO: 14

Pre-miR-21 Dicer Site
Base Pair Mutant

Pre-miR-21 Wild Type = SEQ ID NO:13
Pre-miR-21 Dicer Site Base Pair Mutant = SEQ ID NO:14

Vehicle
2'-5'-A4
1 (65 µM)
7 (65 µM)
8
16
33
65
[2], µM
Oligomeric Rnase L
Monomeric Rnase L

[3], μM
0
0.001
0.01
0.1
1
FLT3
β-actin

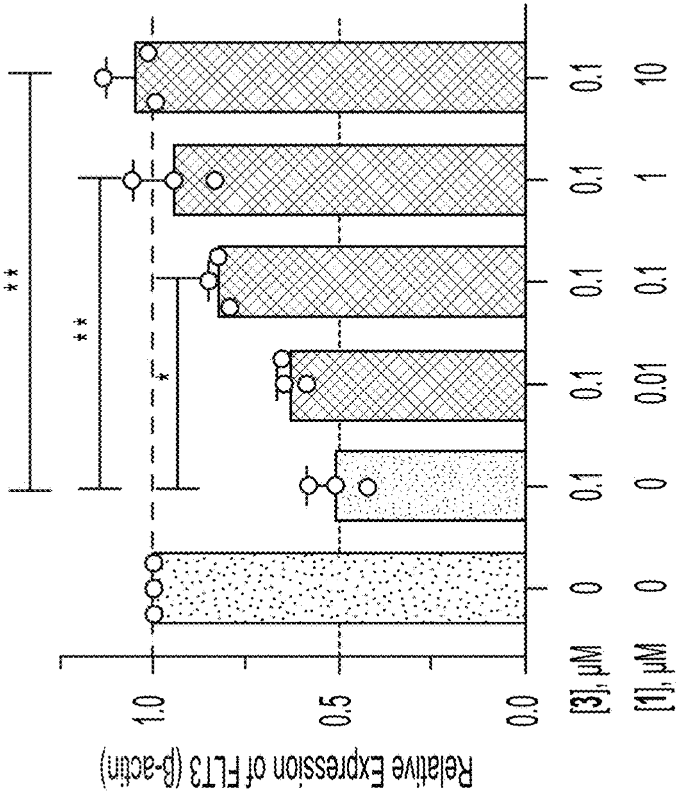
FIG. 16C
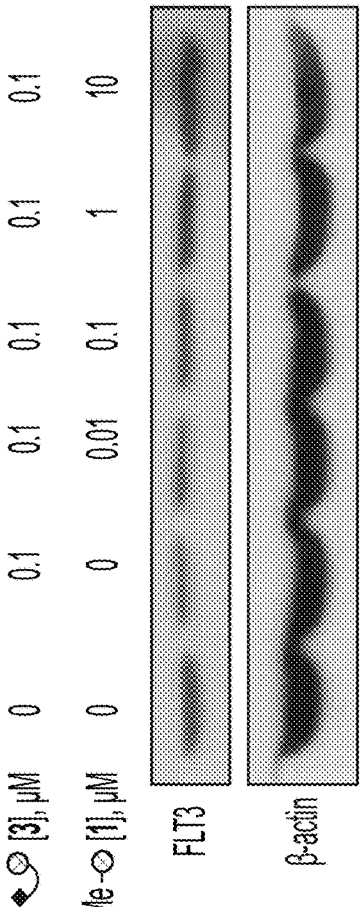

[3], μM 0 0.1 0.1 0.1 0.1 0.1
[2], μM 0 0 0.01 0.1 1 10
FLT3
β-actin

TARGETED RNA DEGRADATION ALLOWS PRECISION REPURPOSING OF PROTEIN-TARGETED SMALL MOLECULE MEDICINES TO RNA

CROSS-REFERENCE TO RELATED APPLICATIONS

This application is a national stage filing under 35 U.S.C. 371 of International Patent Application Serial No. PCT/US2021/043937, filed Jul. 30, 2021, entitled "TARGETED RNA DEGRADATION ALLOWS PRECISION REPURPOSING OF PROTEIN-TARGETED SMALL MOLECULE MEDICINES TO RNA", which claims the benefit of priority to U.S. Provisional Patent Application No. 62/706,108, filed Jul. 31, 2020. The entire contents of these applications are incorporated herein by reference in their entirety.

STATEMENT OF SUPPORT

This invention was made with government support under grant numbers CA249180, NS116846, and NS096898 awarded by the National Institutes of Health. The government has certain rights in the invention.

REFERENCE TO AN ELECTRONIC SEQUENCE LISTING

The contents of the electronic sequence listing (U120270104US01-SUBSEQ-CLL.txt; Size: 4,704 bytes; and Date of Creation: Jan. 22, 2026) are herein incorporated by reference in their entirety.

BACKGROUND

Medicine repurposing accelerates the identification of new applications of known medicines, but a significant concern is more potently modulating the repurposed target over the canonical target[1]. RNA is generally thought to be recalcitrant to small molecule medicines, perhaps because they do not bind avidly. However, repurposing a target from protein attack to upstream RNA attack presents an attractive alternative. The repurposing can be more selective present fewer side effects and involve lower effective dosing than does intercession of messenger proteins such as kinases including but not limited to VEGF, TNF alpha and the like. Therefore, it is an object to repurpose known medicines for RNA targeting.

SUMMARY

These and other objects are accomplished by aspects of the invention directed to RNA targeting of repurposed small molecule medicines. More specifically, aspects of the invention include methods for treatment of disease through use of repurposed small molecule medicines, repurposed small molecules that enable avid binding with RNA and/or RNA interdiction, cleavage and/or amelioration of RNA conversion to micro RNA's controlling cellular messaging and pathways. These methods of treatment comprise interaction of repurposed small molecule medicines with pre-RNA in vitro, in cells and in organisms such as animal models and humans to treat diseases such as cancers associated with certain oncogenic RNAs as well as autoimmune diseases. Embodiments of the repurposed small molecule medicine comprise compounds covalently bound with RNA complexing moieties, nuclease recruitment moieties, nuclease degradation recruiting molecules, and/or RNA covalent binding moieties.

Embodiments of repurposed small molecule medicines include Ribotac and Protac derivatized small molecules. Embodiments of the small molecules functioning as substances for derivatization may have or do have demonstrated capability for strongly interacting with kinases, signaling proteins, cytokines and/or other cellular messaging and transforming systems, for ameliorating the abnormal activity of neoplastic cells and/or immune system cells, more preferably oncogenic cells and oncogenic tissues present in organisms such as animal models and humans. The Ribotac and Protac moieties have the ability to couple the binding properties of the small molecule with simultaneous recruitment of cellular processes for degradation, apoptosis, suppression and/or repression of downstream RNA conversion to miRNA fragments as well as interdiction of intracellular messaging and signaling.

The Ribotac and Protac moieties may be covalently coupled with a small molecule for generation of repurposed medicines. These moieties are essentially flexible polylinking chains having the small molecule at one end and a molecule for recruiting nucleic and/or protein degradation constructs at the other end. The Ribotac moiety carries a nuclease recruiting moiety. nuclease L recruiter, that causes activation of a nuclease enzyme for degradation of RNA. The Protac moiety carries a ubiquitin ligase recruiting moiety for tagging proteins for reassimilation. The primary amine group of Ribotac may be coupled with an installed or existing amine group of the repurposed small molecule through use of a urethane formation agent such as disuccinimidyl carbonate to couple the amines together as a urethane group. The carboxylic acid group of Protac may be coupled with an installed or existing amine group of a repurposed small molecule through use of an amide formation agent such as carbodiimide. The Ribotac moiety has the formula shown below.

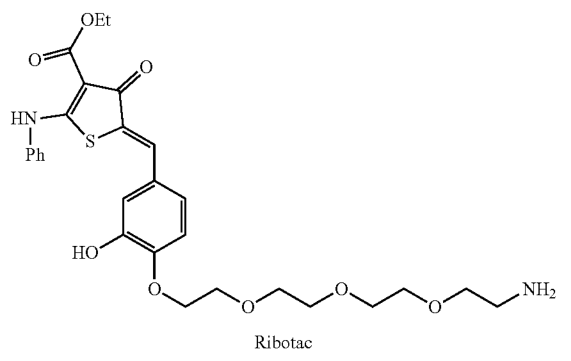 [SMILES: CCOC(=O)C1=C(Nc2ccccc2)S/C(=C\c2ccc(OCCOCCOCCOCCN)c(O)c2)C1=O]

Ribotac

An exemplary small molecule for repurposing as a Ribotac/Protac derivative is Dovitinib, a piperazinyl-dihydrobenzimidazolyl-quinolin-2-one. Dovitinib is a known receptor tyrosine kinase (RTK) inhibitor. Dovitinib binds to and inhibits the phosphorylation of type II-V RTK's such as VEGF, PDGFR, FLT3, c-KIT and CSF-1R. It has antitumor and antiangiogenic activities in vim, see Nat Library of Medicine, PubChem, Dovitinib, Wikipedia (Fibroblast growth factor receptor 1) and Dovitinib Novartis. Dovitinib is currently in human FDA clinical trials sponsored by Oncology Venture.

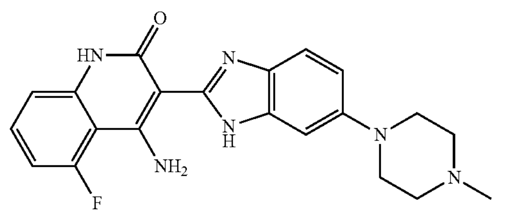

Dovitinib

Specific embodiments of this repurposed small molecule comprise Ribotac-Dovitinib and Protac-Dovitinib, Compounds 2 and 3.

Embodiments of an additional small molecule derivative useful for determining miRNA binding sites is constructed with an amide linker chain carrying alkyne and diazirine groups, hereinafter, ChemCLIP probes. As described above, the small molecule has demonstrated binding capability with ribonucleic acids such as pre-miRNA. Once bound to the ribonucleic acid, the diazirine is irradiated to form a carbene which inserts into a nucleophilic X—H bond such as an amine. The alkyne group is then reacted with a substance such as biotin carrying an azide (—$N_3$) group to form a triazole linkage of the ribonucleic acid, the small molecule and the triazole-biotin. This "pull down" molecule can be immobilized on a streptavidin bead to enable isolation and study. Embodiments of ChemCLIP probes based on Dovitinib have a formula of Compound 4 shown below.

Compound 2

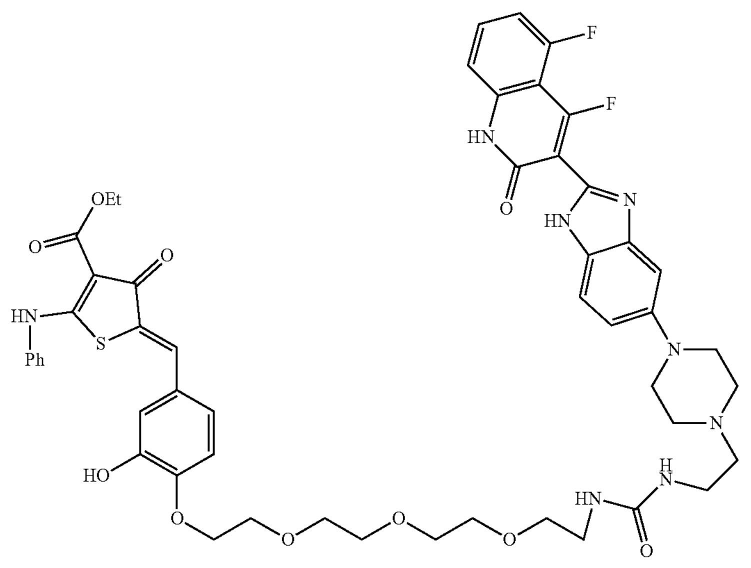

Compound 3

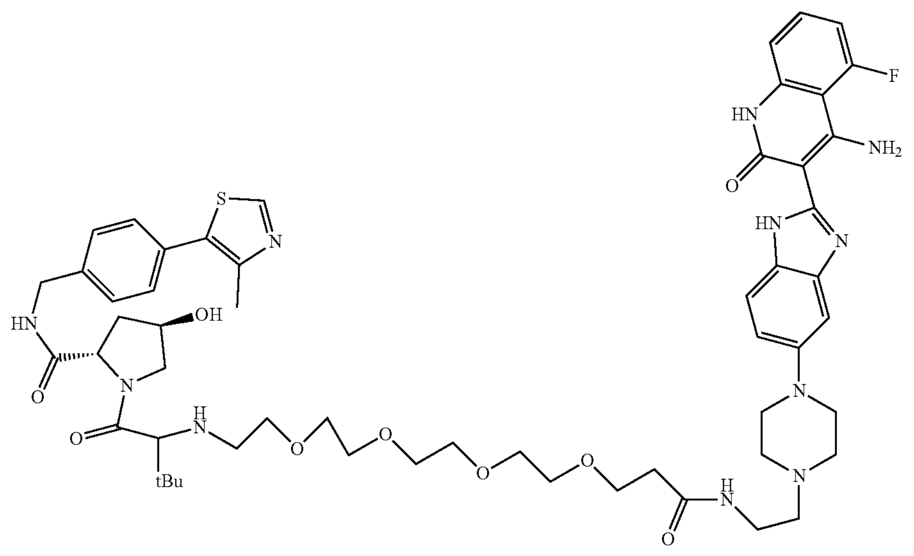

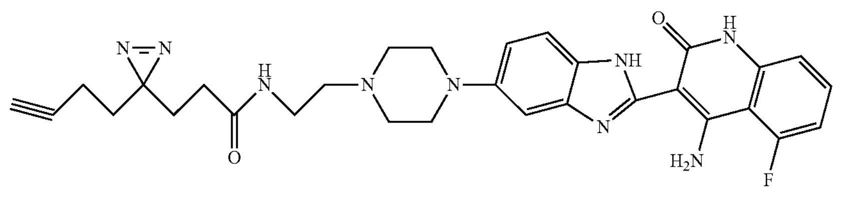

Dovitinib ChemCLIP Probe = Compound 4

BRIEF DESCRIPTION OF DRAWINGS

FIGS. 1A-1B illustrate Inforna based repurposing of a ReFrame small molecule library.

FIG. 1A illustrates at left 1024-member 3×2 RNA internal loop library (3×2 ILL) and 9300-member ReFRAME library and at right, library (1024)-versus-library (9300) screen probes over 9,500,000 combinations of RNA motif-small molecule interactions to identify the privileged RNA structures that bind small molecule medicines with high affinity.

FIG. 1B illustrates Inforna-based identification of Dovitinib (1) targeting pre-miR-21 's Dicer site inhibits its processing and hence its oncogenicity.

FIG. 2A illustrates Scheme of solution-based HTS as described[2]. Briefly, the fluorescence intensity of TO-PRO-3 is enhanced when bound to RNA. Displacement of TO-PRO-3 by hit compounds results in decreased fluorescence signal.

FIG. 2B illustrates distribution of the percent change in fluorescence induced by 9,300 ReFRAME and control compounds, revealing that 68 compounds reduce fluorescence by >3σ, carried forward to 2DCS selections.

FIG. 4A illustrates structure of parent compound 1, RIBOTAC 2, and PROTAC 3.

FIG. 4B illustrates scheme of RIBOTAC 2 dimerizing RNase L onto pre-miR-21 to enzymatically cleave it (top) and PROTAC 3 recruiting VHL onto RTK to induce its ubiquitination, leading to subsequent proteasome-mediated downregulation (bottom).

FIG. 4C illustrates that RIBOTAC 2 exhibited 25-fold increased miR-21 inhibitory activity and 100-fold decreased RTK inhibition, both as compared with 1, while 3 exhibited similar miR-21 inhibitory activity and 5-fold increased RTK inhibition.

FIG. 5A illustrates In vivo treatment of 2 (56 mg/kg, q.o.d., 30 days) decreased lung nodules (white nodules) stained with Bouin's solution (n=11 for vehicle; n=7 for 2).

FIG. 5B illustrates micrographs of lung tissue treated with 2 exhibited decreased miR-21 levels and unchanged pERK levels, while 1 exhibited decreased pERK levels and unchanged miR-21 levels (n=3). *, $p<0.05$, as tested by a two-tailed Student's t-test. All samples in the figure are biological replicates.

FIG. 6A illustrates in vivo treatment of 2 (56 mg/kg, q.o.d., 42 days) decreased urine albumin concentration, as normalized to urine creatinine in Alport mice. In contrast, 2 had no effect on urine from Wild Type (WT) mice.

FIG. 6B illustrates that RIBOTAC 2 derepressed PPARα expression in kidneys of Alport mice with no significant effect on PPARα expression in WT mice.

FIG. 6C illustrates that RIBOTAC 2 decreased pre-miR-21 levels in kidneys of both Alport and WT mice.

FIG. 6D illustrates PAS staining showing that RIBOTAC 2 prevented tubule injury observed in Alport mice. Tubule injury severity was scored from 0 to 4 by extent of injury as previously described[10], where 0 is no tubule injury (top left and right) whereas 4 is severe injury (bottom left). *, $p<0.05$;  $p<0.01$, * $p<0.001$, as determined by a two-tailed Student's t-test. For vehicle- and 2-treated WT mice, n=3; for vehicle-treated Alport mice, n=3; for 2-treated Alport mice, n=4. All samples shown are biological replicates.

FIG. 8A illustrates, Left, secondary structure of A-bulge RNA from 3×2 RNA ILL and its base pair mutant. Middle, binding curves of fluorescent binding assay between 1 and the A-bulge and 1 and the base pair mutant. No saturable binding was observed with the addition of up to 40 μM of the mutant RNA. Right, binding curves of fluorescent binding assay between 2, 3, 4, 7 and pre-miR-21's A-bulge.

FIG. 8B illustrates the In vitro Dicer inhibition assay results. Left, representative gel autoradiogram of the inhibition of Dicer processing of pre-miR-21 and the pre-miR-21 mutant by 1. Compound 1 inhibited the Dicer processing of pre-miR-21 with an $IC_{50}$ of 5 LLM but was unable to inhibit Dicer processing of mutant, which lacks a 1 binding site. Boxes indicate Dicer cleavage sites. "OH" indicates a hydrolysis ladder in which every base is cleaved; "T1" indicates cleavage of the RNA at G residues by T1 endonuclease under denaturing conditions. Right, quantification of inhibition of Dicer processing with 1 treatment. , p<0.01: * p<0.001, as determined by a paired two-tailed Student t-test.

FIG. 9A illustrates the scheme of Chem-CLIP probe 4 reacting with pre-miR-21 in cells to validate target engagement.

FIG. 9B illustrates that Chem-CLIP probe 4 retains the activity of 1, which decreases mature miR-21 levels and increases pre-miR-21 levels.

FIG. 9C shows in vitro Chem-CLIP of $^{32}P$-labeled pre-miR-21 WT RNA and mutant. Probe 4 dose-dependently enriched pre-miR-21 WT but not mutant, except at 100 μM where nonspecific reaction was observed. Control probe 5 did not enrich either RNA.

FIG. 9D, In vitro C-Chem-CLIP, shows that enrichment of pre-miR-21 by 4 can be competed off by parent compound 1 in a dose dependent manner.

FIG. 9E illustrates that in MDA-MB-231 cells, probe 4 reacted with pre-miR-21 whereas control probe 5 did not. C-Chem-CLIP studies showed that when cells were incubated with increasing concentrations of 1 or 3, the pull-down of pre-miR-21 with 4 (constant concentration) was similarly diminished and in a dose dependent manner. *, p<0.05;  p<0.01, * p0.001, as tested by a two-tailed Student t-test.

FIG. 10A illustrates scheme of Chem-CLIP probe 4 reacting with an RTK in cells to validate target engagement.

FIGS. 10B-10D show that Chem-CLIP probe 4 is enriched RTK FLT3 from MDA-MB-231 cells, and this enrichment can be competed off by 1 (FIG. 10B), 2 (FIG. 10C), 7 and 8 (FIG. 10D) in a dose dependent manner. Control probe 5, which lacks the RNA-binding module, did not enrich FLT3. All compounds have no effect on FLT3 expression, as indicated by Western blotting (labeled "Input").

FIG. 10E shows quantification of the experiments from FIGS. 10B-10D. RIBOTAC 2 at 10 μM competed off probe 4 to the same extent as 1 at 0.1 μM, indicating a 100-fold difference cellular protein occupancy between 1 and 2. The extent of depletion by 7 was between that observed for 1 and 2, suggesting that both chemical modification of 1 by attaching recruiter and its recruitment of RNase L contribute to the 100-fold lower protein binding of 2. Competition by 8 was similar to 1, indicating that the urea linker has no effect on protein binding.

FIGS. 11A-11D illustrate cellular characterization of 1 and its derivatives.

FIG. 11A shows that Compounds 1, 2, and 3 reduced mature miR-21 levels, as determined by RT-qPCR analysis. RIBOTAC 2 decreased pre-miR-21 levels via RNase L cleavage, while 1 and 3 increased pre-miR-21 levels, consistent with their mode of action, binding and inhibiting Dicer cleavage.

FIG. 11B shows global miRNA profiling of 1 and 2 in MDA-MB-231 cells, with 2 showing greater selectivity. Dotted lines indicate an FDR equal to 1% and a group variance of S0 (0.1).

FIG. 11C shows that Compounds 1, 2, and 3 derepressed PTEN expression, as determined in a luciferase-based assay.

FIG. 11D shows that Compound 1 derepressed PDCD4 expression by ~60% at 5 μM. *, p<0.05;  p<0.01, * p<0.001, as tested by a two-tailed Student t-test.

FIG. 12A shows that Compound 1 reduced the invasion of MDA-MB-231 cells.

FIG. 12B shows quantification of the MDA-MB-231 cell invasion from FIG. 9A FIG. 12C shows secondary structures of pre-miR-21 and its mutant encoded by two different plasmids.

FIG. 12D shows that Compound 1 inhibited the invasion phenotype of MCF-10A cells acquired by transfection of wild type (WT) pre-miR-21 but not that of mutant pre-miR-21, which lacks the 1 binding site.

FIG. 12E shows the quantification of the MCF-10A cell invasion from FIG. 12B. **, p<0.01, as tested by a two-tailed Student t-test.

FIG. 13A shows that Compound 2 oligomerized RNase L in a dose dependent manner.

FIG. 13B shows, Left, representative gel autoradiogram of the in vitro cleavage of pre-miR-21 WT RNA by RNase L, recruited by RIBOTAC 2. The box indicates the RNase L cleavage site at U33 and C34. "OH" indicates a hydrolysis ladder in which every base is cleaved; "T1" indicates all G residues, identified by cleaved by T1 endonuclease under denaturing conditions. Right, quantification of RNase L cleavage by recruitment with 2. *, p<00.5; , p<0.01, * p<0.001, as tested by a paired two-tailed Student t-test.

FIG. 14A shows the effect of t and 2 on pre-miR-21 levels in MDA-MB-231 cells, as determined by RT-qPCR. Consistent with their modes of action, RIBOTAC 2 reduced pre-miR-21 levels while 1 enhanced them. Addition of 1 in the presence of a constant concentration of 2 (1 μM) competed away cleavage of pre-miR-21 by the RIBOTAC.

FIG. 14B shows Negative control compound 6, which lacks the RNA-binding module, had no effect on pre-miR-21 levels, as determined by RT-qPCR. Negative control compound 7, which contains 1 but an inactive RNase L-recruiting module, acts like simple binding compound 1, increasing pre-miR-21 levels.

FIG. 14C shows immunoprecipitation of R_Nase L from MDA-MB-231 cells treated with 2 (1 μM), but not 6 or 7 (1 μM), enriched pre-miR-21. Importantly, 2 did not enrich a different pre-miRNA, pre-miR-210, that does not contain a 1-binding site.

FIG. 14D shows knock down of RNase L with an siRNA repressed cleavage of pre-miR-21 by 2.

FIG. 14E shows that Compound 2 (1 μM) and LNA-21 (100 nM) derepressed PDCD4 expression while 1 was unable to do so at the same concentration of 2. *, p<0.05; , p<0.01, * p<0.001, as tested by a two-tailed Student t-test.

FIG. 15A shows that Compound 2 reduced the number of invasive MDA-MB-231 cells.

FIG. 15B shows quantification of the number of invasive MDA-MB-231 cells from FIG. 15A.

FIG. 1.5C shows that Compound 2 inhibited the invasion phenotype of MCF-10A acquired by transfection of wild type pre-miR-21. In contrast, 2 was unable to rescue the invasion phenotype of MCF-10A acquired by transfection of a mutated pre-miR-21 where the binding site of 1 is ablated.

FIG. 15D shows quantification of the number of invasive MCF-10A cells from FIG. 15C. These plasmids were the same as those used in FIGS. 12A-12E. *, $p<0.05$; *** $p<0.001$, as tested by a two-tailed Student's t-test.

FIGS. 16A-16D illustrate that PROTAC 3 inhibits pre-miR-21 biogenesis similar to 1 and induces degradation of RTK FLT3, which can be competed off by 1 and 2, in MDA-MB-231 cells.

FIG. 16A shows that PROTAC 3 boosted pre-miR-21 levels, as determined by RT-qPCR, similar to 1, as expected for simple binding compound. Further, 3 abated the cleavage of pre-miR-21 by RIBOTAC 2 dose dependently.

FIG. 16B shows that PROTAC 3 induced degradation of FLT3 in a dose-dependent manner, and this induction of degradation can be competed off by co-treatment with 1 (FIG. 15C) or 2 FIG. 16D shows a 100-fold greater concentration of RIBOTAC 2 (10 μM) than 1 (0.1 μM) was required to compete off the target degradation of PROTAC 3. *, $p<0.05$; , $p<0.01$;  $p<0.001$, as tested by a paired two-tailed Student t test.

FIG. 1.6C shows cotreatment with 1 and 3.

FIG. 16D shows cotreatment with 2 and 3.

FIG. 17A shows a representative Western blot to study the function inhibition of ERK by 1.

FIG. 17B shows a representative Western blot to study the inhibition of ERK phosphorylation by RIBOTAC 2, which has reduced ability to inhibit ERK phosphorylation compared to 1.

FIG. 17C shows a representative Western blot to study inhibition of ERK phosphorylation by PROTAC 3, which is more potent than 1.

FIG. 17D shows quantification of the effect of compounds 1, 2 and 3 on ERK phosphorylation. RIBOTAC 2 at 5 μM dose inhibited ERK phosphorylation to the similar extent as compound 1 at 0.05 μM dose, or a 100-fold difference functional inhibition.

FIG. 18A shows a volcano plot showing proteome-wide changes induced by 1 (1 μM, a concentration that does not inhibit pre-miR-21 biogenesis).

FIG. 18B shows a volcano plot showing proteome-wide changes triggered by RIBOTAC 2 (1 FIG. 18C shows a volcano plot showing proteome-wide changes caused by LNA-21 (100 μM). Dotted lines represent a false discovery rate (FDR) of 5% and an S0 of 0.1.

FIG. 20A shows a cumulative distribution plot that shows no significant changes for miR-21 regulated proteins upon treatment with 1 μM of 1, a concentration that does not inhibit pre-miR-21 biogenesis. Proteins regulated by miR-21 were predicted by TargetScanHuman v7.2 (n=390). Approximately 18% of miR-21-5p targets (70/390) were detectable in MDA-MB-231 cells.

FIG. 20B shows significant increase in abundance was observed for miR-21 regulated proteins upon treatment with 2 (1 μM).

FIG. 20C shows significant increase in abundance was observed for miR-21 regulated proteins upon treatment with 2 LNA-21 (100 nM). As a control, we investigated changes in proteins regulated by miR-let-7-5p, which has a similar expression level as miR-21 in MDA-MB-231 cells. Downstream protein targets of miR-let-7-5p (n=1207) were predicted by TargetScanHuman v7.2. Approximately 13% of miR-let-7-5p targets (160/1207) were detectable in the global proteomics analysis. Targets for context++ scores <−0.1 or −0.25 in miR-21-5p or miR-let-7-5p were calculated for cumulation distributions.

FIG. 21A shows a plot of mouse exposure to 1 in plasma, kidney, or lung at various doses (mpk), determined 48 h post-treatment (n=3).

FIG. 21B shows a plot of mouse exposure to 2 in plasma, kidney, or lung at various doses (mpk), determined 48 h post-treatment (n=3).

FIG. 21C shows weight change of NOD/Scid mice injected intravenously (i.v. tail vein) with MDA-MB-231-Luc cells, which metastasize to the lung[12], upon treatment with 81 mg/kg of 1 or 56 mg/kg of RIBOTAC 2 every other day (q.o.d.), beginning 8 days post tumor cell injection. Over 38 days, 2 treatment did not cause significant changes in weight compared to vehicle treatment. However, 1 treatment could only continue for 12 days due to toxicity. For each treatment, (n=11 for vehicle; n=10 for 1; n=7 for 2).

FIG. 21D shows graphic results of treatment of WT Col43$\alpha^{++}$ mice (control for Alport Syndrome studies) with 2 over 6 weeks gained weight at a similar rate as vehicle-treated mice (n=3).

FIG. 21E shows graphic results for Alport mice receiving 2 treatment gained more weight than vehicle-treated mice and maintained stable weights after one month of treatment, whereas vehicle-treated mice began to lose weight (for vehicle-treated Alport mice, n=3; for 2-treated Alport mice, n=4). Both WT (FIG. 21D) and Alport mice (FIG. 21E) were treated with 56 mg/kg (q.o.d.) of 2.

DEFINITIONS

Figure 1A:
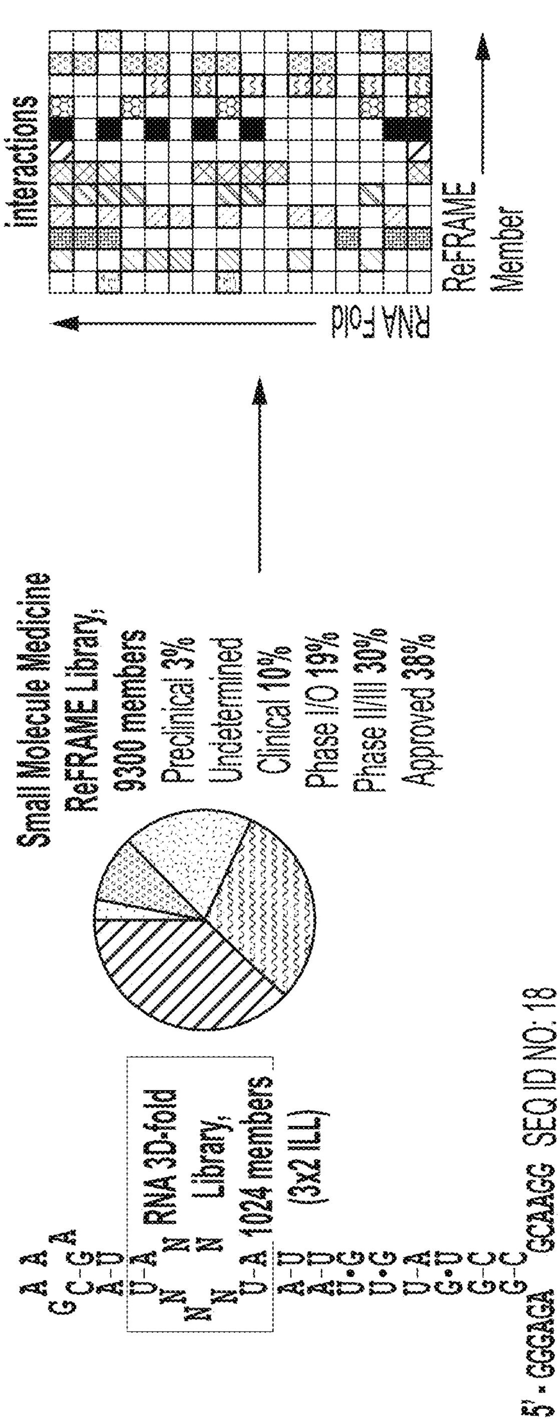
Figure 2A:
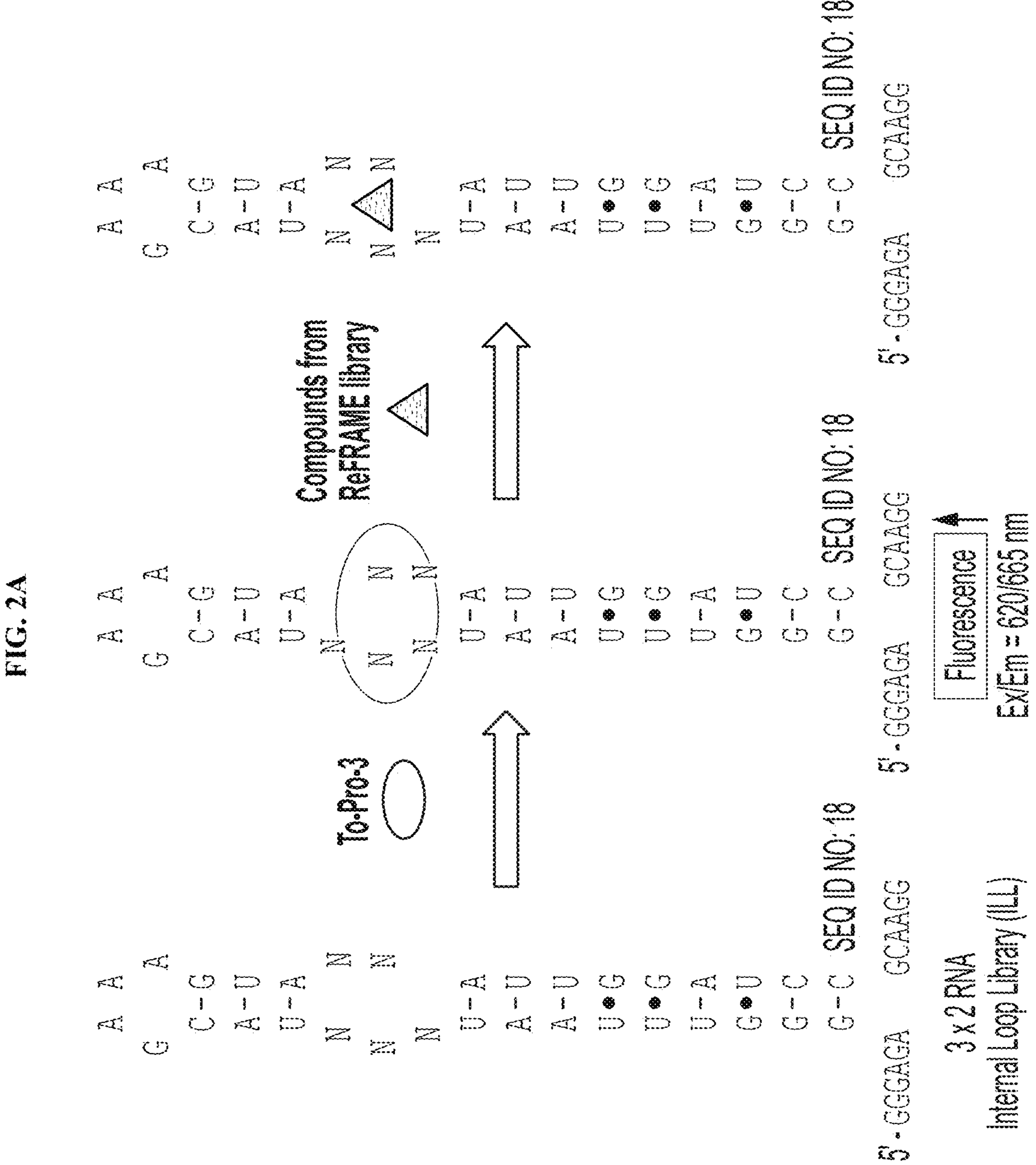
FIGS. 2A-2B illustrate dye displacement assay results.
Figure 2B:
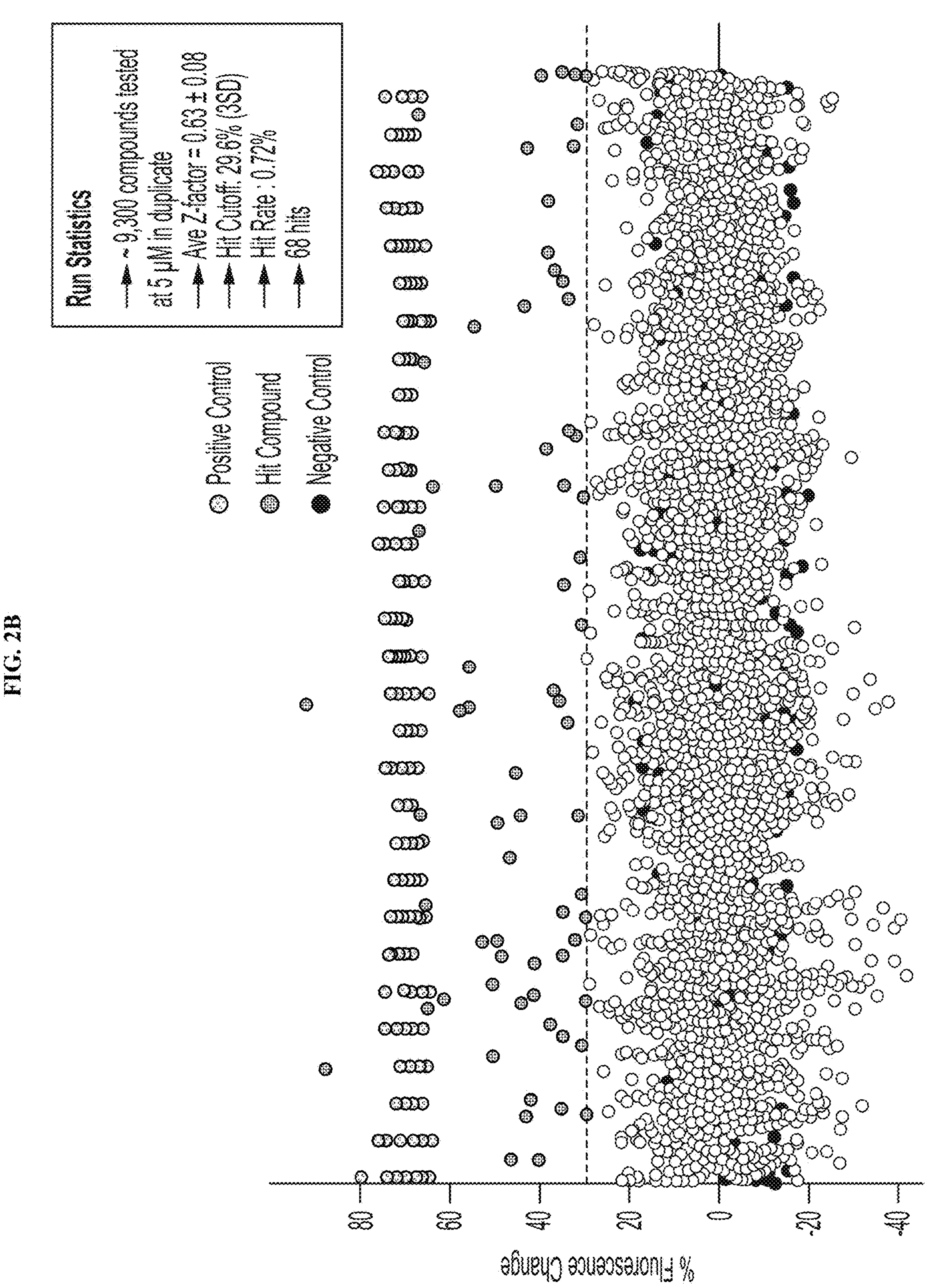

Unless defined otherwise, all technical and scientific terms used herein have the same meaning as commonly understood by a person of ordinary skill in the art.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

The term "may" in the context of this application means "is permitted to" or "is able to" and is a synonym for the term "can." The term "may" as used herein does not mean possibility or chance.

It is also to be understood that as used herein and in the appended claims, the singular forms "a," "an," and "the" include plural reference unless the context clearly dictates otherwise, for example, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and the right is reserved to revise the application or claims to refer specifically to any individual member or any subgroup of members of the Markush group.

The expression "effective amount", when used to describe therapy to an individual suffering from a disorder, refers to the amount of a drug, pharmaceutical agent or compound of the invention that will elicit the biological or medical response of a cell, tissue, system, animal or human that is being sought, for instance, by a researcher or clinician. Such responses include but are not limited to amelioration, inhibition or other action on a disorder, malcondition, disease, infection or other issue with or in the individual's tissues wherein the disorder, malcondition, disease and the like is active, wherein such inhibition or other action occurs to an extent sufficient to produce a beneficial therapeutic effect. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

"Substantially" as the term is used herein means completely or almost completely: for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed., provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

At various places in the present specification substituents of compounds of the invention are disclosed in groups or in ranges. It is specifically intended that the invention include each and every individual subcombination of the members of such groups and ranges. For example, the term "C1 -C6 alkyl" is specifically intended to individually disclose methyl, ethyl, propyl, isopropyl, n-butyl, sec-butyl, isobutyl, etc. For a number qualified by the term "about", a variance of 2%, 5%, 10% or even 20% is within the ambit of the qualified number.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, β-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.,* 33, 201-217, incorporated by reference herein.

Each of the terms "halogen," "halide," and "halo" refers to —F, —Cl, —Br, or —I.

The term "azide" or "azido" can be used interchangeably and refers to an $—N_3$ group (—N═N═N) which is bound to a carbon atom and is zwitterionic (carries a + and − charge respectively on the middle nitrogen and the terminal nitrogen). The azide group is a reactant in "click chemistry" which is a copper catalyzed azide-alkyne 1,3 dipolar cycloaddition (Sharpless etal., *Angewandte Chemie,* 41, 2596 et seq. (2002).

A "hydroxyl" or "hydroxy" refers to an —OH group.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases, one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound of the invention can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein, and unless otherwise specified, the term "compound" is inclusive in that it encompasses a compound or a pharmaceutically acceptable salt, stereoisomer, and/or tautomer thereof. Thus, for instance, a compound of Formula I includes a pharmaceutically acceptable salt of a tautomer of the compound.

The terms "prevent," "preventing," and "prevention" refer to the prevention of the onset, recurrence, or spread of the disease in a patient resulting from the administration of a prophylactic or therapeutic agent.

A "patient" or "subject" includes an animal, such as a human, cow, horse, sheep, lamb, pig, chicken, turkey, quail, cat, dog, mouse, rat, rabbit or guinea pig. In accordance with some embodiments, the animal is a mammal such as a non-primate and a primate (e.g., monkey and human). In one embodiment, a patient is a human, such as a human infant, child, adolescent or adult.

The term miRNA means a micro RNA sequence that is non-coding for peptides and functions at least for mRNA silencing and post-translational regulation of gene expression. Complementary base pairing of miRNA with messenger RNA molecules manages translation of the mRNA by up and/or down regulation, inhibition, repression and similar translation effects. Typical pre- and pri-miRNA sequences include structured and unstructured motifs. A structured motif is a segment of a pre-miRNA and its embedment within a pri-miRNA having a stable three-dimensional structure that is not wholly dependent upon the particular nucleotide sequence of the structure motif. Hairpin stem, bulge and/or terminal loop regions of pre-miRNA's are typical structured motifs. Groups of miRNAs often cooperate to manage mRNA function. An example is the pri-miRNA-17-92 cluster and the resulting pre-miRNA's and mature miRNA's produced by nuclease action on the cluster and pre-miRNA's respectively.

The terms pri-miRNA and pre-miRNA are the precursor RNA transcripts from which mature miRNA is produced. Transcription of DNA in the cell nucleus produces among other RNA molecules, pri-miRNA, a long RNA sequence which is capped and polyadenylated. Cleavage of the pri-miRNA and RNA chain processing in the nucleus produces the shorter pre-miRNA for export to the cellular cytoplasm. Pre-miRNA is further processed in the cytoplasm by RNAase Dicer to produce double stranded short RNA and one of the two strands becomes mature, single strand miRNA for interaction with messenger RNA.

DETAILED DESCRIPTION

To study if small molecule medicines indeed bind RNA, the RNA binding capacity of the state-of-the-ait small molecule medicine collection ReFRAME (Repurposing, Focused Rescue, and Accelerated Medchem)[2] was profiled (FIG. 1A). A dye displacement assay revealed that 68 of the 9300 members of ReFRAME (0.7%) bound a 3×2 RNA internal loop library (3×2 ILL). This library has 1024 RNA three-dimensional (3D) folds that are present in human RNAs (FIGS. 1A-1B, FIGS. 2A-2B). Collectively, the screen probed >9.5 million potential interactions (FIG. 1A) 3.

Figure 3A:
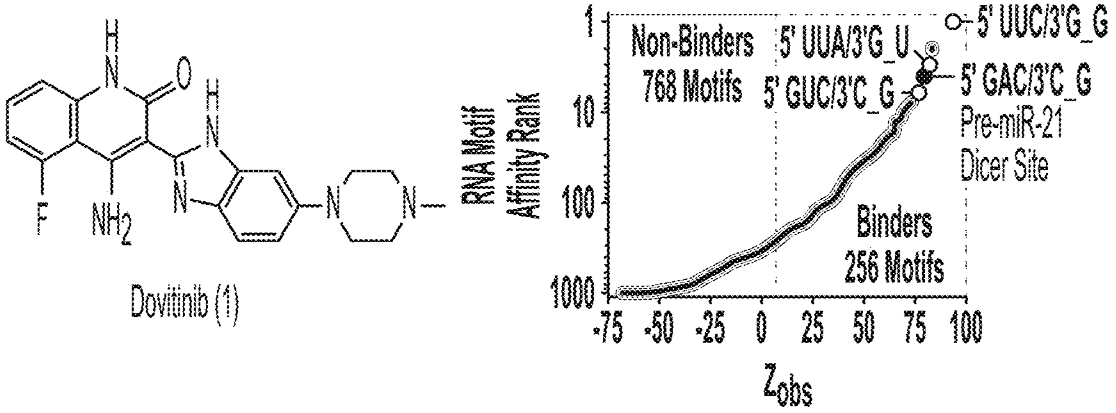
FIGS. 3A-3B illustrate Inforna generated fitness plots showing four different medicines bound RNA targets avidly. $Z_{obs}$ is a parameter of statistical confidence. RNA motifs with $Z_{obs}>8$ ($p<0.0001$) are avid binders, whereas R NAs with $Z_{obs}<8$ are non-binders 5. There were 256 binding motifs for Dovitinib (1), 278 motifs for Piroxantrone, 284 motifs for Delparantag, and 274 motifs for Metiazinic Acid. Fitness scores were calculated by normalizing $Z_{obs}$ value to the most statistically significant RNA motif binder (Fitness score=100)[5]. Black dots indicate the compound binds to the RNA motif in a Dicer or Drosha functional site with Fitness Scores>80, whereas white dots indicate RNA motifs are present in non-functional sites. Among, the 256 motifs for Dovitinib (1), an A bulge (5'GAC/3'C_G) in the Dicer processing site of pre-miR-21, is the most fit with a score of 85.
Figure 3A:
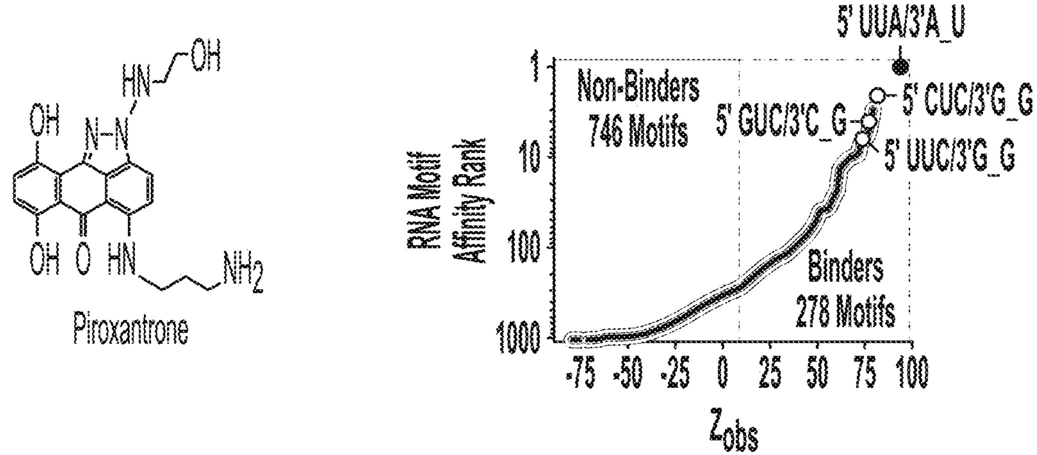
Figure 3B:
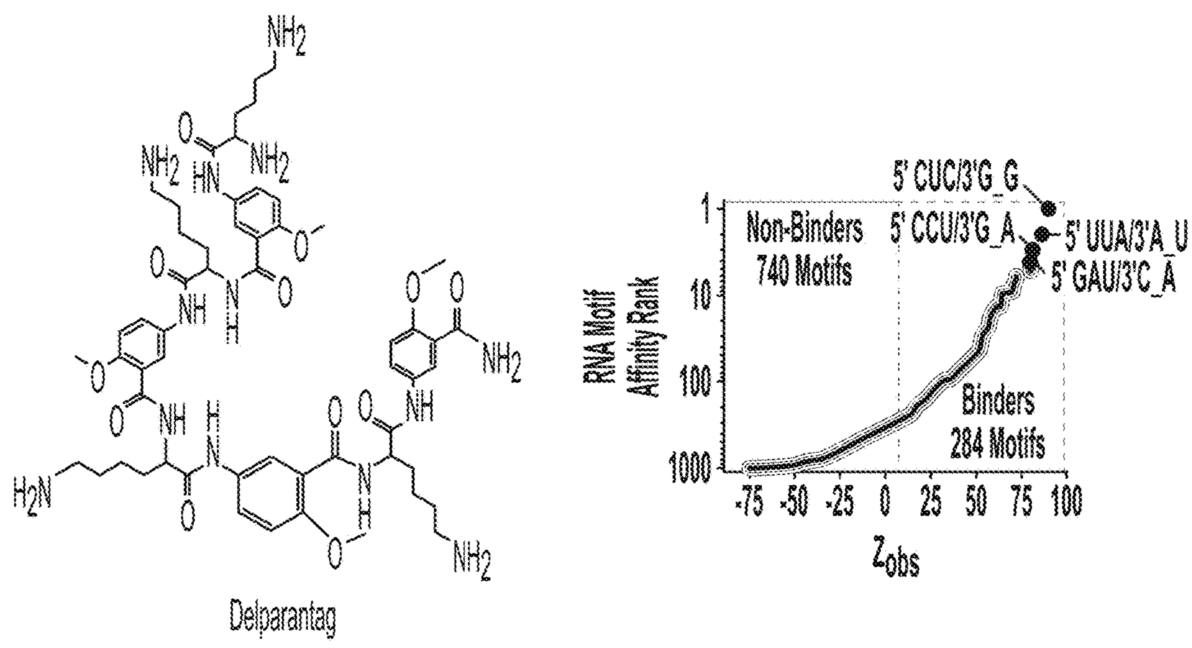
Figure 3B:
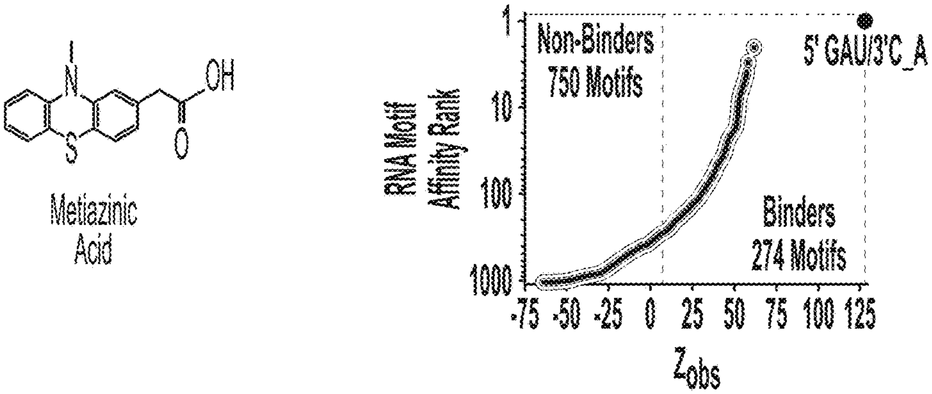

The precise 3D RNA folds that avidly bound each medicine were identified using a profiling strategy dubbed AbsorbArray[4]. In this experiment, small molecules are non-covalently adhered to a microarray surface, which is then hybridized with an RNA 3D fold library, in this case 3×2 ILL, under stringent conditions (FIGS. 1A-1B). RNAs from the library that bound each medicine were purified from the array surface, amplified, and sequenced by RNA-seq (FIGS. 1A-1B)[4]. Rigorous statistical analysis of the RNA-seq data defined the affinity landscape between the RNA 3D folds for each medicine, as we have previously described[5]. A series of four different medicines for multiple indications bound RNA targets avidly (FIGS. 3A-3B). Of these four, Davitinib was chosen as a representative example for repurposing of a small molecule having known biological activity.

This annotated series of RNA fold-small molecule recognition events were mined in a target agnostic manner against the folded RNA structures in the human genome to rationally repurpose the medicines by using Inforna (FIG. 1B). Inforna is a lead identification strategy that folds RNA sequences and then mines these folds against a database of RNA-small molecule interactions 6.

Figure 8A:
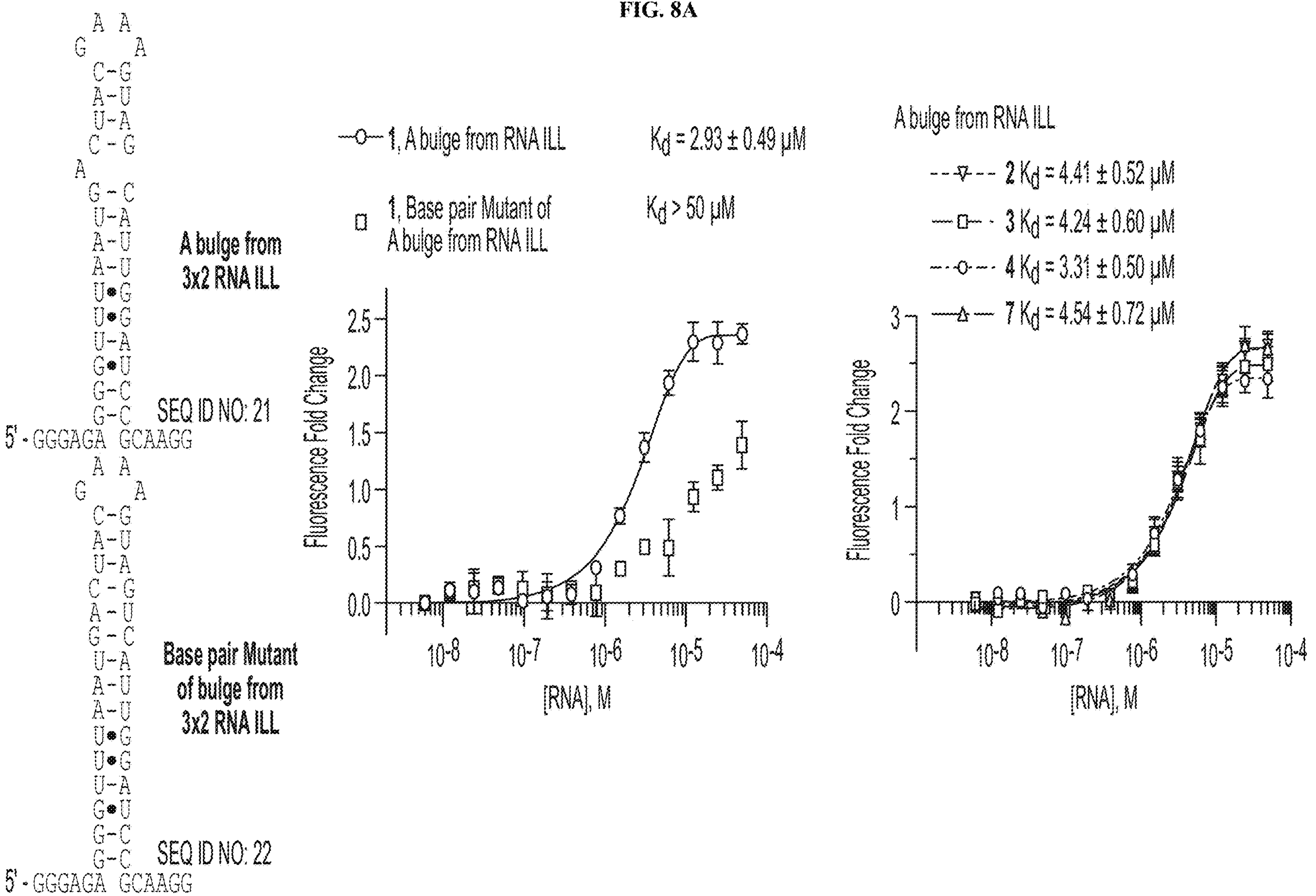
FIGS. 8A-8B illustrate In vitro characterization of compounds shows 1 and various derivatives bind to pre-miR-21's A-bulge avidly and selectively.
Figure 8B:
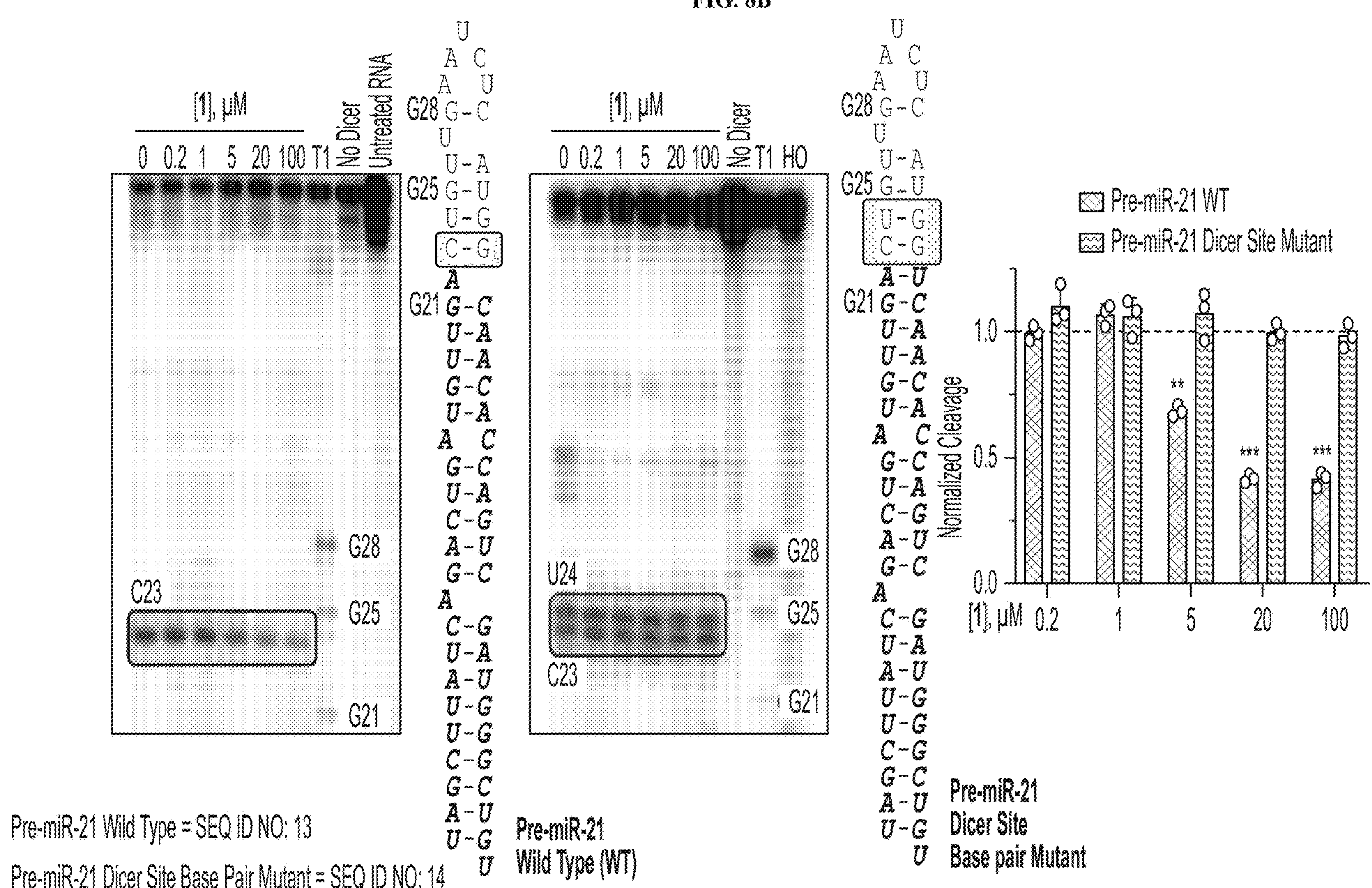

Indeed, Inforna identified that Dovitinib (1), a clinically-used receptor tyrosine kinase (RTK) inhibitor[7] could be repurposed for the precursor of microRNA-21 (pre-miR-21) (FIG. 1B). This microRNA (miRNA) is associated with many diseases, including cancer[8, 9] and the kidney disease Alport Syndrome (AS)[10]. MiRNAs act by suppressing translation of messenger RNAs (mRNAs) by binding to their 3' untranslated regions (UTRs) via base pairing (FIG. 1B)[11, 12]. They are transcribed as primary microRNAs (pri-miRNAs) that are processed into pre-miRNAs by the nuclear ribonuclease Drosha, which are further processed to mature miRNAs by the cytoplasmic nuclease Dicer (FIG. 1B). Dovitinib (1) binds specifically to the Dicer processing site in pre-miR-21 with a $K_d$ of 3 μM, with no binding to a control RNA (FIG. 8A). This binding inhibited the in vitro processing of pre-miR-21 but had no effect on a mutant pre-miR-21 that ablates Dovitinib's binding site (FIG. 8B).

Chemical synthesis, guided by the structure of Dovitinib bound to a receptor tyrosine kinase (an RTK)[13] (see chemical structure in FIG. 7), provided a derivative of Dovitinib (1) that cross-links to its cellular targets, a method dubbed chemical cross linking and isolation by pull-down (Chem-CLIP)[14]. The Chem-CLIP probe is a diazirine-containing derivative (Compound 4) that can react with both cellular RNAs and proteins upon UV-light exposure. That is, the probe enabled the study of the occupancy of both the canonical target, the RTK, and the repurposed target, pre-miR-21. Notably, the Chem-CLIP probe, Compound 4 and 1 have similar activities, and thus the former can be used to study cellular occupancy (FIG. 8A and FIG. 9B).

Figure 9A:
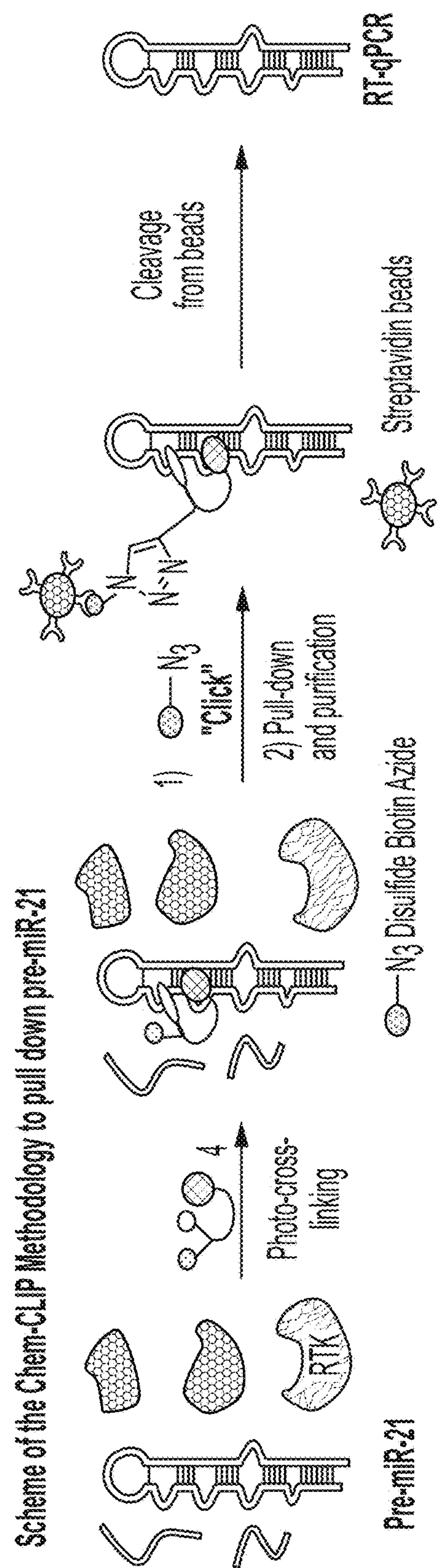
FIGS. 9A-9E illustrate Chem-CLIP and C-Chem-CLIP show direct target engagement of pre-miR-21 by 1 and 3.
Figure 9B:
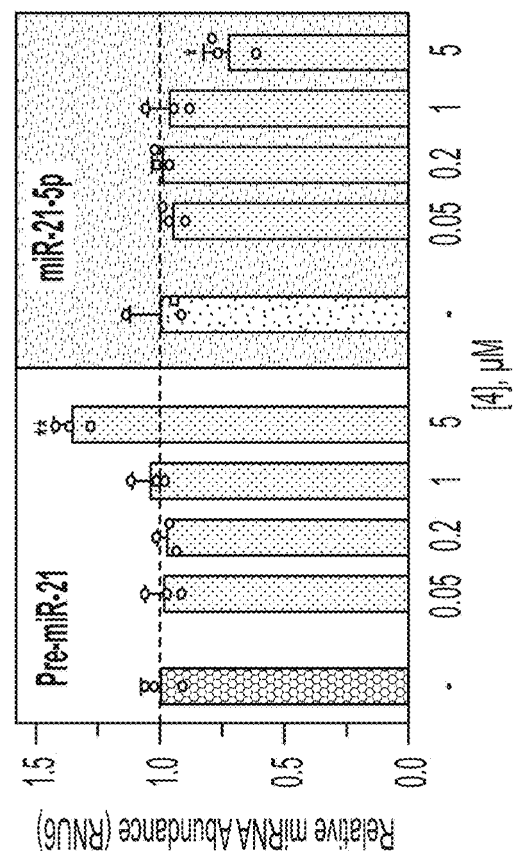
Figure 9C:
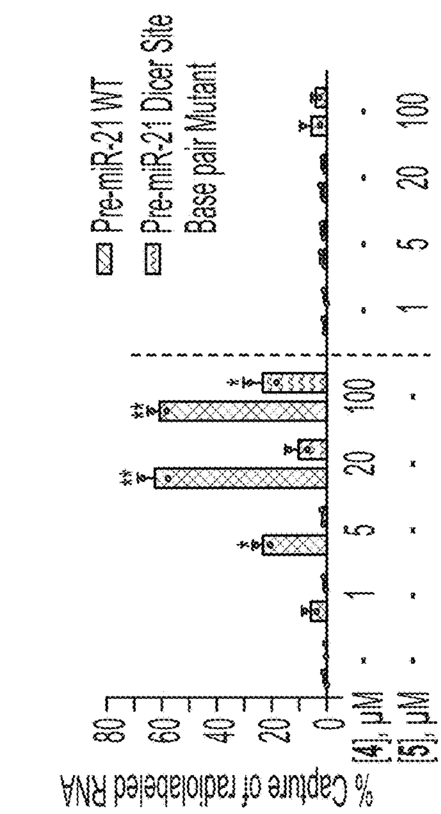
Figures 9D, 9E, 10A:
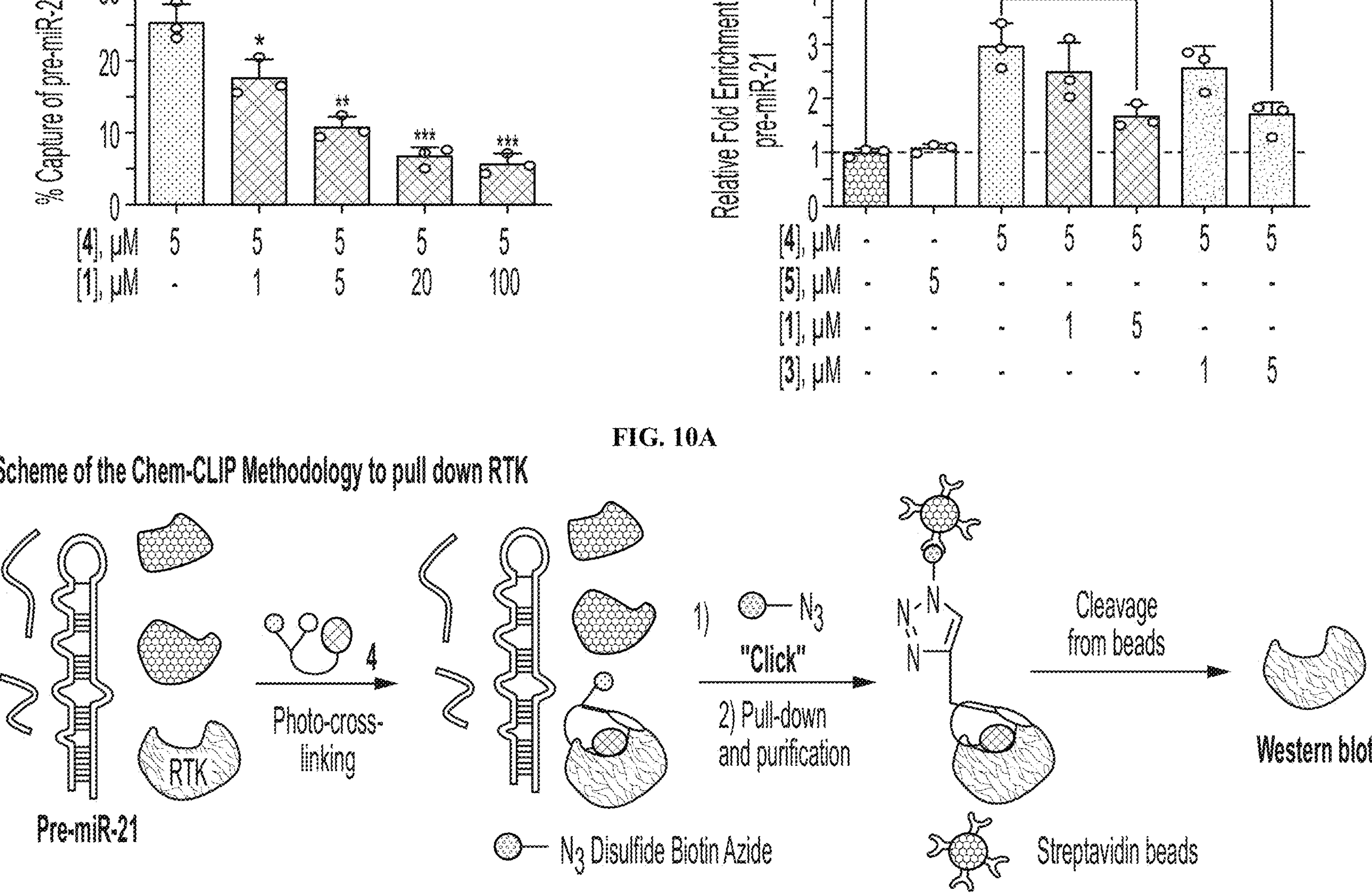
FIGS. 10A-10E illustrate that Chem-CLIP and C-Chem-CLIP show direct target engagement of an RTK by 1, 2, 7 and 8.

The Chem-CLIP probe was added to triple negative breast cancer (TNBC) cell line MDA-MB-231 to define cellular occupancy of RNA and protein targets (FIG. 9A and FIG. 10A). Both Vascular Endothelial Growth Factor Receptor 1 (FLT3), an RTK avidly bound by Dovitinib[15], and pre-miR-21 were significantly enriched in the pull-down fraction, consistent with the hypothesis that this medicine binds both targets (FIGS. 9A-9E and FIGS. 10A-10E). No enrichment was observed with a control Chen-CLIP probe that lacks the RNA-binding module (FIGS. 9A-9E and FIGS. 10A-10E). Competitive Chem-CLIP was used to study Dovitinib (1) itself to assess the relative binding to the RNA and protein targets (FIGS. 9A-9E and FIGS. 10A-IDE).

Figure 11A:
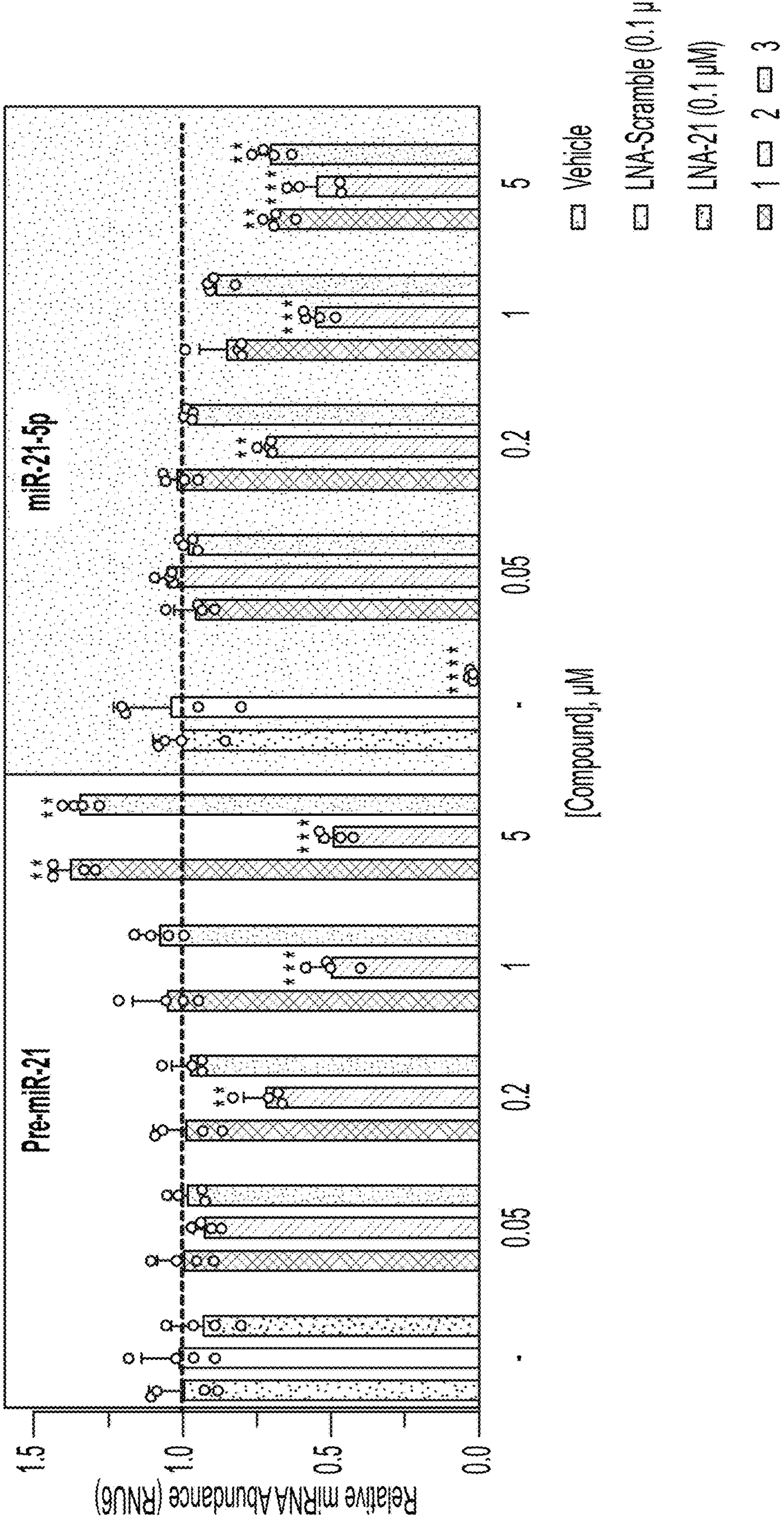
Figure 11C:
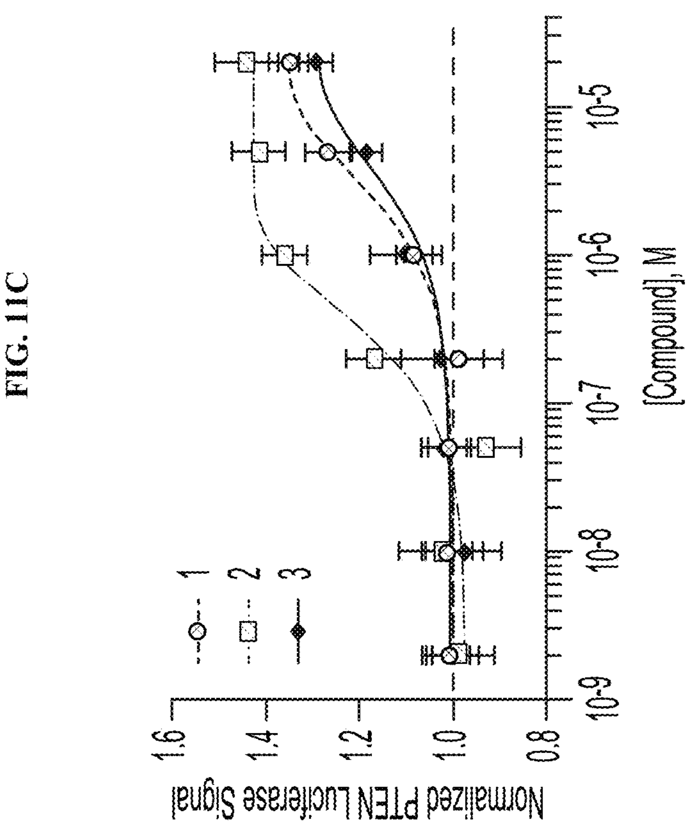
Figure 11B:
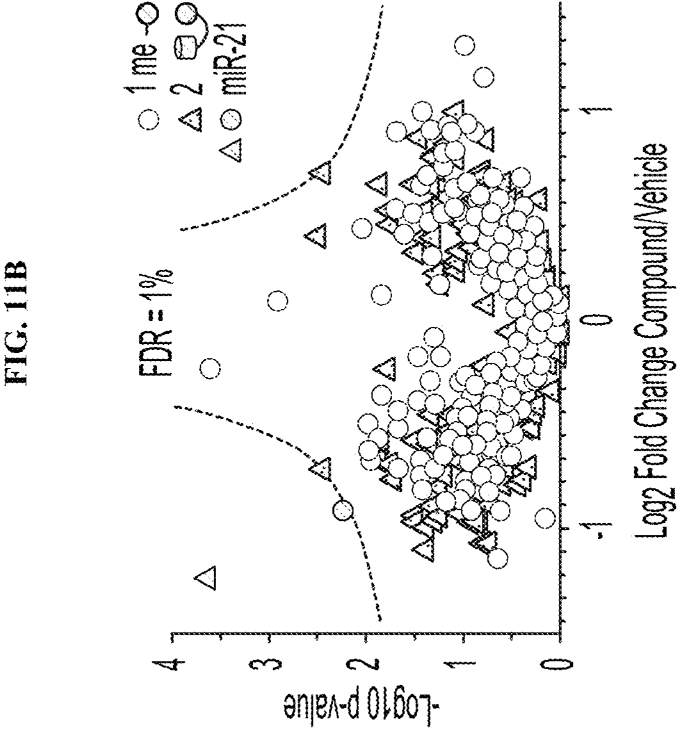
Figure 12A:
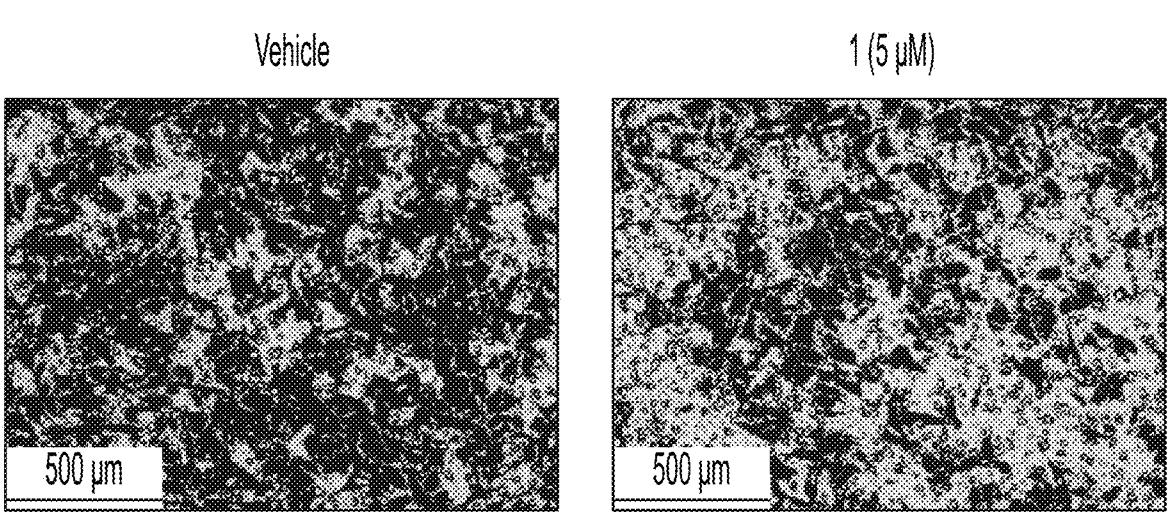
FIGS. 12A-12E illustrate that Compound 1 reduced invasion (miR-21 mediated phenotype) of MDA-MB-231 and transfected MCF-10A cells.
Figure 12B:
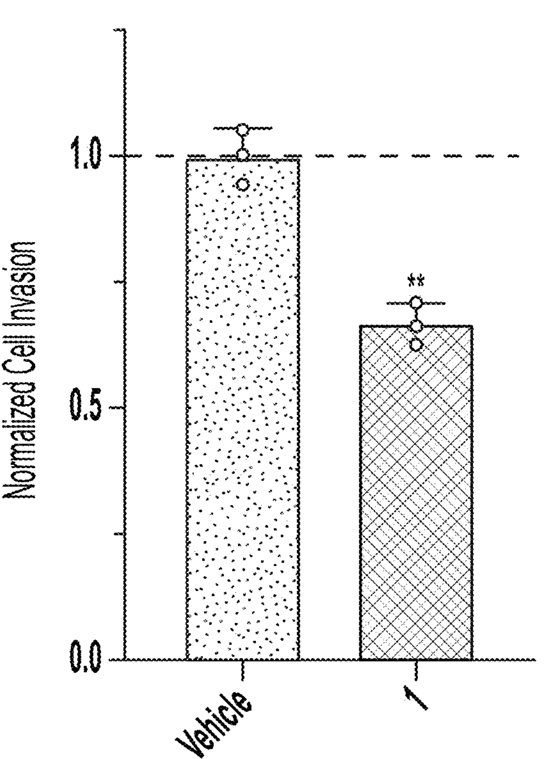
Figure 12C:
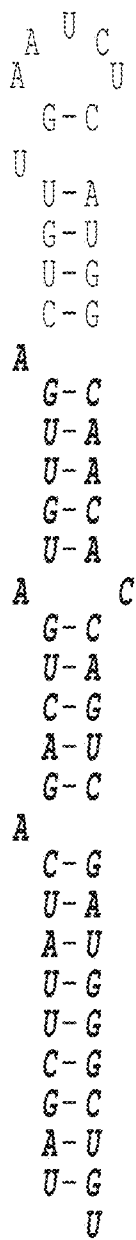
Figure 12C:
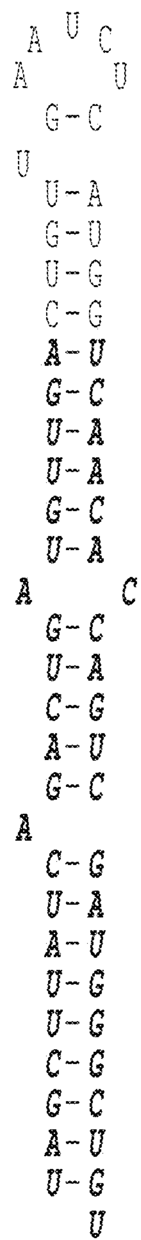
Figure 12D:
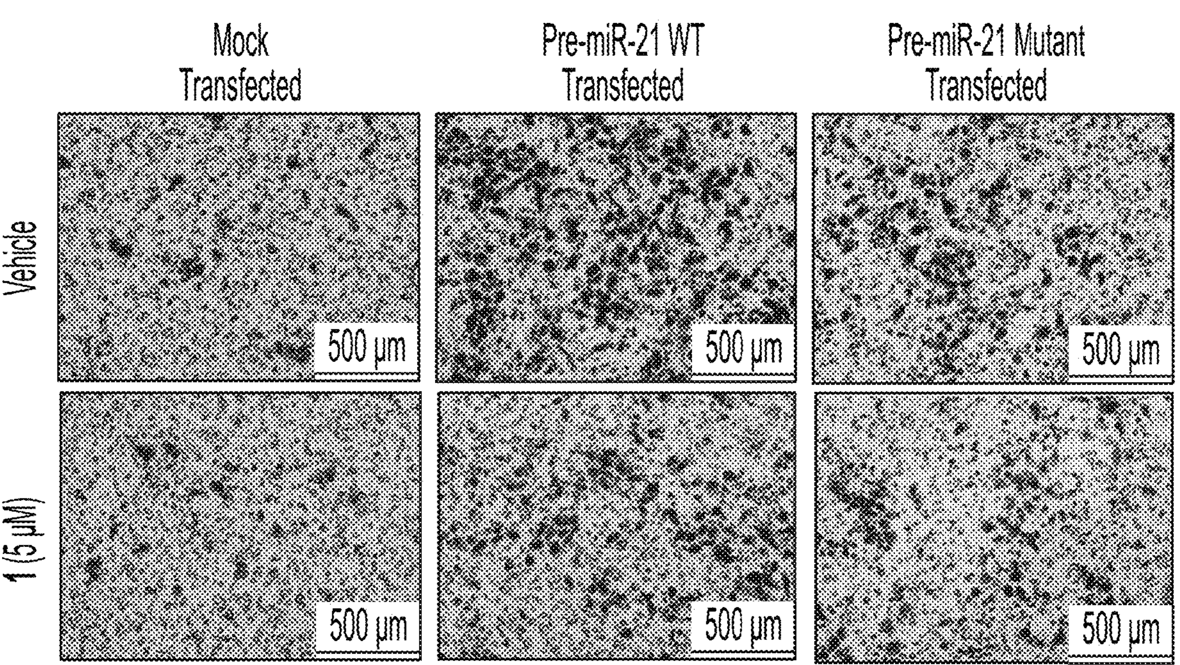
Figure 12E:
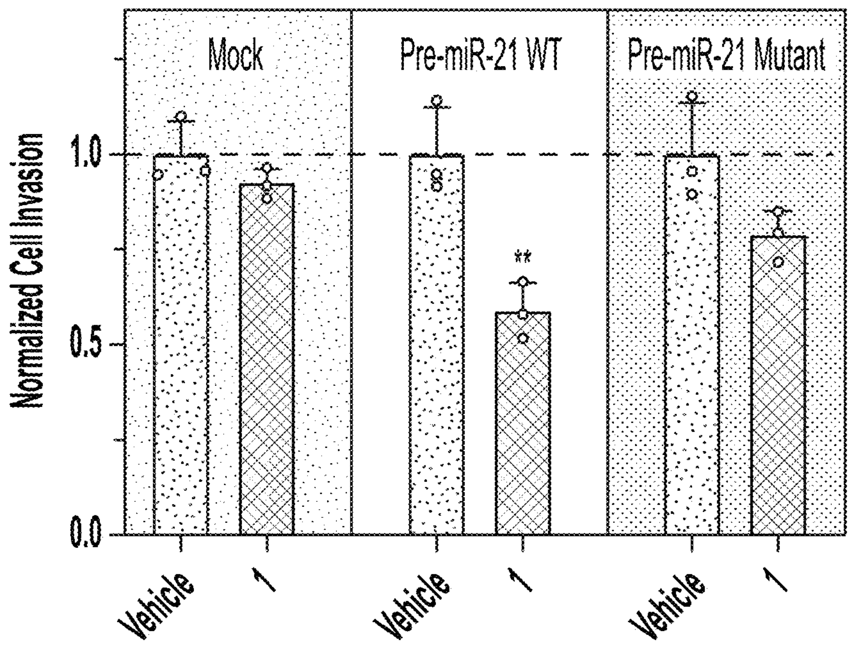

Given the direct engagement of pre-miR-21 by Dovitinib in TNBC cells, a study was conducted to determine whether 1 inhibited the RNA's biogenesis and hence its downstream biological functions. Indeed, 1 significantly inhibited pre-miR-21 processing in TNBC cells, significantly reducing mature miR-21 levels at a 5 μM dose (FIG. 11A). Consistent with its mode of action, inhibition of Dicer processing, 1 increased pre-miR-21 levels (FIG. 11A). Profiling the effect of 1 on all miRNAs showed that 1 was modestly selective for the repurposed target (FIG. 11B). In agreement with the reduction of mature miR-21 levels, 1 derepressed the expression of proteins that it regulates including Programmed Cell Death 4 (PDCD4) and Phosphatase and Tensin Homolog (PTEN, FIGS. 8C-8D). Further, 1 inhibited invasiveness of MDA-MB-231 TNBC cells, a phenotype associated with miR-21 overexpression (FIGS. 12A-12E)[8]. Importantly, the compound had no effect on the invasive nature of MCF-10A cells, a model of healthy breast epithelium that does not appreciably express miR-21. Overexpression of pre-miR-21 in MCF-1CA cells, however, triggered the cells to become invasive, and addition of 1 reverted this phenotype (FIGS. 12A-12E). Interestingly, overexpression of the pre-miR-21 mutant in which the 1 binding site is ablated also increases the invasiveness of MCF-1CA cells but are insensitive to 1 treatment. Thus, 1 selectively rescues a miR-21-mediated phenotype in cells.

Figure 4A:
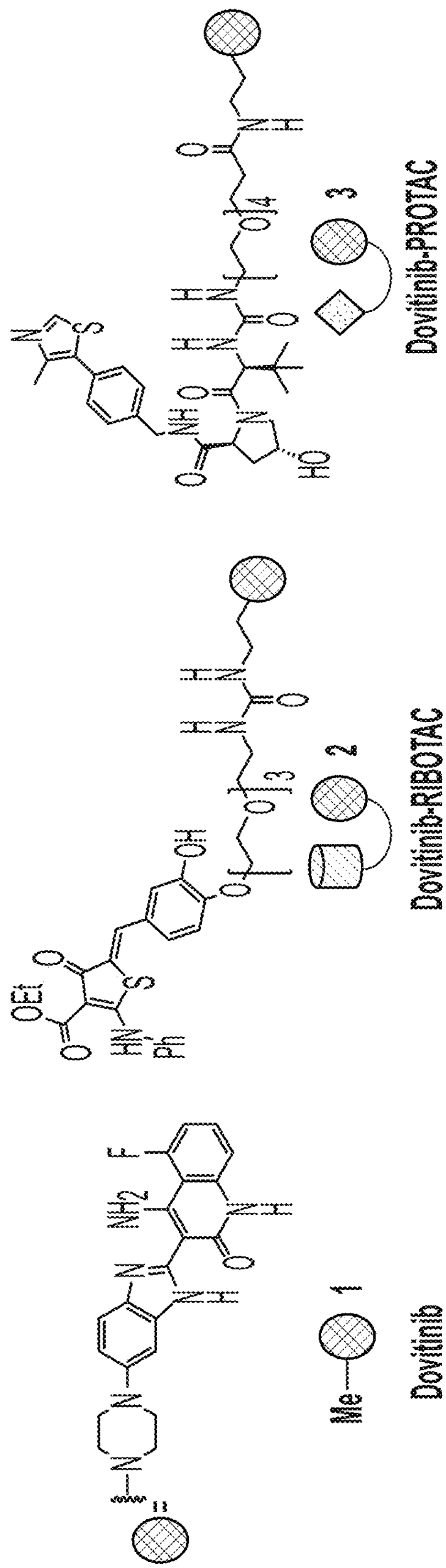
FIGS. 4A-4C illustrate dovitinib-based rational design of a RIBOTAC for RNA and a PROTAC for protein.

Given the bias in the parent compound for affecting the canonical protein target (100 nM) over the repurposed RNA target (5 μM), a strategy was sought to enhance and direct 1's activity toward pre-miR-21. One such way to do so is via targeted degradation, which has not yet been studied as applied to drug repurposing. Thus, Compound 1 was converted into both an RNA degrader, or ribonuclease targeting chimera (2, RIBOTAC)[16] and a protein degrader, or proteolysis targeting chimera (3, PROTAC)[17] (FIG. 4A).

Figure 13A:
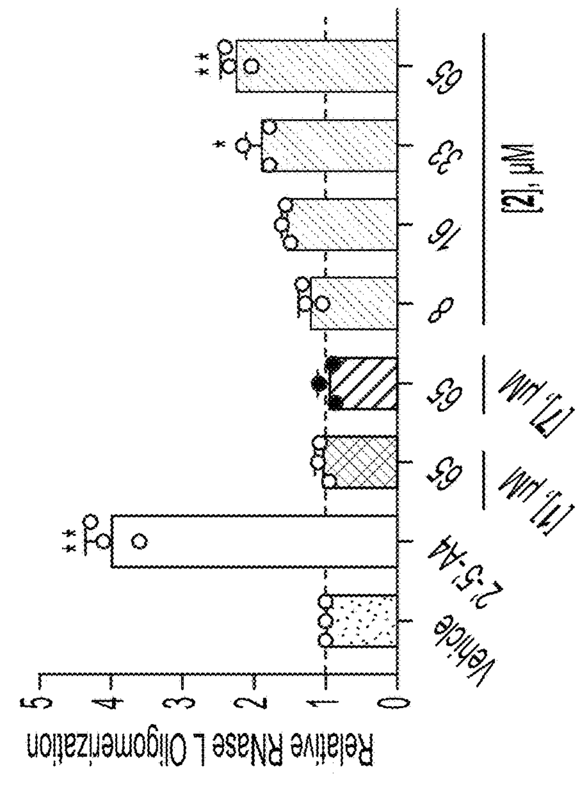
FIGS. 13A-13B illustrate that compound 2 recruited and activated RNase L to cleave pre-miR-21 in vitro.
Figure 13B:
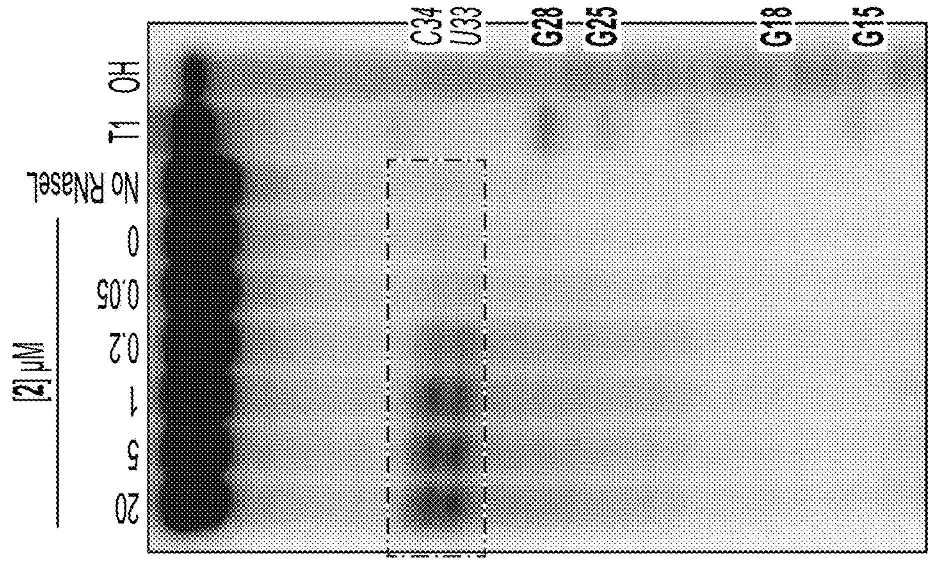
Figure 13B:
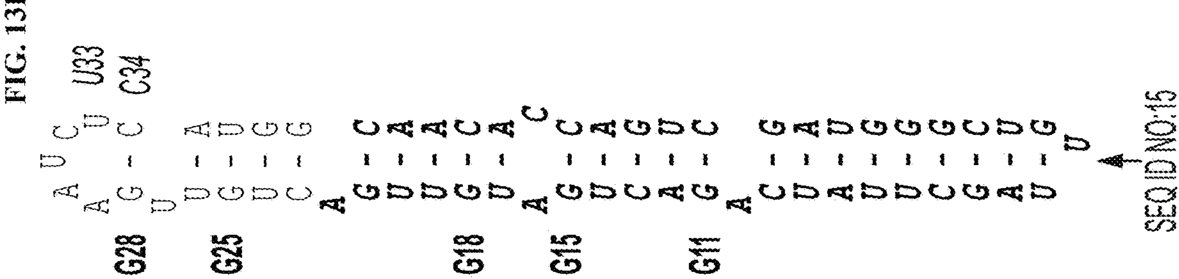
Figure 13B:
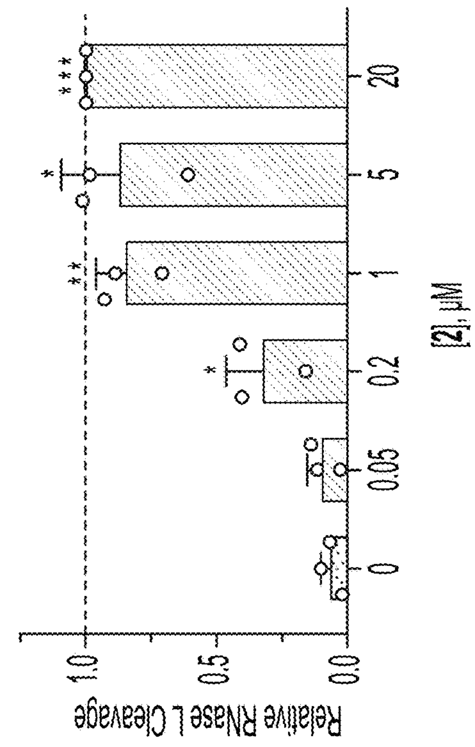

The RIBOTAC 2 binds pre-miR-21 and recruits and activates ribonuclease L (RNase L) to cleave the target (FIG. 4B)[18]. RNase L is present in all cells at minute quantities as an inactive monomer. In response to viral infection, the cell synthesizes 2'-5'polyadenylate, which binds RNase L, both dimerizing and activating the enzyme. A small molecule activator of RNase L was recently described[18], which was appended to small molecule to 1 to create the chimera. As expected, 2 recruits and dimerizes inactive monomeric RNase L into the active dimer in vitro, cleavage pre-miR-21 proximal to the Dicer site (FIGS. 13A-13B).

Figure 14A:
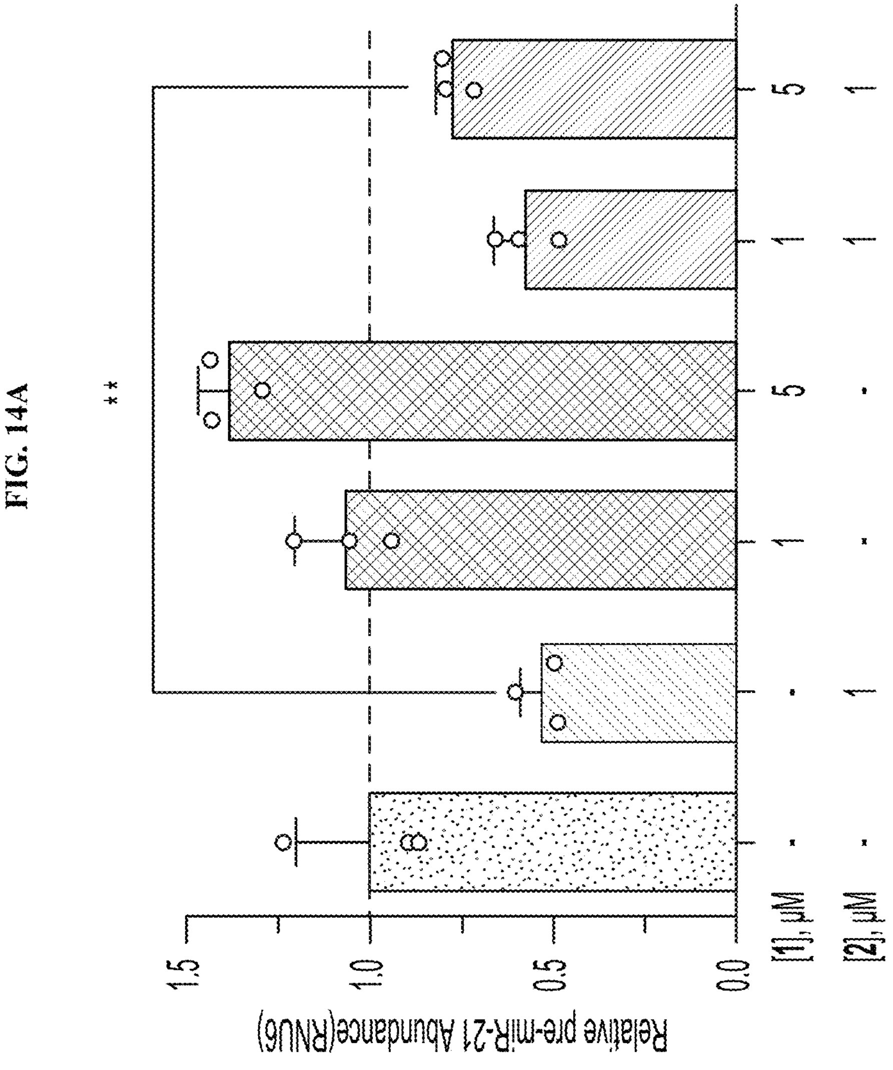
FIGS. 14A-14E illustrate cellular characterization of the selective cleavage of pre-miR-21 by RIBOTAC 2 in MDA-MB-231 cells.

In MDA-MB-231 cells, 2 has significantly enhanced selectivity and potency against pre-miR-21 as compared to 1. In particular, 1 decreased mature miR-21 levels by 32±4% at a 5 μM dose while a similar reduction was observed with only 200 nM of 2, a 25-fold increase in potency (FIG. 11A). In addition, pre-miR-21 levels were decreased by 2-treatment while 1 enhanced these levels, as expected for compounds that degrade or inhibit pre-miRNA processing, respectively (FIG. 11A). Co-addition of increasing amounts of 1 and constant amounts of 2 competed away cleavage of pre-miR-21, indicating 1 and 2 bind the same sites in pre-miR-21 (FIG. 14A). Two lines of experimental evidence confirmed that cleavage was indeed RNase L-dependent: (i) an RNase L antibody immunoprecipitated pre-miR-21 in cells treated with 2, showing direct formation of the ternary complex between 2, RNase L, and pre-miR-21' and (ii) the cleaving capacity of 2 was reduced when RNase L was knocked down win and siRNA (FIGS. 14C-14D).

Figure 7:
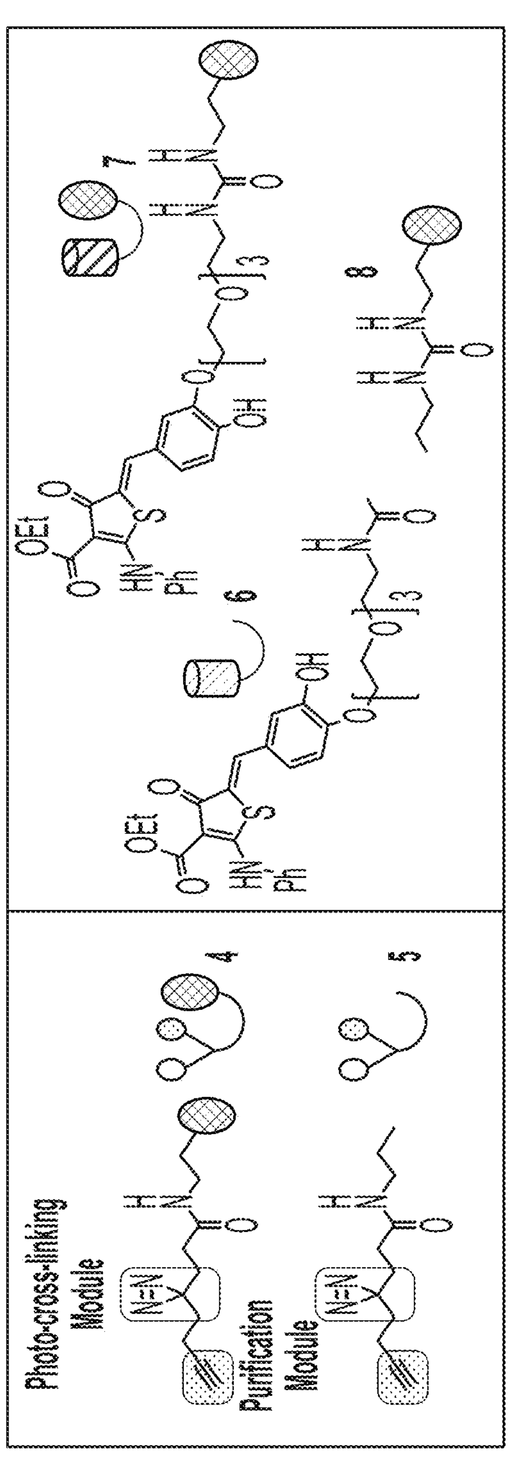
FIG. 7 illustrates chemical structures of the investigation. Chem-CLIP probe 4 comprises the RNA-binding module 1, an alkyne purification module, and a cross-linking diazirine module. Control Chem-CLIP probe 5 lacks RNA-binding module 1. Negative control compound 6 is RIBOTAC 2 without RNA-binding module 1. Negative control compound 7 is a regioisomer of RIBOTAC 2 that has an inactive RNase L recruiter. Control compound 8 is 1 with a urea linker.
Figure 14B:
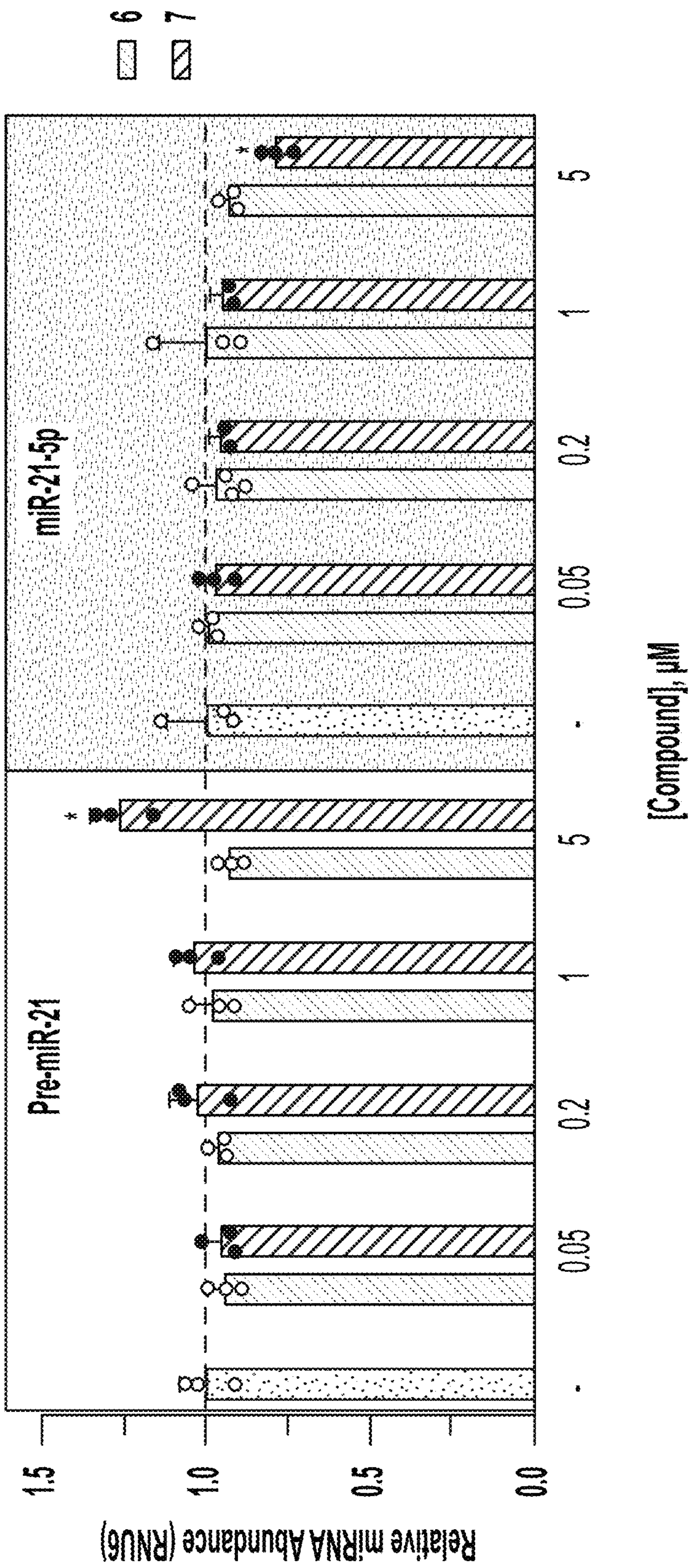
Figure 14C:
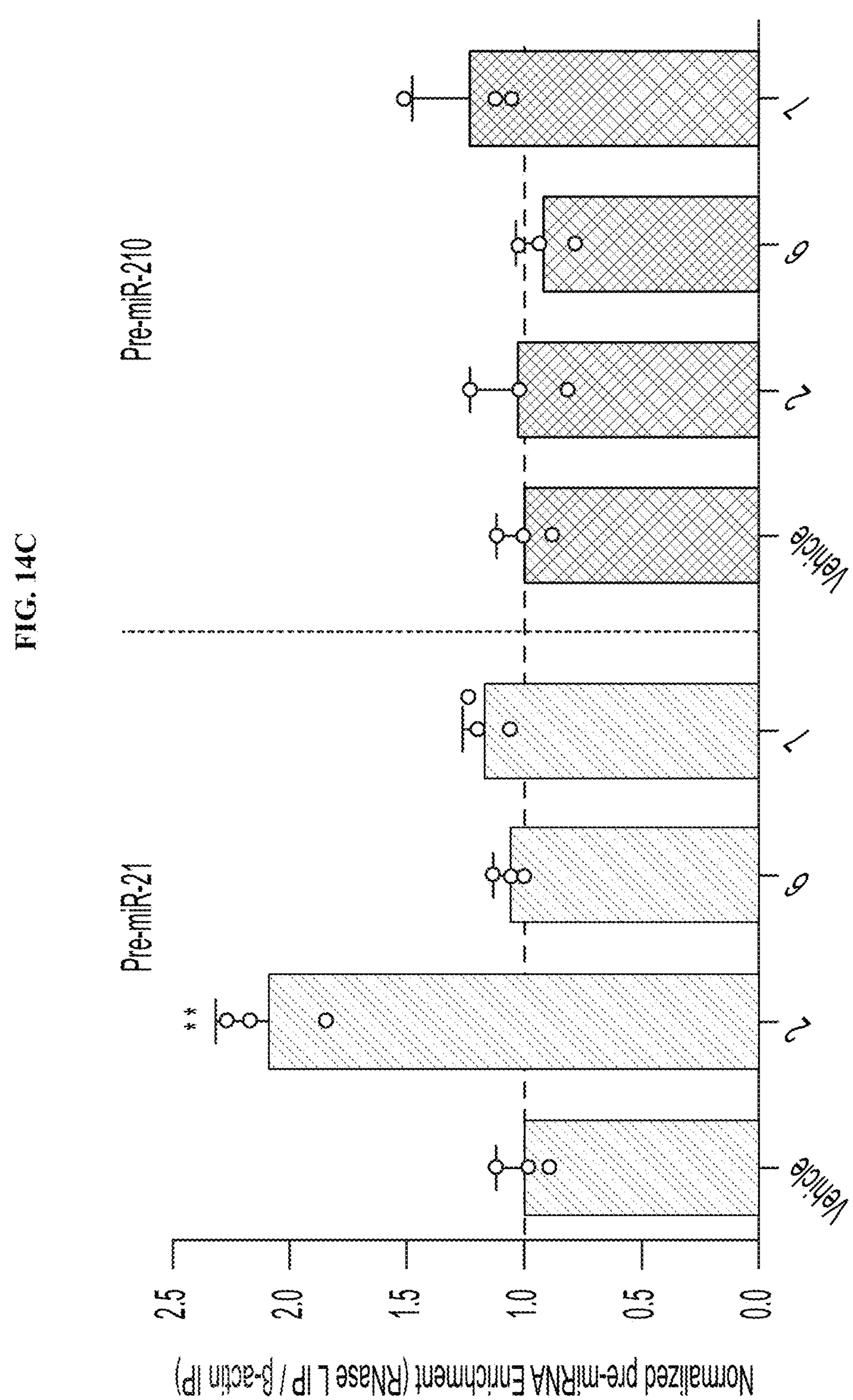
Figure 14D:
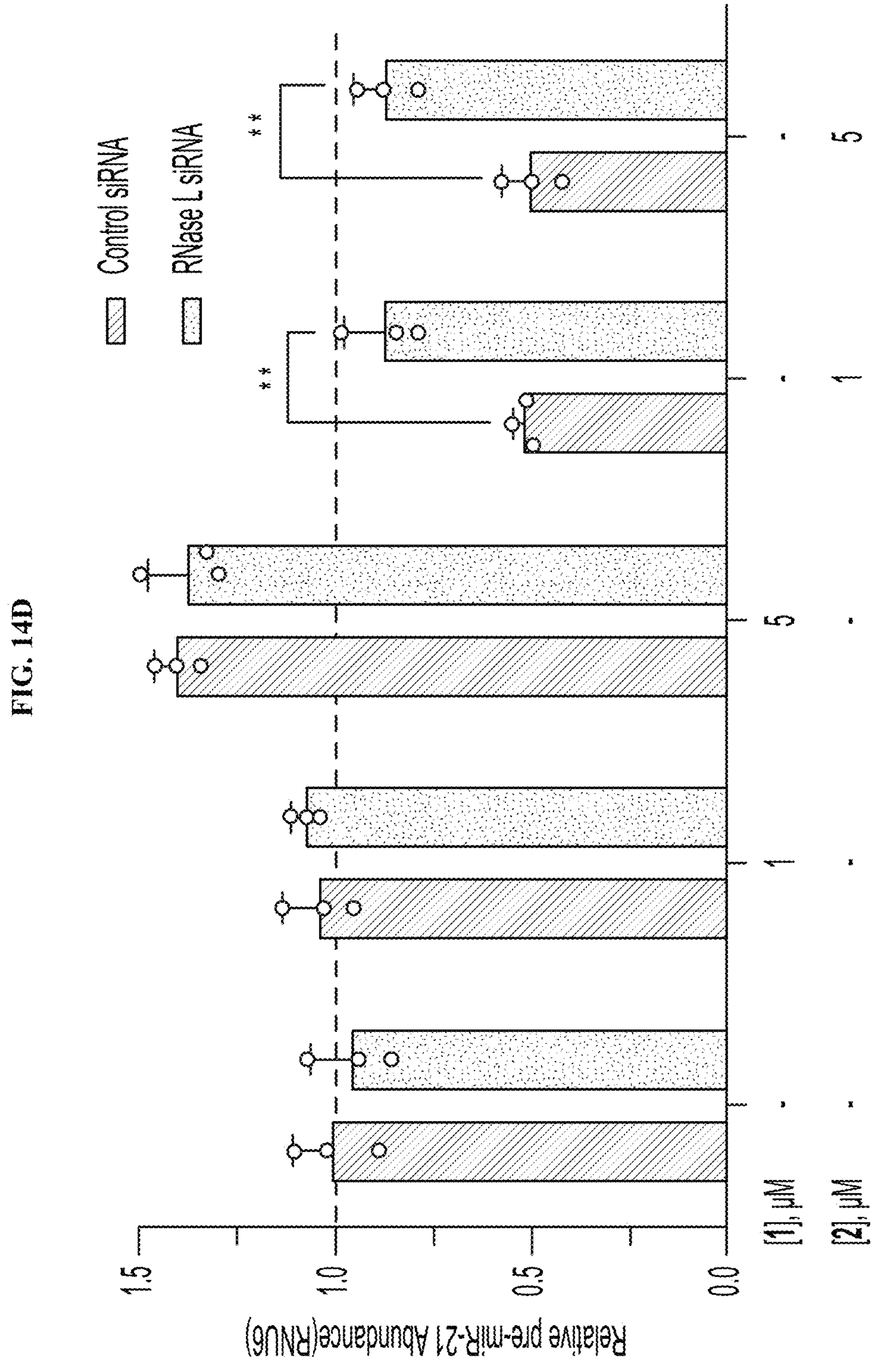
Figure 14E:
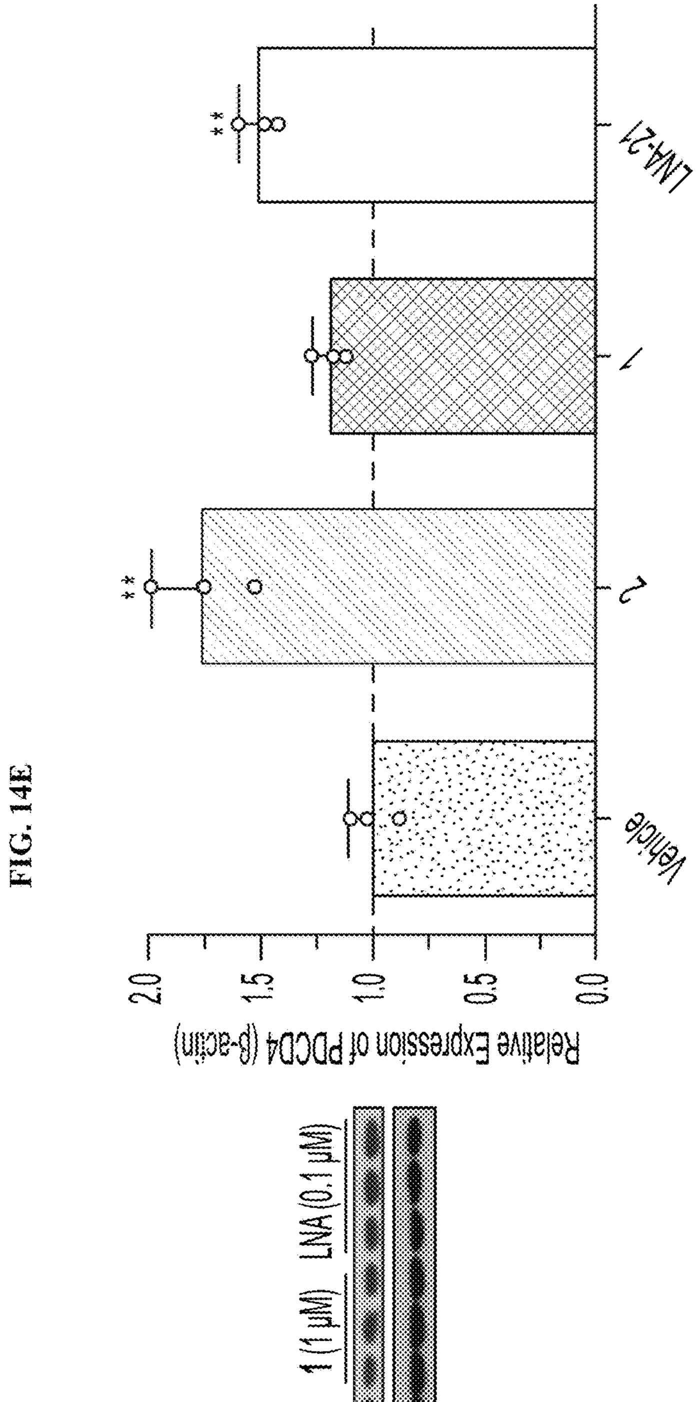

A negative control compound lacking the RNA-binding module of 2 had no effect on miR-21 levels (FIG. 7 and FIG. 14B). Another negative control, a regioisomer of RIBOTAC 2 with an inactive RNase L-recruiting module was also studied (FIG. 7). This compound, as expected, inhibits pre-miR-21 biogenesis, reducing mature miR-21 levels and increasing pre-miR-21 levels, similar to 1 (FIG. 14B). Both negative controls had no enrichment of pre-miR-21 in RNase L antibody immunoprecipitation experiments above (FIG. 14C).

Figures 15A, 15B:
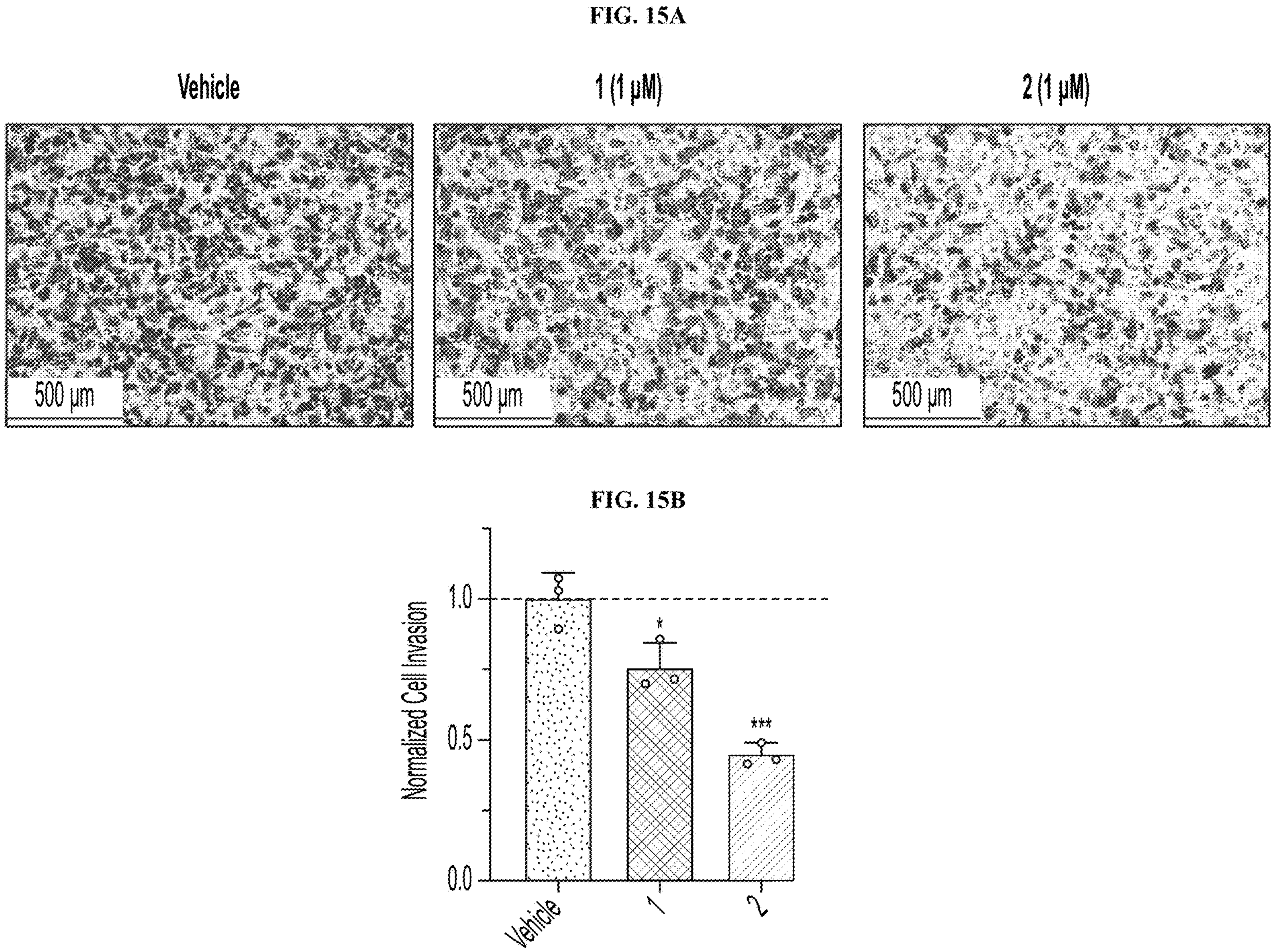
FIGS. 15A-15D illustrate that Compound 2 inhibited the invasive nature (phenotype) of MDA-MB-231 cells and MCF-10A cells forced to overexpress pre-miR-21.
Figure 15C:
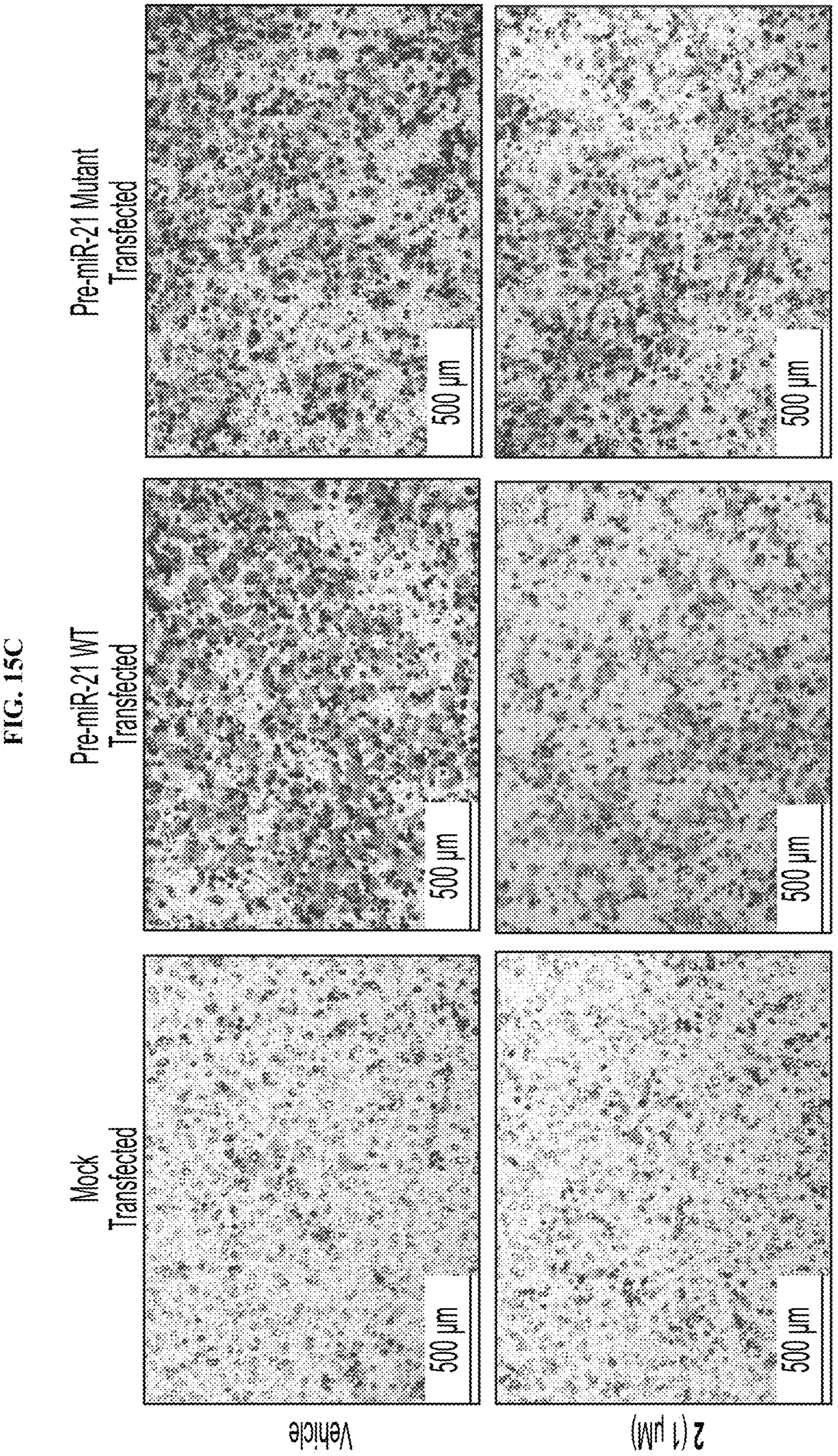
Figure 15D:
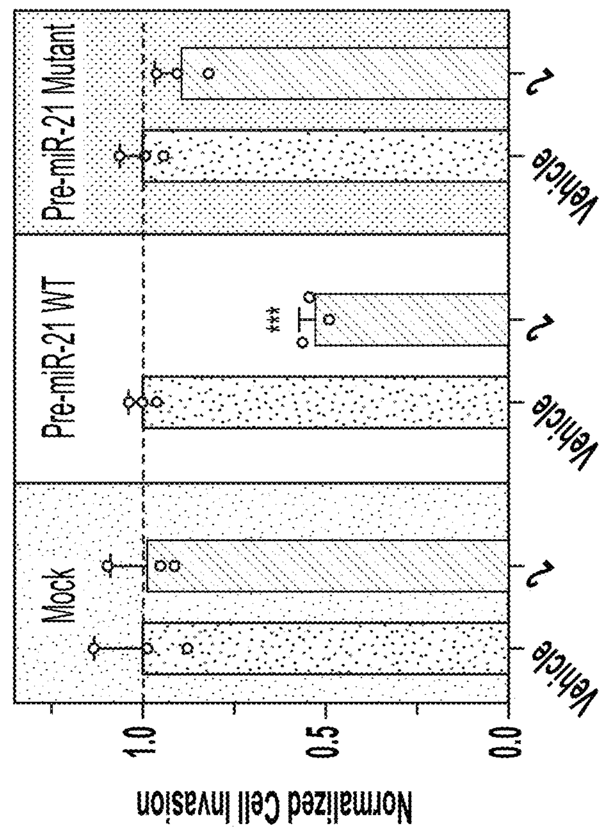
Figure 16A:
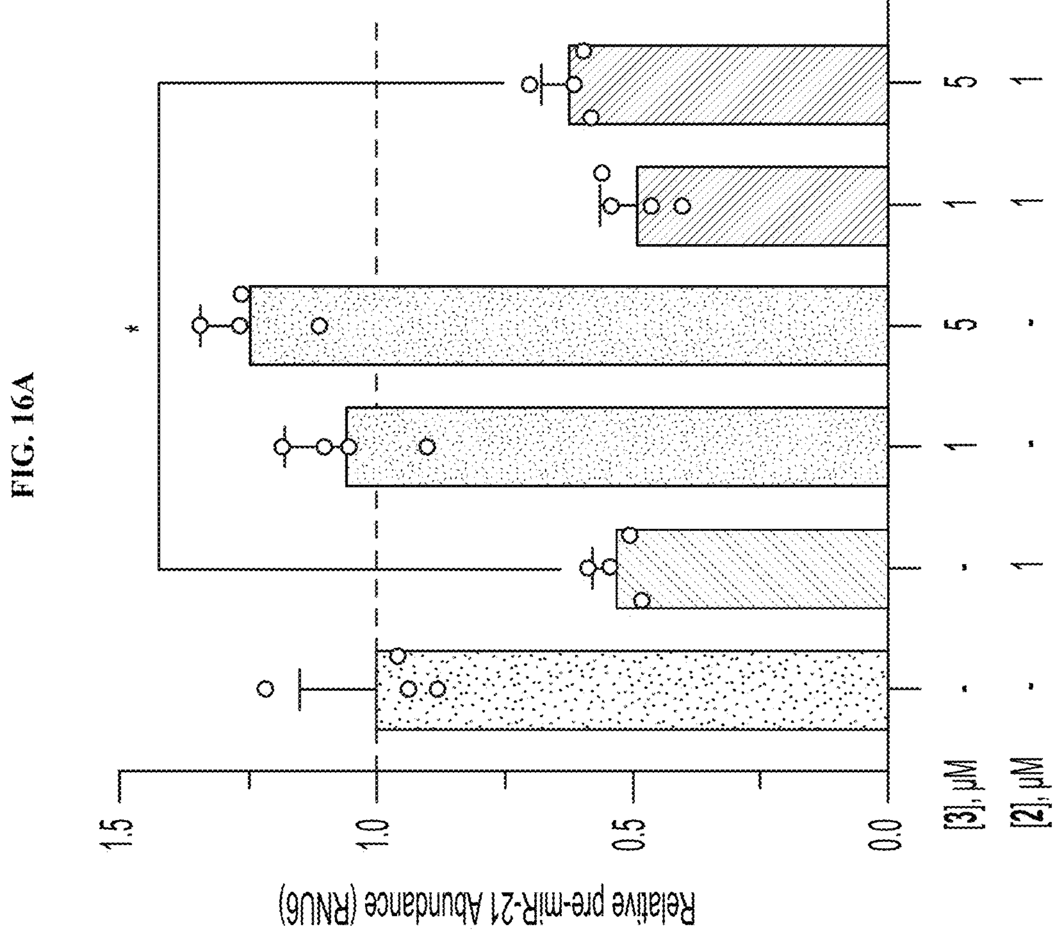
Figure 16B:
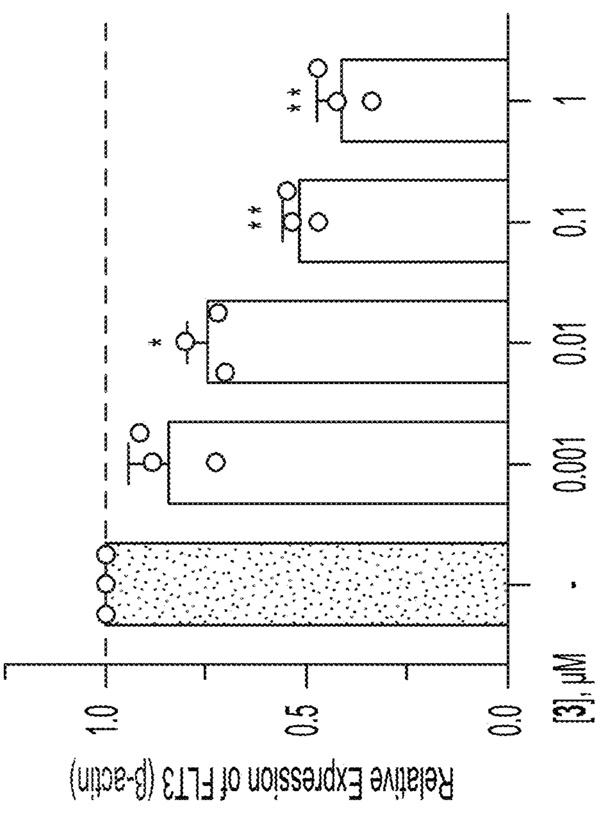
Figure 16D:
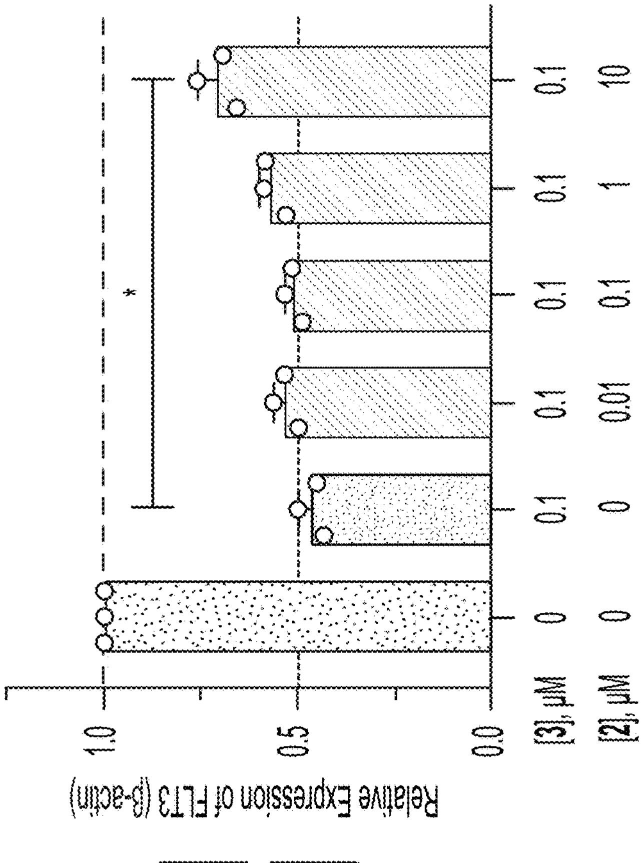
Figure 17A:
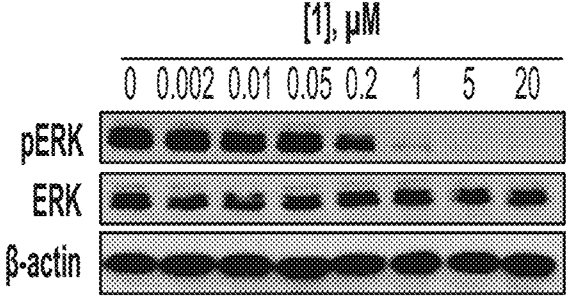
FIGS. 17A-17D illustrate the effect of 1, RIBOTAC 2, and PROTAC 3 on the ERK and phosphorylated ERK levels.
Figure 17B:
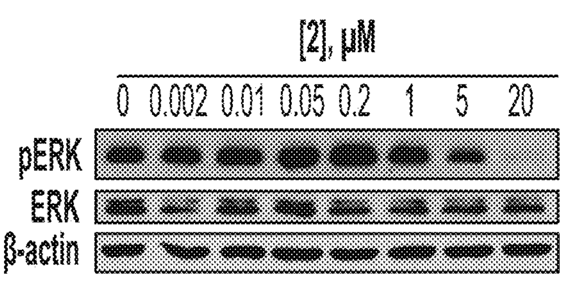
Figure 17C:
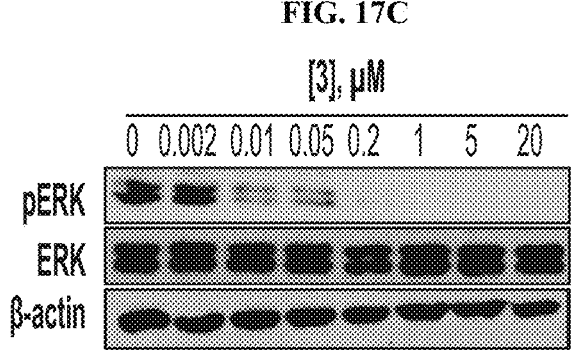
Figure 17D:
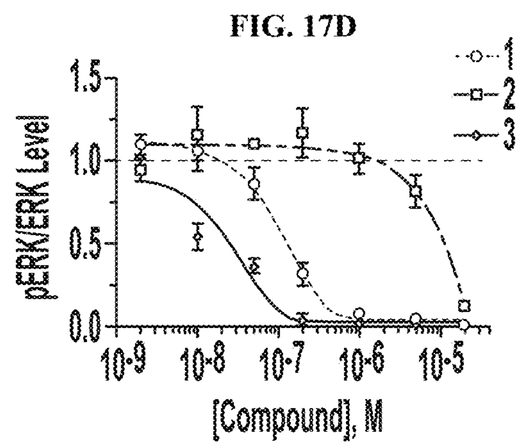

Downstream, ROBOTAC 2 exerted effects similar to those observed for 1 but did so 10-fold more potently, consistent with its more potent reduction of mature miR-21 levels. That is, 2 derepressed PTEN and PDCD4 and reduced the invasive characteristic of MDA-MB-231 cells at 1 μM concentration (FIG. 11C, FIG. 14E, and FIGS. 15A-15B). Further, 2 rescued the invasive phenotype induced in MCF-10A cells by overexpression of pre-miR-21 but had no effect on the invasive phenotype induced by the mutated pre-miR-21 that lacks a 1-binding site (FIGS. 15C-15D). Notably, 2 is more selective than 1, as determined by profiling all miRNAs expressed in MDA-MB-231 cells (FIG. 11B).

Figures 4B, 4C:
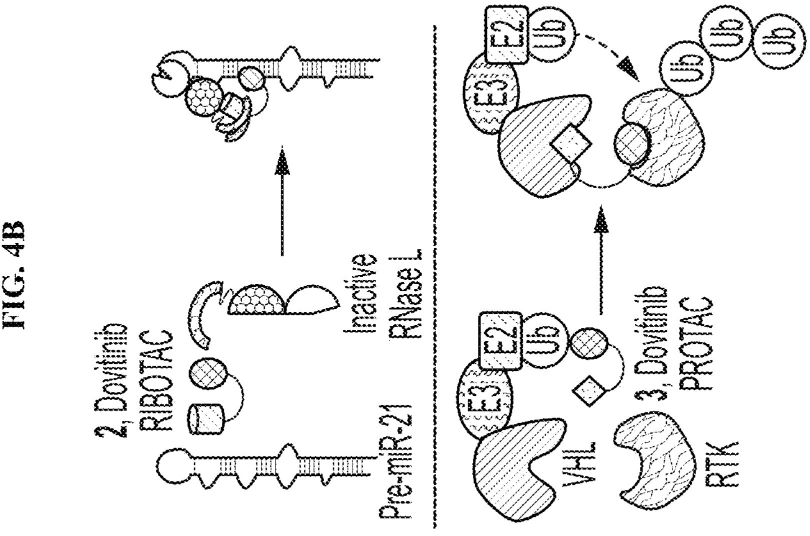

Dovitinib 1 was also converted to PROTAC 3[19] by coupling of a recruiter of E3 ubiquitin ligase to direct the RTK FLT3 to the proteasome (FIGS. 4A-4B). PROTAC 3 reduced the levels of FLT3 with low nanomolar activity and, similar to 1, increased pre-miR-21 levels (FIG. 11A, FIG. 11C, and FIGS. 16A-16B).

Next, experiments were conducted to study whether 1, 2, and 3 functionally inhibit RTK and downstream phosphorylation of extracellular signal-regulated kinase (ERK) and/or miR-21_-regulated proteins in MDA-MB-231 cells. For the canonical protein RTK target, 1, 2, and 3 all inhibited phosphorylation of ERK (pERK), with $IC_{50}$s of 0.1, 10, and 0.02 μM, respectively (FIGS. 17A-17D). Thus, relative to 1, a 5-fold increase of RTK inhibition is observed with PROTAC 3 while a 100-fold decrease of RTK inhibition is observed with RIBOTAC 2 (FIG. 4C). Thus, the selectivity of the miR-21-targeted medicine is shifted by 2,500-fold; 2 is 25-fold more potent for inhibition of miR-21 than 1 and 100-fold less potent than 1 for functional inhibition of RTK (FIG. 4C).

Figures 10B, 10C, 10D, 10E:
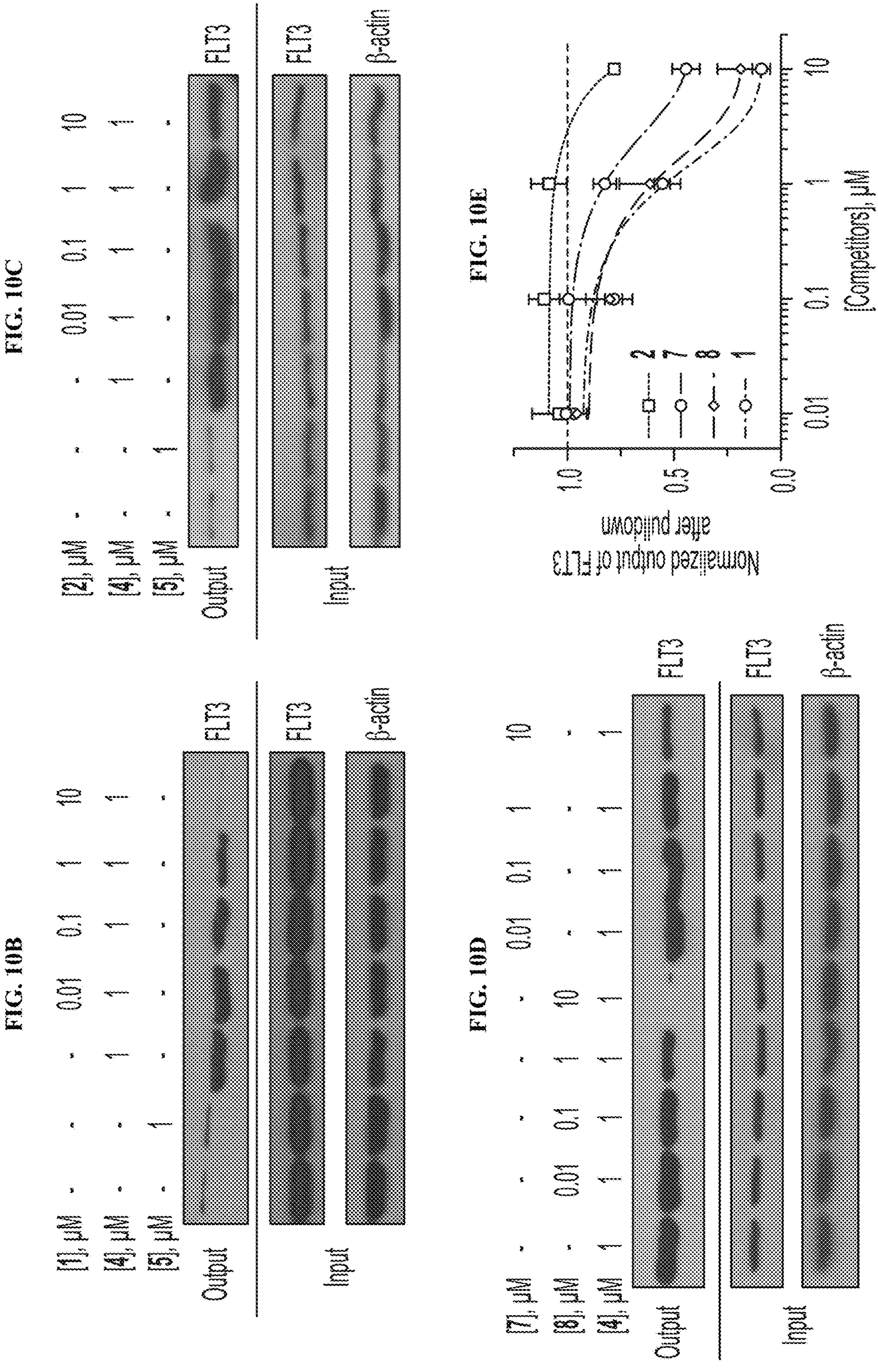

To understand the origin of this remarkable enhancement in selectivity for the RNA target, C-Chem-CLIP experiments were performed to study target engagement of 1, 2, and 3 in MDA-MB-231 cells. The $IC_{50}$s for inhibition of the Chem-CLIP probe for binding to FLT3, are 0.1 and 10 μM for 1 and 2, respectively (FIGS. 10B-10C and FIG. 10E; includes controls). Thus, conversion of a binder into a RIBOTAC decreased cellular protein occupancy by 100-fold. Occupancy accounts for much of the change in selectivity toward RNA while the remaining 25-fold is likely due to the catalytic nature of RIBOTACs[18, 20].

Figure 18B:
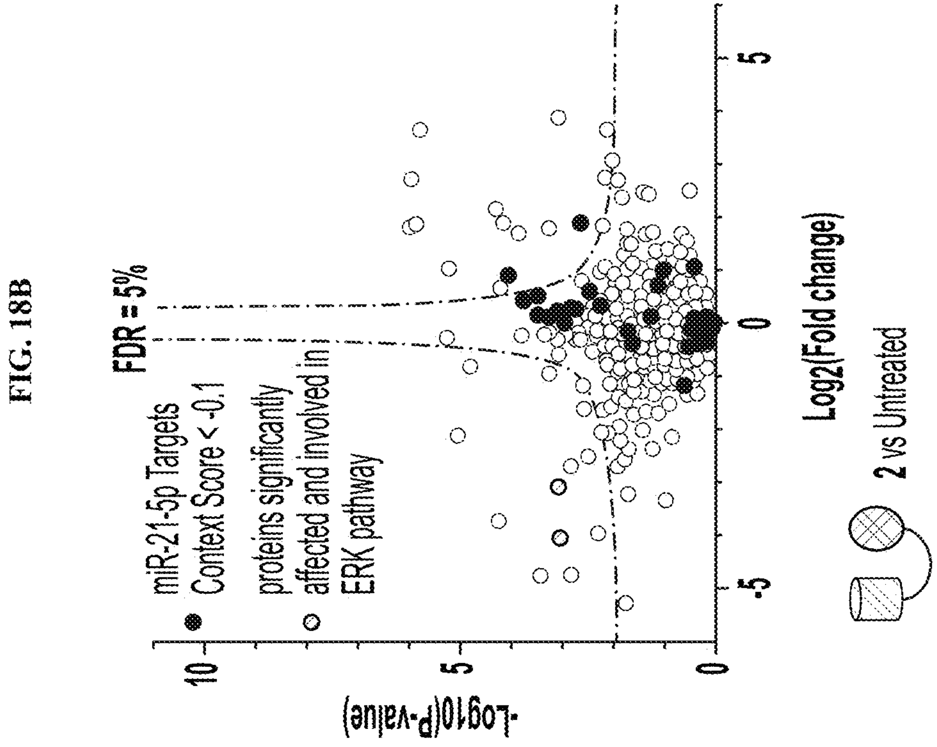
FIGS. 18A-18C illustrate effects of 1, RIBOTAC 2, and LNA-21 on global protein expression in MDA-MB-231 cells.
Figure 18A:
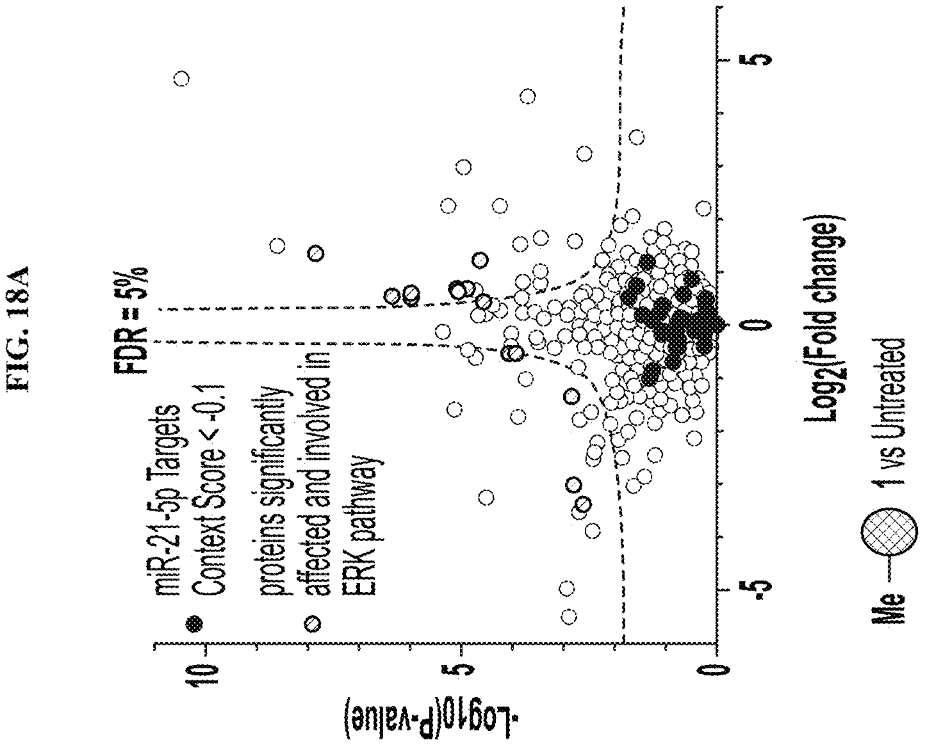
Figure 18C:
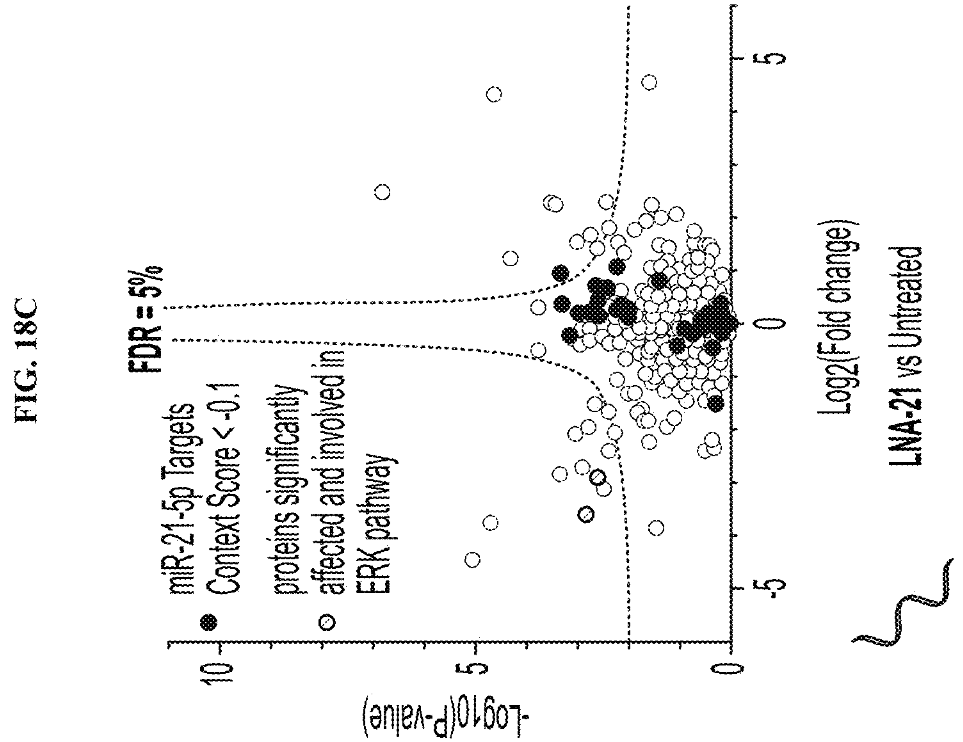
Figure 19:
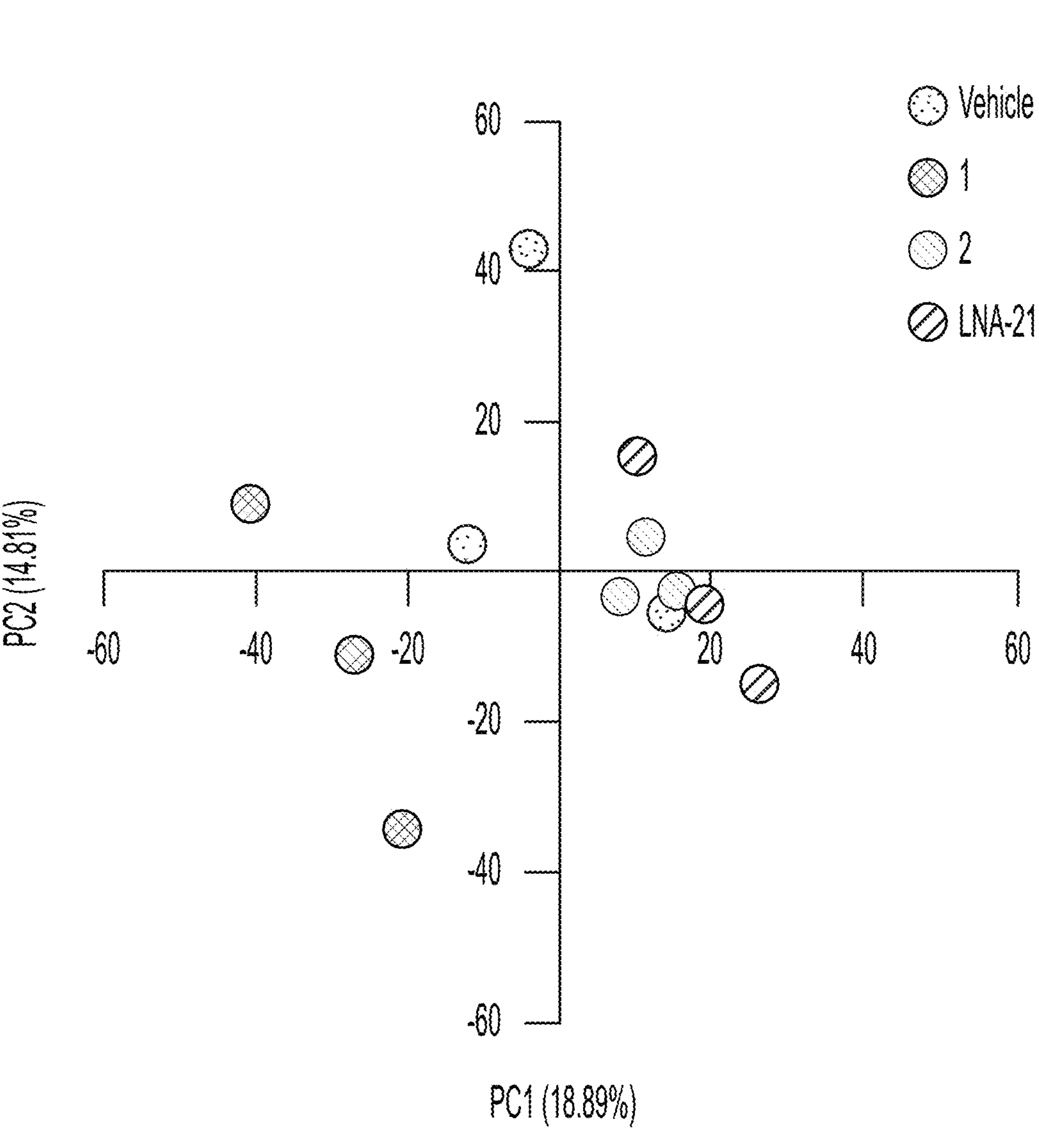
FIG. 19 illustrates PCA of proteome-wide studies reveals samples treated with RIBOTAC 2 are more similar to LNA-21 than 1. PCA plot to visualize differences between experimental groups and batch effects. PCA suggested that samples treated with RIBOTAC 2 are more similar to samples treated with LNA-21 than to samples treated with 1 as expected.
Figures 20A, 20B:
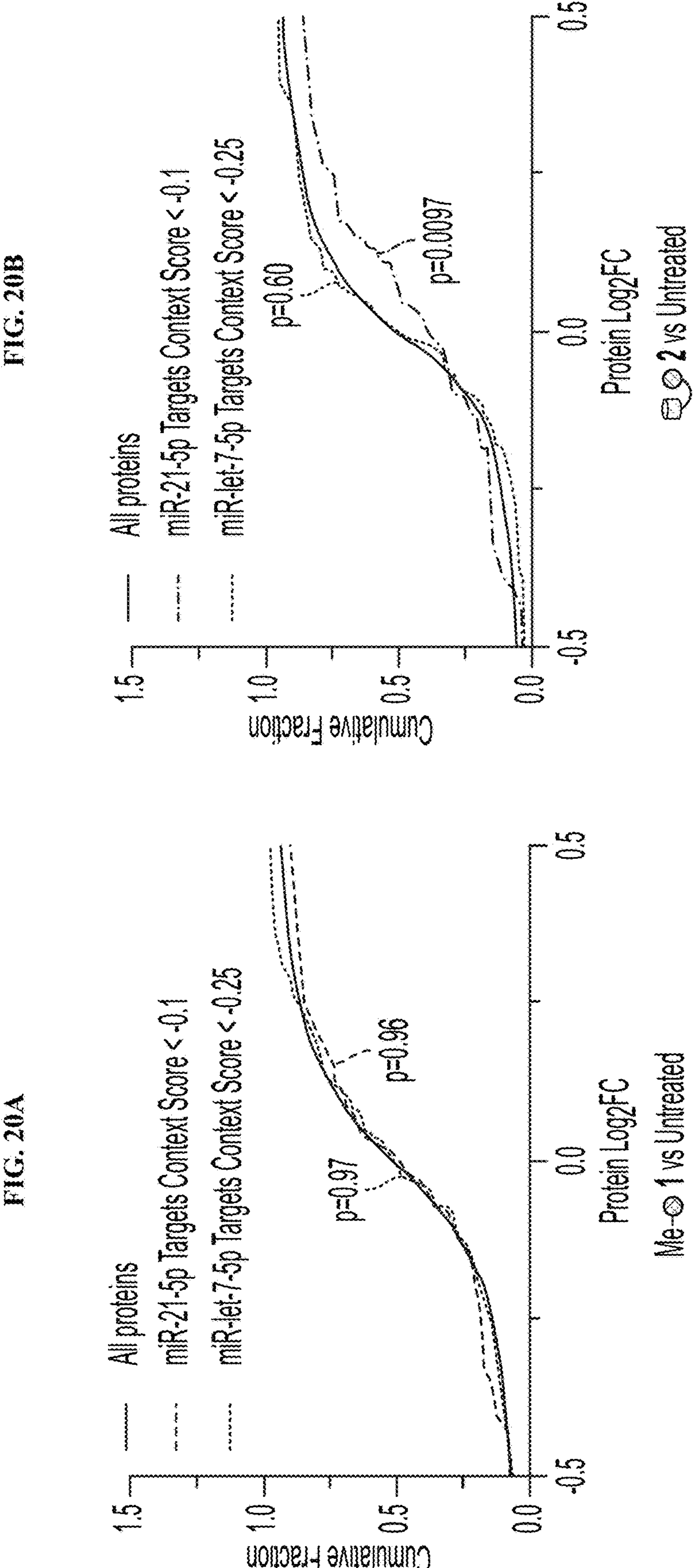
FIGS. 20A-20C illustrate on-target effects of RIBOTAC 2 from global proteomics reveal upregulation of miR-21 target proteins.
Figure 20C:
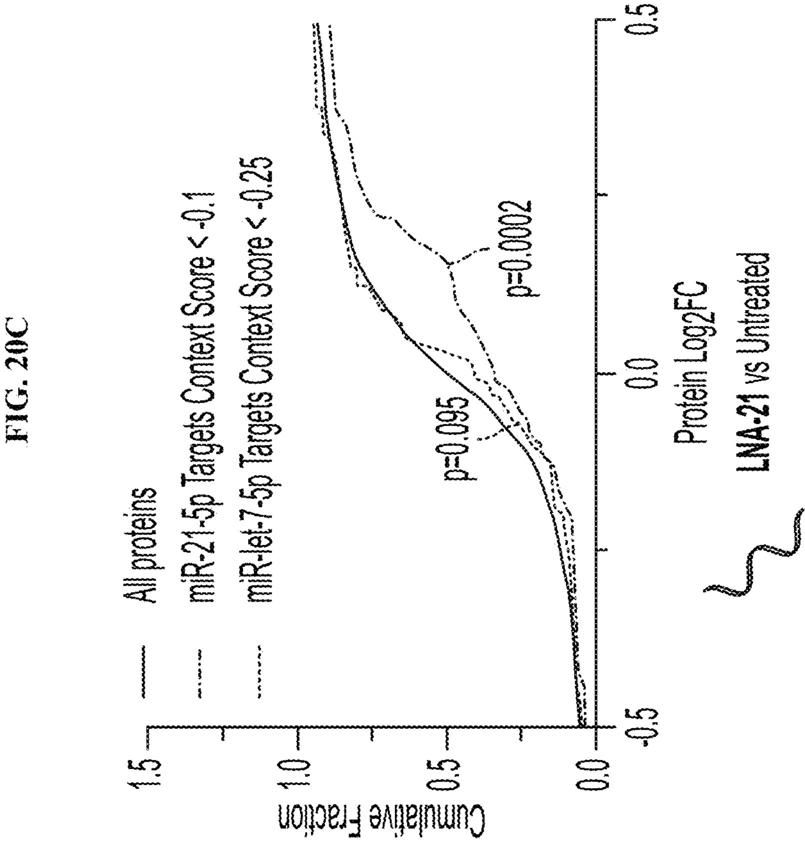

The global effect of 1 was investigated (1 μM, where mature miR-21 levels are not reduced), 2 (1 μM, where mature miR-21 levels are reduced by ~45±9%), and an oligonucleotide that targets miR-21 (LNA-21) on the proteome of MDA-MB-231 cells. Overall, modest effects on the proteome were observed for all three compounds (3000 proteins detected, 15% or less were affected), indicative of selectivity (FIGS. 18A-18C). In 1-treated cells, 46 proteins were significantly affected, 14 of which associated with ERK pathways. For 2 and LNA-21, 28 and 25 proteins were affected, respectively. Principle component analysis (PCA) of the proteome revealed that treatment with RIBOTAC 2 was more similar to treatment with LNA-21 than 1, as expected (FIG. 19). A context score was calculated to quantify the effects of all three compounds on protein levels encoded by mRNAs regulated by miR-21. For both 2 and LNA-21, these proteins are globally upregulated, as expected. Treatment with 1 μM of 1, however, affected RTK-associated pathways but had no effect on miR-21 regulated proteins, as expected based on 1's inability to reduce miR-21 levels at this concentration (FIGS. 20A-20C). Neither treatment with 1 nor 2 affected proteins associated with miR-let-7, selected as a control because of its similar expression level as miR-21. Thus, 2 is specific for miR-21 over RTK and the RIBOTAC strategy allows for easy reprogramming of selectivity for RNA targets.

Figure 5A:
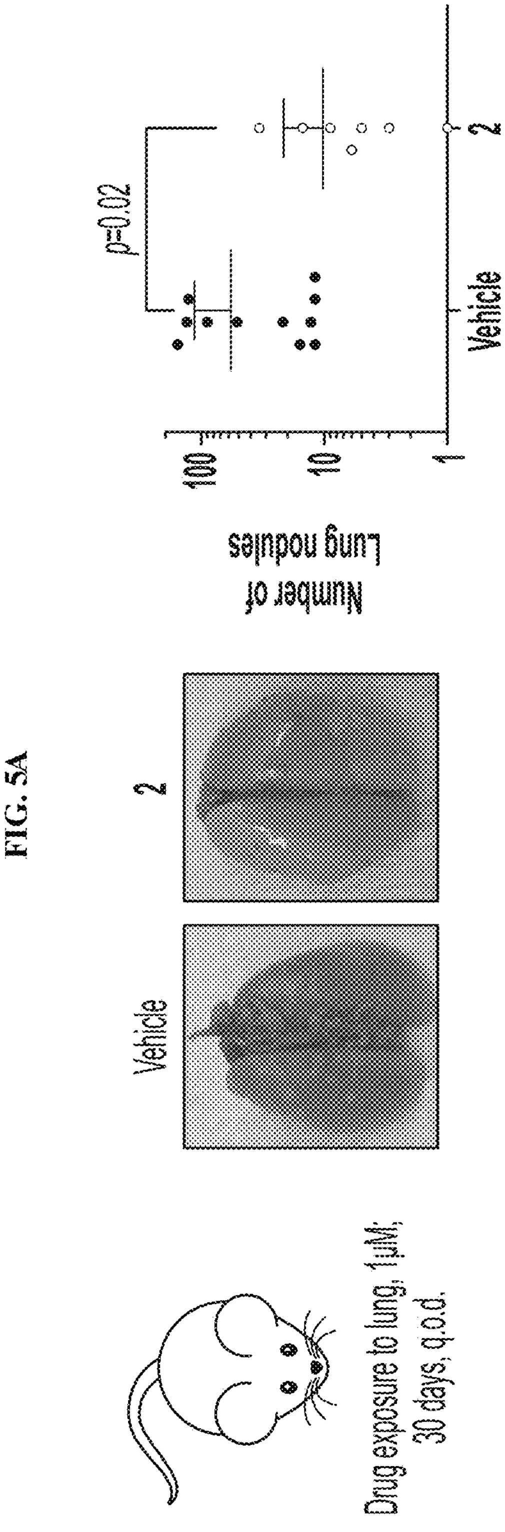
FIGS. 5A-5B illustrate RIBOTAC 2 inhibition of invasion of TNBC cells with reversed selectivity in vivo.
Figure 5B:
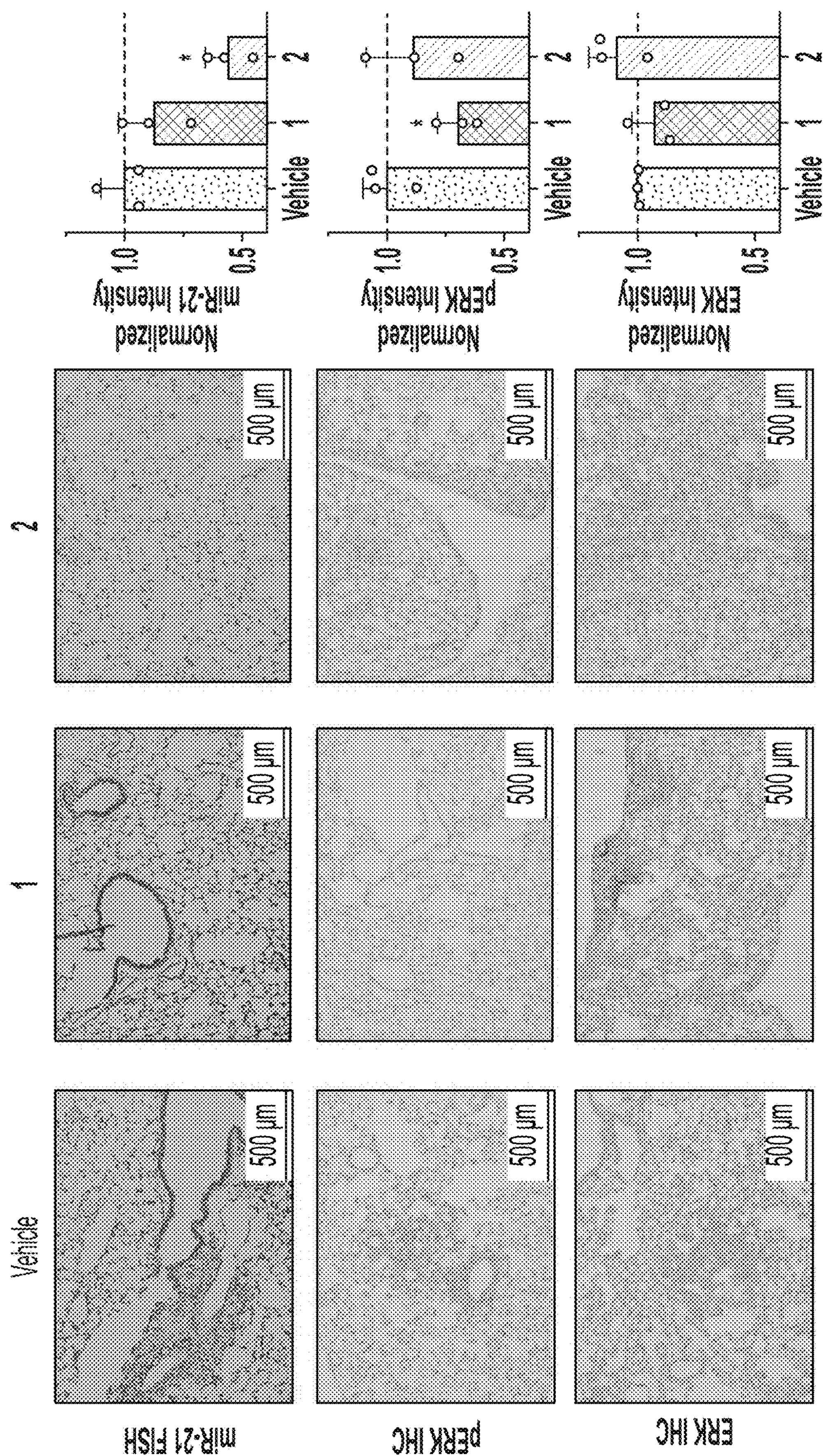
Figures 21A, 21B:
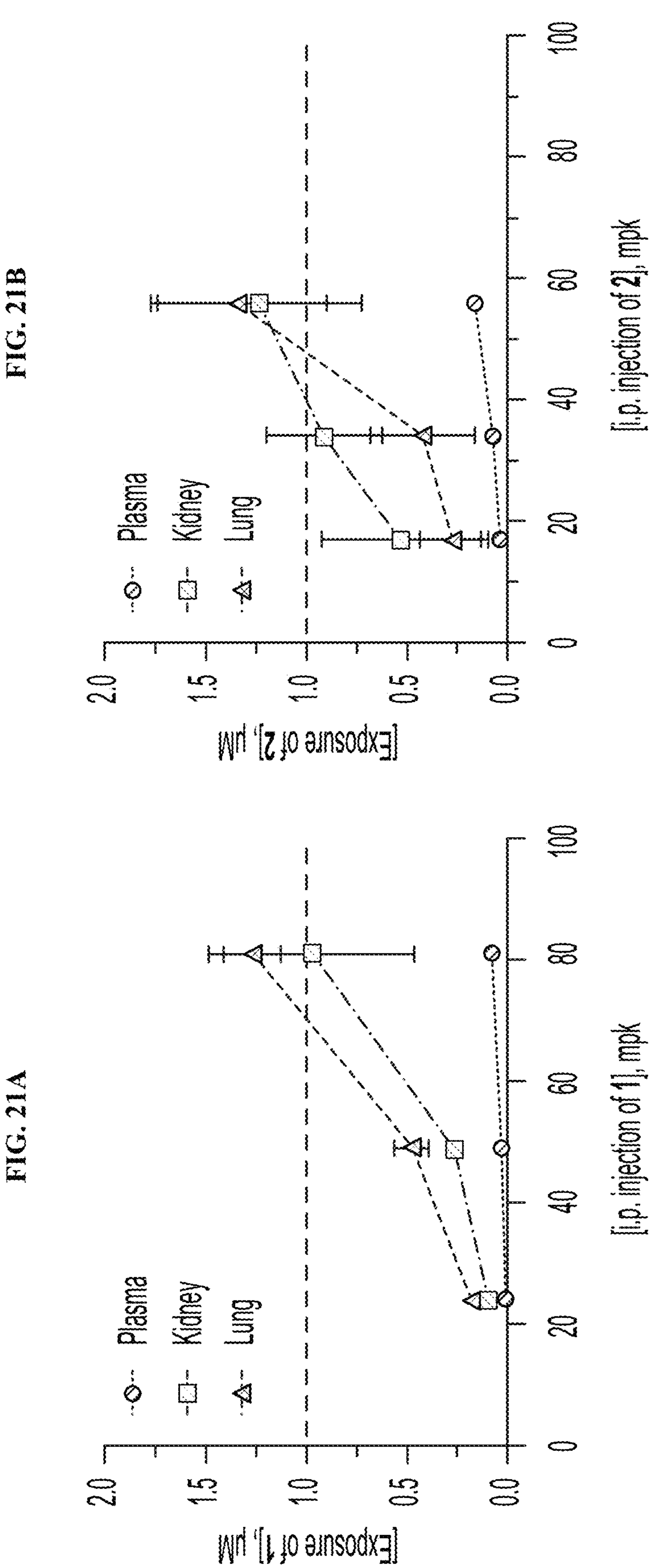
FIGS. 21A-21E illustrate Drug Metabolism and Pharmacokinetics (DMPK) analysis of 1 and RIBOTAC 2 in C57BL/6 mice and weight of xenograft, Alport, and WT mice upon treatment. Mice were i.p. injected with 1 (24, 49 or 81 mg/kg) or 2 (17, 34 or 56 mg/kg).
Figure 21C:
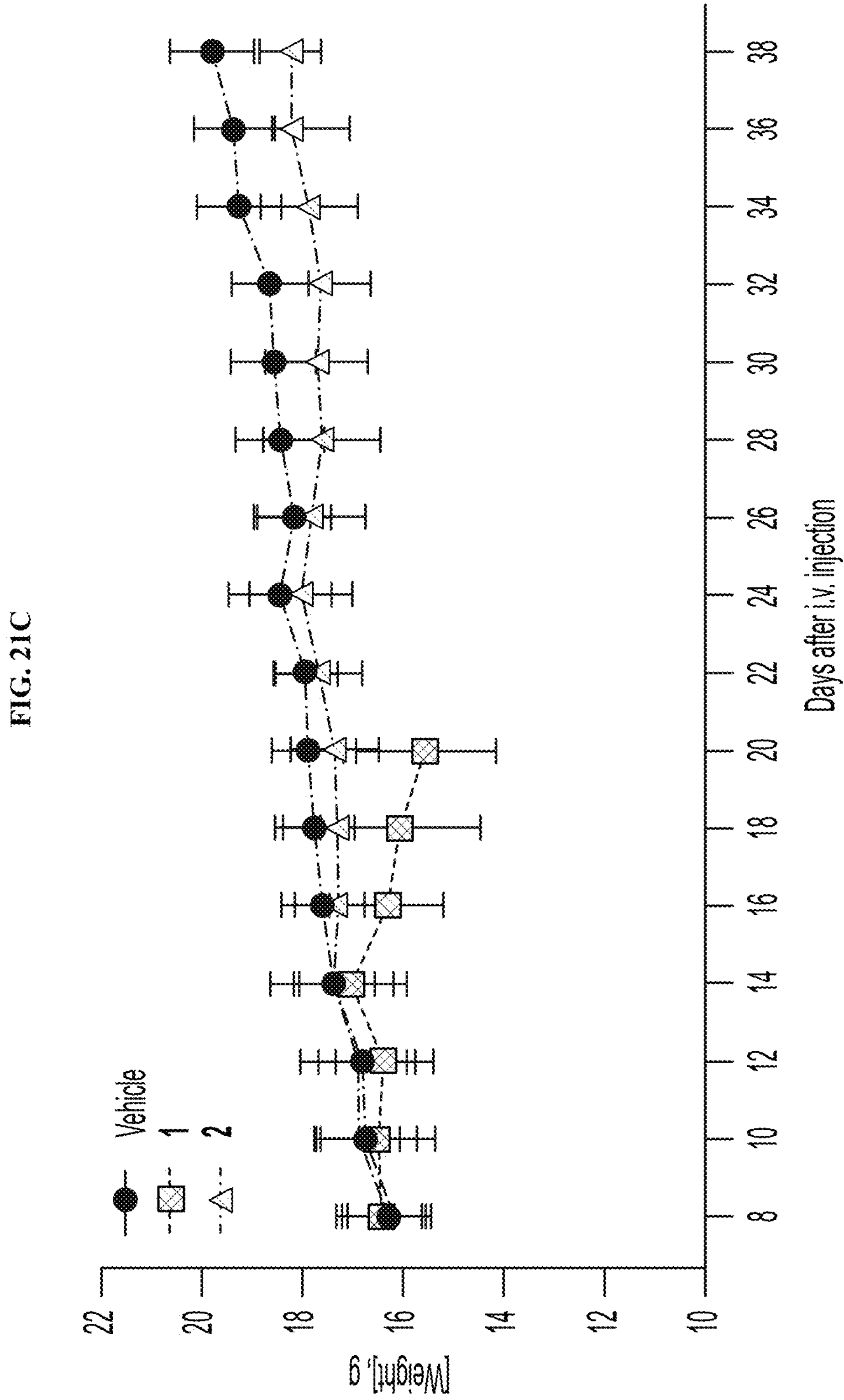
Figure 21D:
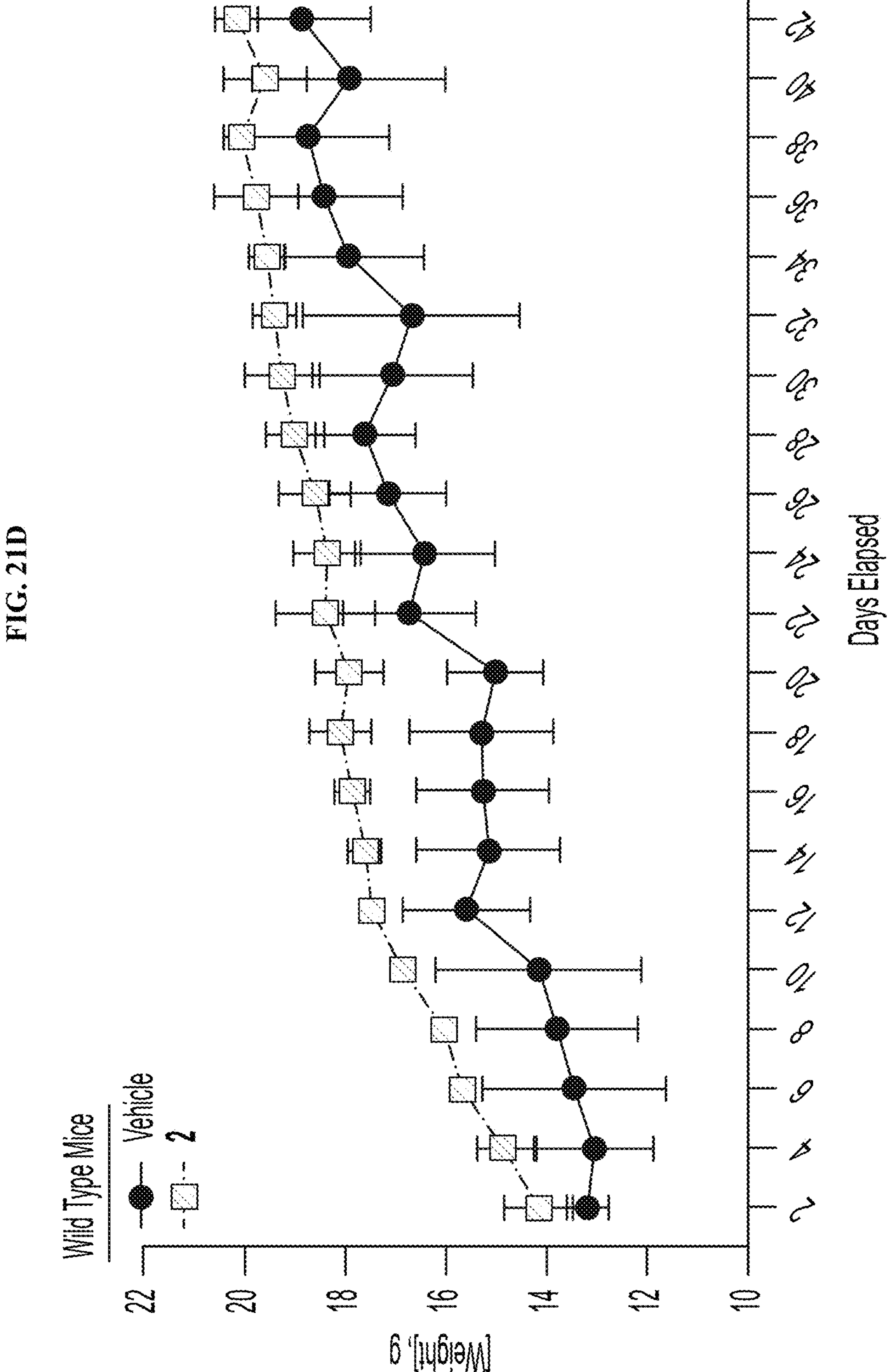
Figure 21E:
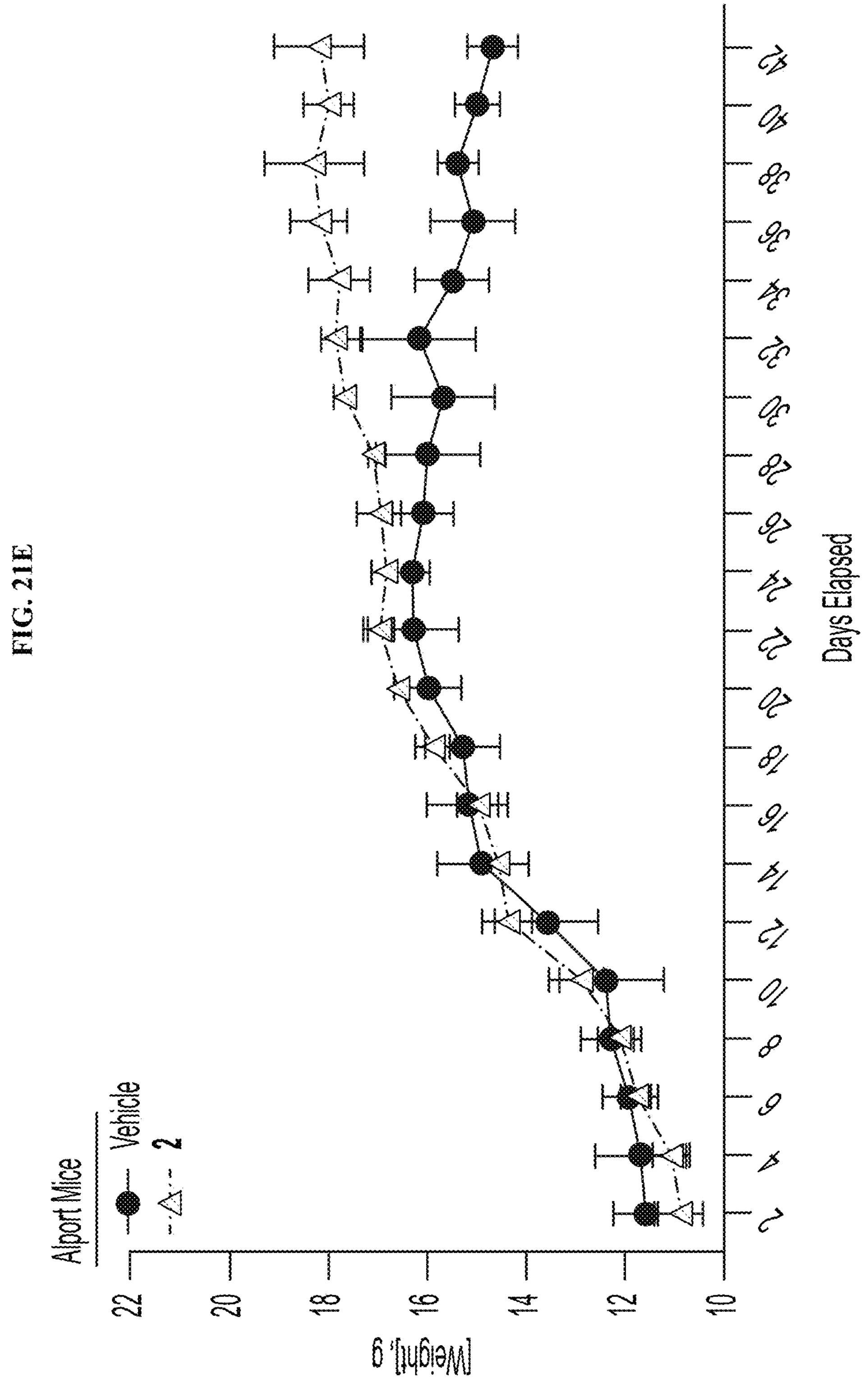
Figure 22:
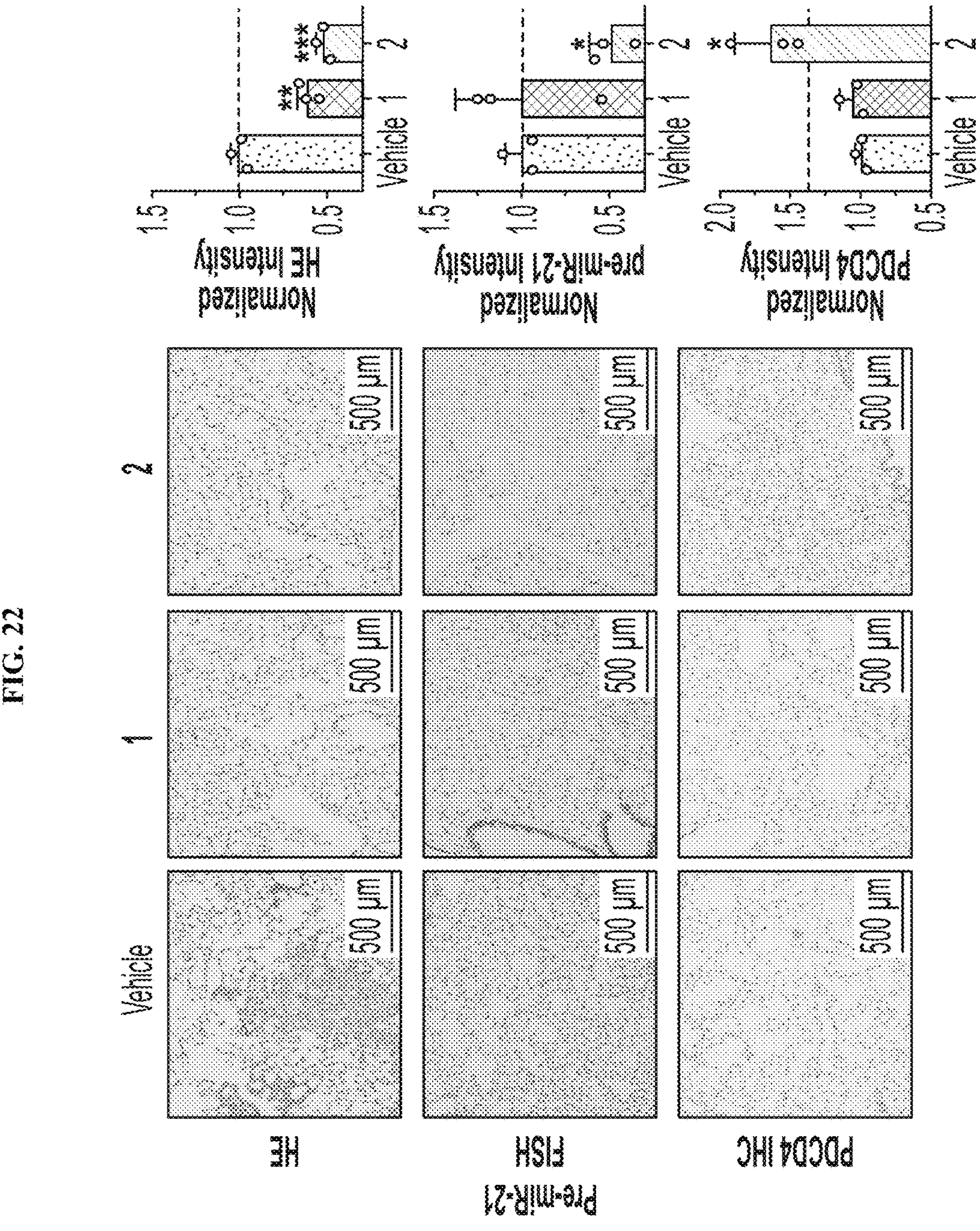
FIG. 22 illustrates that RIBOTAC 2 inhibits MDA-MB-231 metastasis in vivo. From top to bottom: Hematoxylin and eosin (HE) staining, fluorescent in situ hybridization (FISH) staining of pre-miR-21 and immunohistochemistry (IHC) of PDCD4 of lung tissue from mice treated with vehicle, 1, or RIBOTAC 2. Quantifications are shown to the right of each image (n=3). *, $p<0.05$; , $p<0.01$: * $p<0.001$, as tested by a two-tailed Student t-test.

Based on these encouraging results, 2's ability to inhibit the miR-21 mediated metastasis of breast cancer to the lung[21] in a xenograft mouse model was studied. RIBOTAC 2 was administered by intraperitoneal injection at a dose to achieve 1 μM drug exposure in the lung (FIG. 5A, FIGS. 21A-21B). Indeed, breast cancer metastasis was inhibited, as evidenced by the decreased number of lung nodules (FIG. 5A). Lung histological studies showed that treatment led to a decrease in hematoxylin and eosin (HE) staining. Fluorescent in situ hybridization (FISH) showed miR-21 and pre-miR-21 expression were significantly diminished by 2 (FIG. 5B, FIG. 22), while immunohistochemistry (IHC) showed 2 derepressed PDCD4 expression (FIG. 22) and had no effect on ERK or pERK levels (FIGS. 4A-4C). Of note, the mice were also treated with 1 to study its inhibitory effect on metastasis. Dosing was only able to be maintained for 12 days due to toxicity (FIG. 21C). At this time point, 1 did not affect mature miR-21, pre-miR-21, PDCD4, or ERK levels (FIG. 5B, FIG. 22). It did, however, decrease pERK levels, as expected (FIGS. 4A-4C). Altogether, these in vivo studies demonstrate that 1 can indeed be repurposed by conversion into RIBOTAC 2, a selective miR-21 inhibitor.

Alport Syndrome (AS) is a genetically defined kidney disease where miR-21 inhibition has therapeutic potential[10]. AS patients have a mutation in COL genes[22] and a mouse model for AS with a knockout of the COL4A3 gene ($Col4a3^{-/-}$) has been developed[23]. It displays various aspects of AS including loss of kidney function and histological changes found in patients.

Figures 6A, 6B:
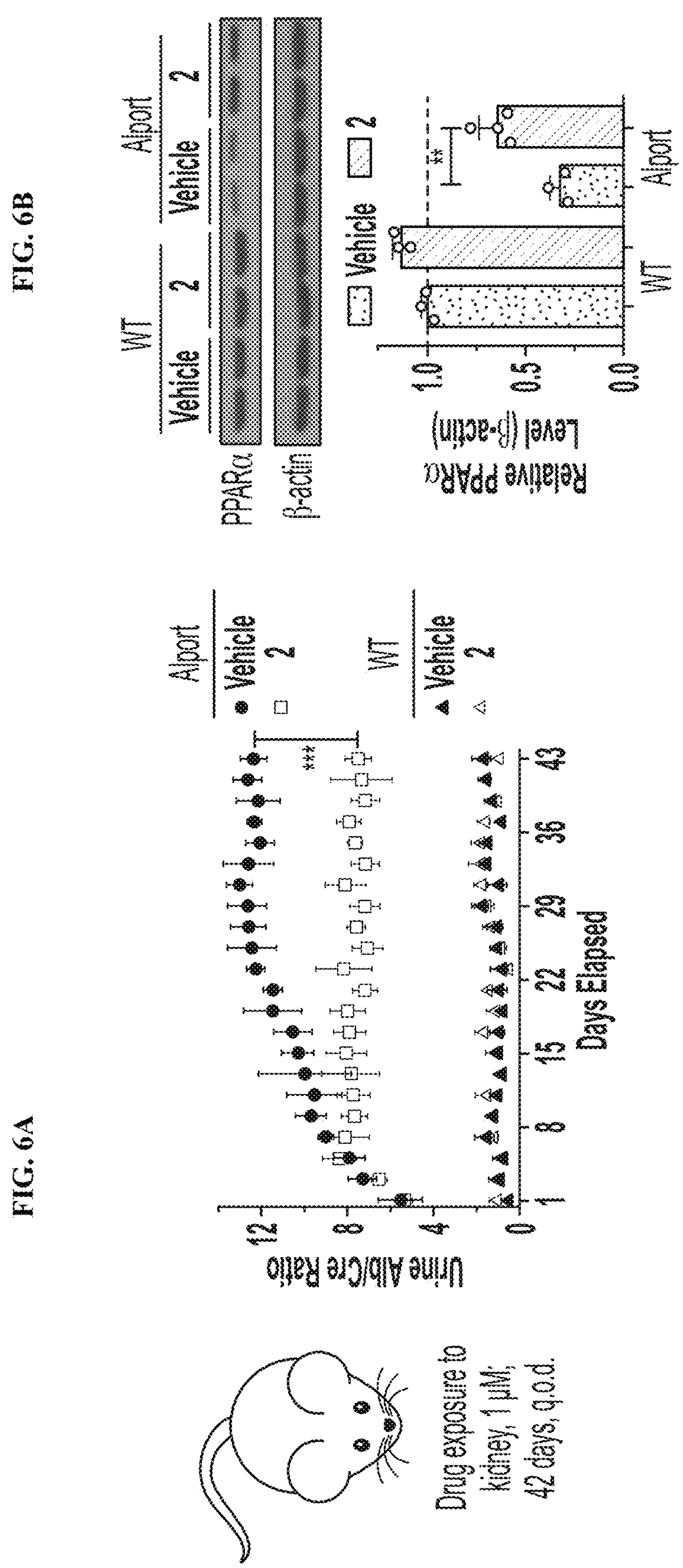
FIGS. 6A-6D illustrate RIBOTAC 2 prevention of progression of disease-associated nephropathy in Alport mice by inhibiting miR-21 biogenesis.
Figures 6C, 6D:
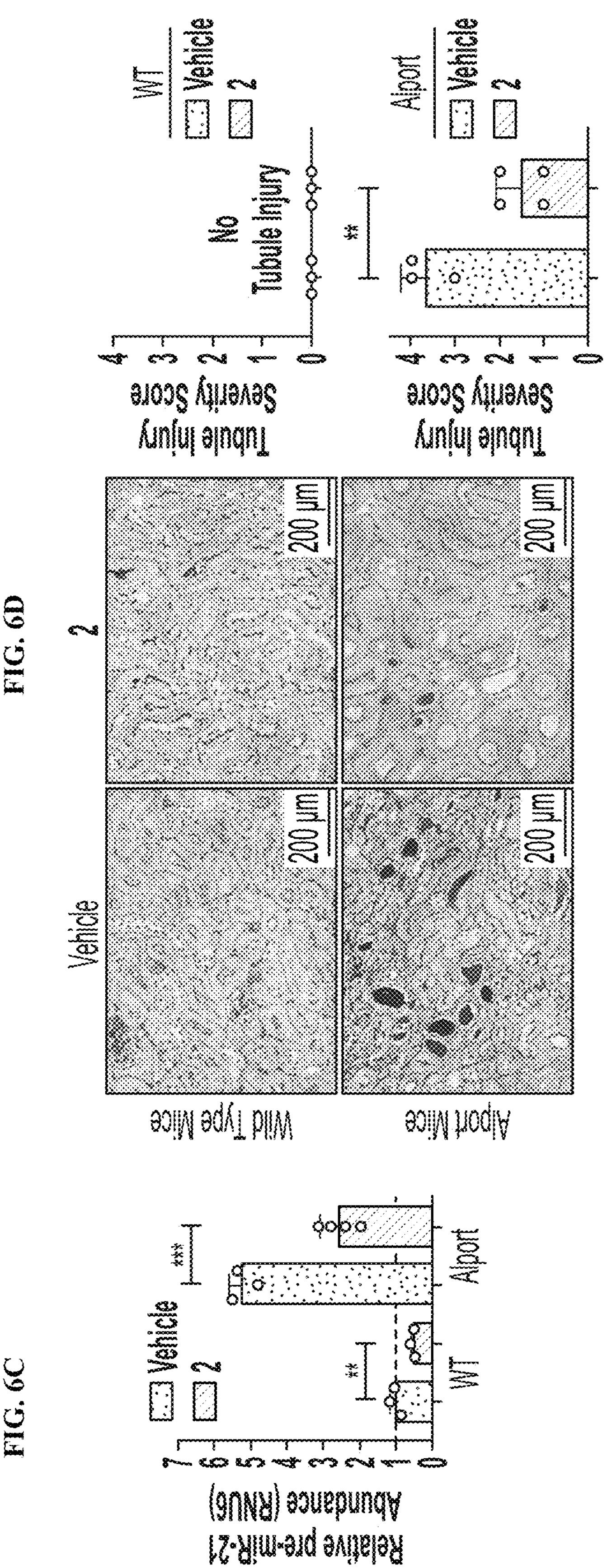
Figure 23:
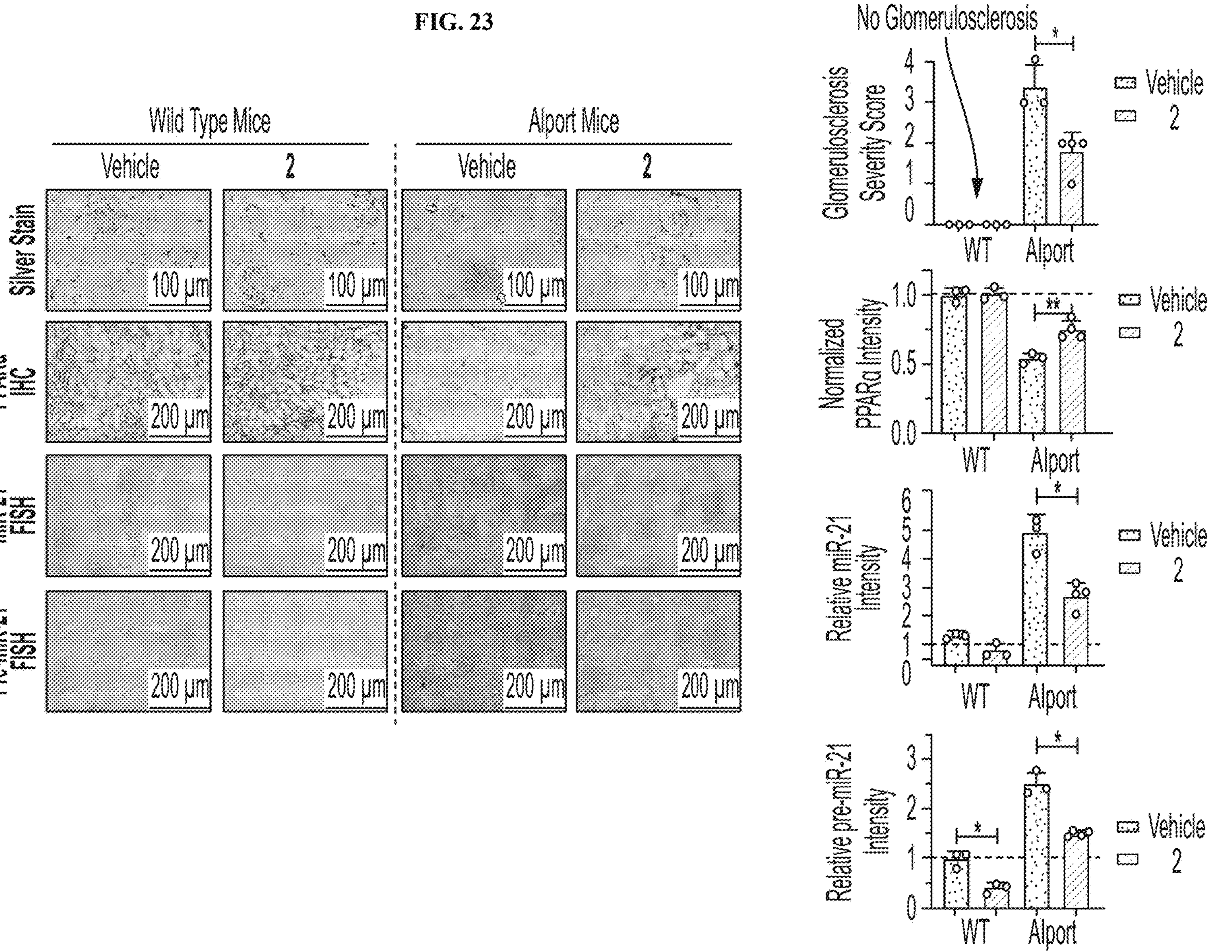
FIG. 23 illustrates that RIBOTAC 2 prevents glomerulosclerosis and tubular atrophy in kidney of Alport mice. From top to bottom: silver methenamine-stained images, with glomerulosclerosis highlighted with arrows; IHC staining of PPARα; FISH staining of miR-21 and pre-miR-21. Glomerulosclerosis severity was scored from 0 to 4 by extent of sclerosis as previously described[13] where 0 is no glomerulosclerosis as observed in wild type mice and 4 is most severe, for examples as observed in untreated Alport mice. Quantifications are shown to the right of each image (for vehicle- and 2-treated WT mice, n=3; for vehicle-treated Alport mice, n=3; for 2-treated Alport mice, n=4). *, $p<0.05$; **, $p<0.01$, as tested by a two-tailed Student t-test.
Figure 24:
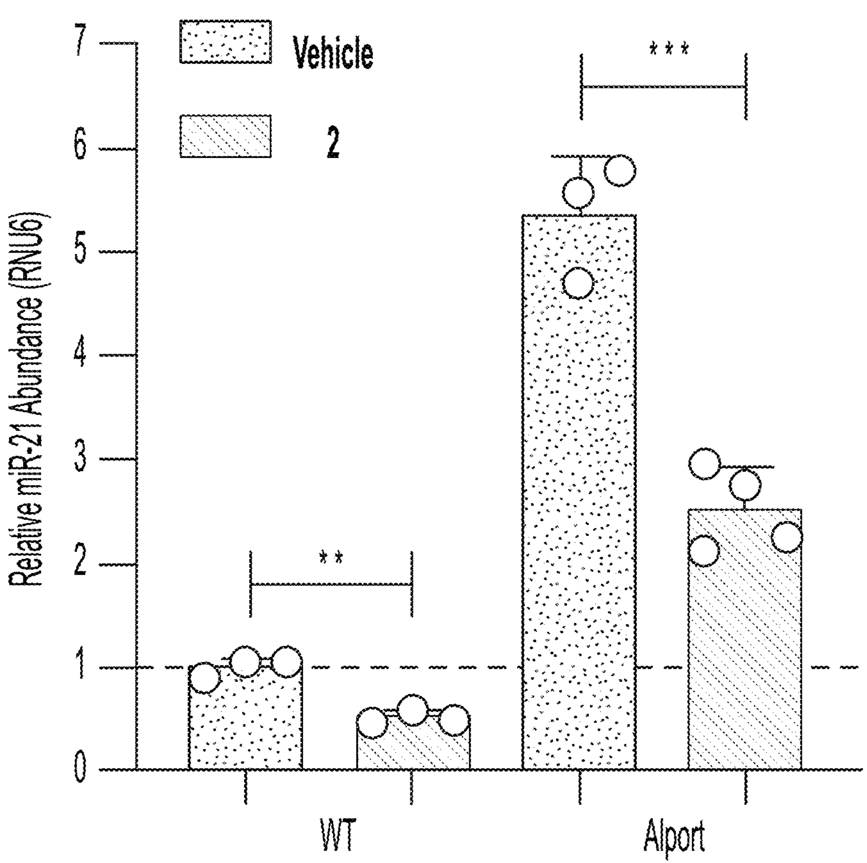
FIG. 24 illustrates that RIBOTAC 2 decreased miR-21 levels in kidneys of both WT and Alport mice. Mature miR-21 levels were measured by RT-qPCR (for vehicle- and 2-treated WT mice, n=3; for vehicle-treated Alport mice, n=3; for 2-treated Alport mice, n=4); , $p<0.01$;  $p<0.001$, as tested by a two-tailed Student t-test.

Ribotac-Dovitinib 2 was delivered to an AS mouse model and measured its effect on kidney function by monitoring urine albumin normalized to urine creatinine levels (FIG. 6A). After one week of treatment, albumin levels were stabilized indicating improved kidney function (FIG. 6A). Kidneys from 2-treated and vehicle-treated AS mice were harvested and analyzed, showing reduced levels of mature and pre-miR-21 and enhanced levels of PPARα protein levels, a target repressed by miR-21 (FIGS. 6B-6C, FIG. 23 and FIG. 24)[10]. Histological studies showed that disease-associated phenotypes were ameliorated by 2; tubulointerstitial pathology and glomerulosclerosis were significantly reduced (FIG. 6D, FIG. 23). Thus, in a non-cancerous and currently untreatable genetically defined kidney disease, Dovitinib has been repurposed into a pre-miR-21 degrader that rescues AS molecular defects and phenotypes.

Mechanism of Action and Medical Treatment

In certain embodiments, the invention is directed to methods of inhibiting, suppressing, derepressing and/or managing biolevels of the miRNA-21 and/or the corresponding pri-miR-21 and pre-miR-21as well as these RNA entities present in oncologic cell lines and in animals and humans having such oncologic cells and present in neoplastic cell lines and in animals and humans. The Compounds 2 and 3 as embodiments of the invention for use in the methods disclosed herein bind to the above identified RNA entities as well as bind to the above identified cell lines, animals and humans.

Embodiments of the Compounds applied in methods of the invention and their pharmaceutical compositions are capable of acting as "inhibitors", suppressors and or modulators of the above identified RNA entities which means that they are capable of blocking, suppressing or reducing the expression of the RNA entities. An inhibitor can act with competitive, uncompetitive, or noncompetitive inhibition. An inhibitor can bind reversibly or irreversibly.

The compounds useful for methods of the invention and their pharmaceutical compositions function as therapeutic agents in that they are capable of preventing, ameliorating, modifying and/or affecting a disorder or condition. The characterization of such compounds as therapeutic agents means that, in a statistical sample, the compounds reduce the occurrence of the disorder or condition in the treated sample relative to an untreated control sample, or delays the onset or reduces the severity of one or more symptoms of the disorder or condition relative to the untreated control sample.

The ability to prevent, ameliorate, modify and/or affect in relation to a condition, such as a local recurrence (e.g., pain), a disease known as an oncologic disease such as but not limited to breast cancer and/or prostate cancer or any other neoplastic and/or oncologic disease or condition, especially having etiology similar to breast and/or prostate cancer and/or non-small cell lung cancer as well as hematologic oncologic disease may be accomplished according to the embodiments of the methods of the invention and includes administration of a composition as described above which reduces, or delays or inhibits or retards the oncologic medical condition in a subject relative to a subject which does not receive the composition.

Exemplary forms of cancer which may be treated by the methods of the invention using the compositions of Compounds 2 and 3 of the invention and their pharmaceutical compositions include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer.

Additional exemplary forms of cancer which may be treated by the methods of the invention include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer.

The compounds of the present invention and their salts and solvates, thereof, may be employed alone or in combination with other therapeutic agents for the treatment of the diseases or conditions associated with pre-miR-21 bioactivity.

In various embodiments, Compounds of the invention may be used to treat neoplastic growth, angiogenesis, infection, inflammation, immune-related diseases, ischemia and reperfusion injury, multiple sclerosis, rheumatoid arthritis, neurodegenerative conditions, or psoriasis.

Neoplastic growth may include cancer. Suitably, the present invention relates to a method for treating or lessening the severity of a cancer selected from: brain (gliomas), glioblastomas, breast, Wilm's tumor, Ewing's sarcoma, rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T cell leukemia, chronic myelogenous leukemia, chronic lymphocytic leukemia, Hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In various embodiments, the cancer is selected from brain cancer (gliomas), glioblastomas, breast cancer, colon cancer, head and neck cancer, kidney cancer, lung cancer, liver cancer, melanoma, ovarian cancer, pancreatic cancer, prostate cancer, sarcoma and thyroid cancer.

In various embodiments, the cancer is a solid tumor. In various embodiments, the cancer is selected from multiple myeloma, metastatic breast cancer, non-small cell lung cancer, prostate cancer, advanced colorectal cancer, ovarian or primary peritoneal carcinoma, hormone refractory prostate cancer, squamous cell carcinoma of the head and neck, metastatic pancreatic adenocarcinoma, gastroesophageal junction or stomach, or non-Hodgkin's lymphoma.

The compounds of the invention and their pharmaceutical compositions are capable of functioning prophylactically and/or therapeutically and include administration to the host/patient of one or more of the subject compositions. If it is administered prior to clinical manifestation of the unwanted condition (e.g., disease or other unwanted state of the host animal/patient) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The compounds of the invention and their pharmaceutical compositions are capable of prophylactic and/or therapeutic treatments. If a compound or pharmaceutical composition is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). As used herein, the term "treating" or "treatment" includes reversing, reducing, or arresting the symptoms, clinical signs, and underlying pathology of a condition in manner to improve or stabilize a subject's condition.

The compounds of the invention and their pharmaceutical compositions can be administered in "therapeutically effective amounts" with respect to the subject method of treatment. The therapeutically effective amount is an amount of the compound(s) in a pharmaceutical composition which, when administered as part of a desired dosage regimen (to a mammal, preferably a human) alleviates a symptom, ameliorates a condition, or slows the onset of disease conditions according to clinically acceptable standards for the disorder or condition to be treated, e.g., at a reasonable benefit/risk ratio applicable to any medical treatment.

Administration

Compounds of the invention and their pharmaceutical compositions prepared as described herein can be administered according to the methods described herein through use of various forms, depending on the disorder to be treated and the age, condition, and body weight of the patient, as is well known in the art. As is consistent, recommended and required by medical authorities and the governmental registration authority for pharmaceuticals, administration is ultimately provided under the guidance and prescription of an attending physician whose wisdom, experience and knowledge control patient treatment.

For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route or other similar transmucosal route, they may be formulated as drops or ointments.

These formulations for administration orally or by a transmucosal route can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the gender of the patient, the nature and severity of the disorder to be treated or prevented, the route of administration and the form of the drug, in general, a daily dosage of from 0.0001 to 2000 mg, preferably 0.001 to 1000 mg, more preferably 0.001 to 500 mg, especially more preferably 0.001 to 250 mg, most preferably 0.001 to 150 mg of the compound is recommended for an adult human patient, and this may be administered in a single dose or in divided doses. Alternatively, a daily dose can be given according to body weight such as 1 nanogram/kg (ng/kg) to 200 mg/kg, preferably 10 ng/kg to 100 mg/kg, more preferably 10 ng/kg to 10 mg/kg, most preferably 10 ng/kg to 1 mg/kg. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc.

However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those excipients, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutical Compositions Incorporating Compounds 2 and 3

The pharmaceutical compositions of the invention incorporate embodiments of Compounds 2 and 3 useful for methods of the invention and a pharmaceutically acceptable carrier. The compositions and their pharmaceutical compositions can be administered orally, topically, parenterally, by inhalation or spray or rectally in dosage unit formulations. The term parenteral is described in detail below. The nature of the pharmaceutical carrier and the dose of these Compounds depend upon the route of administration chosen, the effective dose for such a route and the wisdom and experience of the attending physician.

A "pharmaceutically acceptable carrier" is a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted (3-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide: (15) alginic acid; (16) pyrogen free water; (17) isotonic saline; (18) Ringer's solution: (19) ethyl alcohol; (20) phosphate buffer solutions; and (21) other non-toxic compatible substances employed in pharmaceutical formulations.

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound of the invention as an active ingredient. A composition may also be administered as a bolus, electuary, or paste.

In solid dosage form for oral administration (capsules, tablets, pills, dragees, powders, granules, and the like), a compound of the invention is mixed with one or more pharmaceutically acceptable carriers, such as sodium citrate or dicalcium phosphate, and/or any of the following:

(1) fillers or extenders, such as starches, cyclodextrins, lactose, sucrose, glucose, mannitol, and/or silicic acid;

(2) binders, such as, for example, carboxymethylcellulose, alginates, gelatin, polyvinyl pyrrolidone, sucrose, and/or acacia;

(3) humectants, such as glycerol;

(4) disintegrating agents, such as agar-agar, calcium carbonate, potato or tapioca starch, alginic acid, certain silicates, and sodium carbonate;

(5) solution retarding agents, such as paraffin;

(6) absorption accelerators, such as quaternary ammonium compounds;

(7) wetting agents, such as, for example, acetyl alcohol and glycerol monostearate; (8) absorbents, such as kaolin and bentonite clay;

(9) lubricants, such a talc, calcium stearate, magnesium stearate, solid polyethylene glycols, sodium lauryl sulfate, and mixtures thereof; and

(10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner.

Examples of embedding compositions which can be used include polymeric substances and waxes. A compound of the invention can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to a compound of the invention, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound of the invention, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound useful for application of methods of the invention can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of a compound of the invention together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the invention to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more compounds of the invention in combination with one or more pharmaceutically acceptable sterile aqueous or nonaqueous solutions, dispersions, suspensions or emulsions, or sterile powders which may be reconstituted into sterile injectable solutions or dispersions just prior to isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a compound useful for practice of methods of the invention, it is desirable to slow the absorption of the compound from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled.

Examples of other biodegradable polymers include poly (orthoesters) and poly(anhydrides). Depot injectable formulations are also prepared by entrapping the drug in liposomes or microemulsions which are compatible with body tissue.

The pharmaceutical compositions may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The pharmaceutical compositions of the invention may be "systemically administered" "administered systemically," "peripherally administered" and "administered peripherally" meaning the administration of a ligand, drug, or other material other than directly into the central nervous system, such that it enters the patient's system and thus, is subject to metabolism and other like processes, for example, subcutaneous administration.

The compound(s) useful for application of the methods of the invention may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compound(s) useful for application of methods of the invention, which may be used in a suitable hydrated form, and/or the pharmaceutical compositions of the present invention, are formulated into pharmaceutically acceptable dosage forms by conventional methods known to those of skill in the art.

Actual dosage levels of the compound(s) useful for application of methods of the invention in the pharmaceutical compositions of this invention may be varied so as to obtain an amount of the active ingredient which is effective to achieve the desired therapeutic response for a particular patient, composition, and mode of administration, without being toxic to the patient.

The concentration of a compound useful for application of methods of the invention in a pharmaceutically acceptable mixture will vary depending on several factors, including the dosage of the compound to be administered, the pharmacokinetic characteristics of the compound(s) employed, and the route of administration.

In general, the compositions useful for application of methods of this invention may be provided in an aqueous solution containing about 0.1-10% w/v of a compound disclosed herein, among other substances, for parenteral administration. Typical dose ranges are those given above and may preferably be from about 0.001 to about 500 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

Experimental Examples

General Nucleic Acids Methods. All DNA oligonucleotides were purchased from Integrated DNA Technologies, Inc. (IDT). They were prepared by adding in nuclease free water and used without further purification. A locked nucleic acid (LNA) targeted miR-21-5p (LNA-21, Y104100689-ADC) or an LNA scrambled control (LNA-Scramble, Y100199006-DFA) were purchased from QIAGEN, Inc. The RNase L targeting siRNA (sc-45965) and control siRNA (sc-37007) were purchased from Santa Cruz Biotechnology.

Compound Libraries. The 9300-member ReFRAME (Repurposing, Focused Rescue, and Accelerated Medchem) small molecule compound collection was provided in 2016 by the California Institute for Biomedical Research (Calibr) in 1536-well format. This compound collection is a drug repurposing library containing all small molecules that have reached clinical trials or undergone significant preclinical profiling[1]. Hit compounds were re-purchased in larger quantities for testing. Compound 1 was purchased from LC Laboratories.

Solution-based Dye Displacement Assay. The solution-based dye displacement assay was completed as previously described except the dye used was TO-PRO-3 as it has less spectral overlap with compounds in ReFRAME[2]. Briefly, The RNA library (0.25 μM) was folded in 1× Assay Buffer 1 (AB1; 8 mM $Na_2HPO_4$, pH 7.0, 185 mM NaCl, 1 mM EDTA) by heating at 65° C. for 5 min followed by slowly cooling to room temperature. Bovine serum albumin (BSA) was then added to a final concentration of 40 μg/mL to afford 1× Assay Buffer 2 (AB2; 8 mM $Na_2HPO_4$, pH 7.0, 185 mM NaCl, 1 mM EDTA, 40 μg/mL BSA). The 3×2 Internal Loop Library (ILL) was added to a solution of 0.025 μM TO-PRO-3 prepared in 1× AB2 and incubated at room temperature for 15 min. Then, 4.92 μL of this solution was dispensed into each well of a black 384-well plate (Greiner Low-Volume 784076) using an Aurora Discovery FRD-1B liquid dispenser. A 10 nL aliquot of each small molecule (stock concentration: 333.3 μM) was pinned into each well eight times using a Biomek NXP Laboratory Automation Workstation equipped with a 384-pin head to obtain a final concentration of 5.3 μM. The solution was incubated at room temperature for 30 min in the dark. Fluorescence intensity was then measured on an Envision 2104 Multilabel Plate Reader (Perkin Elmer) with an excitation wavelength of 620 nm and an emission wavelength of 665 nm. DMSO and a nonspecific RNA binder mitoxantrone were used as negative and positive controls, respectively, for the assay. The change in fluorescence was normalized to a percentage (% Fluorescence Change) according to the Equation 1:

$$\%\ \text{Flourescence Change} = 100 - \left(\frac{\tilde{I}_{NC} - I}{\tilde{I}_{NC}} \times 100\right) \quad (1)$$

where I represents fluorescence of each sample, $\tilde{I}_{NC}$ represents the average of the fluorescence of all negative control raw data. If the standard deviation (SD) of all negative control raw data as I was applied to equation 1, the resulting % Fluorescence Change is a. Compounds were considered as hit compounds if they have % Fluorescence Change greater than 3 times of a. The Z-factor[3] for the dye displacement assay is 0.63±0.08.

Construction of AbsorbArray Small Molecule Microarrays. Microarrays were constructed as previously reported[4]. Briefly, a 1% agarose solution was poured onto a glass slide and dried on the benchtop. A 200 nL aliquot of 68 hit compounds (10 mM in DMSO) was pinned onto the array from a 384-well plate using Biomek NXP Laboratory Automation Workstation. Slides were then dried overnight to obtain a thin, invisible agarose layer. Slides were washed three times with 1×PBST[5] and then three times with nanopure water. Slides were dried completely in the air before RNA selection, completed by Two-Dimensional Combinatorial Screening (2DCS).

PCR Amplification and In Vitro Transcription. DNA templates encoding the RNA library, pre-miR-21, or mutant pre-miR-21 were amplified in 1×PCR Buffer (10 mM Tris, pH 9.0, 0.1% (v/v) Triton X-100 and 50 mM KCl), containing 2 μM forward primer and 2 μM reverse primer (Table 1), 330 μM of each dNTP, 4.25 mM $MgCl_2$ and 1 μL of Taq DNA polymerase in a 50 μL reaction. The conditions for PCR amplification were: initial denaturing at 95° C. for 90 s, followed by 35 cycles of 95° C. for 30 s, 55° C. for 30 s and 72° C. for 60 s). The PCR product was directly used for in vitro transcription as described previously[6]. RNA concentration was measured from its absorbance at 260 nm at 90° C. and its extinction coefficient calculated by the IDT Oligo Analyzer Tool.

RNA Selection and Screening by 2DCS. The 3×2 RNA ILL was 5'-end $^{32}$P-labeled as previously described[7] and 2DCS selections were completed as previously described 4. All oligonucleotides were folded as described in the "Solution-based Dye Displacement Assay" section. Small molecule microarrays were pre-equilibrated by 3 mL 1×AB2 for 5 min. After removing the pre-equilibration buffer, 5'-end labeled folded 3×2 RNA ILL (~50,000 cpm) was added in 3 mL 1× AB2 containing 1 mM $MgCl_2$ in the presence of competitor oligonucleotides (100 μM each). The oligonucleotide solution was evenly distributed across the microarray surface with a custom-cut piece of Parafilnm. After incubating for 30 min at room temperature, the Parafilm was removed, and the slide was washed gently by submersion in 1× AB2 for 30 s. This washing step was repeated three additional times, and the array was dried on the benchtop for 1 h. After drying, the selection was imaged by a Molecular Devices Typhoon phosphorimager, which reveals the locations (small molecules) that bound $^{32}$P-labeled RNA. To harvest and collect the bound RNAs from the ILL, 1 μL of nanopure water was added to each spot. After 30 s, the water drop was absorbed into agarose gel, hydrating it such that it could be excised with a toothpick. The RNAs were eluted from the agarose by simple incubation with water, and then treated with RNase-free DNase I. A unique barcode for each small molecule was installed by reverse transcription (RT). Barcoded RNAs were amplified by PCR, purified, and identified by next-generation sequencing (NGS) using an Ion Proton deep sequencer using PI chips (60-80 million reads) as previously described[2]. The RNA-seq data was analyzed by High Throughput Structure-Activity Relationships Through Sequencing (HiT-StARTS) to identify the most statistically significantly enriched RNAs, which are the highest affinity binders[5].

Fluorescent Binding Affinity Measurements. Binding assays were completed as previously described[5]. Briefly, the RNA of interest was folded as described in the "Solution-based Dye Displacement Assay" section, including the addition of BSA. Then, 1 was added to the RNA solution to a final concentration of 0.5 μM. The solution was serial diluted with 1× AB2 containing 0.5 μM of 1. The solutions were incubated at room temperature in the dark for 30 min. The solutions were then transferred to a black 384-well plate. Fluorescence intensity was measured using a Tecan plate reader (Gain: 100, Integration time: 40 μs) with excitation wavelength of and emission wavelength of 355 nm and 535 nm, respectively. The change in fluorescence was normalized to samples lacking RNA. Binding affinity was calculated by using Equation 2, as previously described[5].

$$I=I_0+0.5\Delta\varepsilon\{([FL]_0+[RNA]_0+K_d)-(([FL]_0+[RNA]_0+K_d)^2-4[FL]_0[RNA]_0)^{0.5}\} \quad (2)$$

where I and $I_0$ are the measured fluorescence intensity of compound with or without RNA, respectively, $\Delta\varepsilon$ is the difference between the fluorescence intensity with infinite concentration of RNA or without RNA, $[FL]_0$ and $[RNA]_0$ are the concentrations of small molecule and RNA, respectively, and $K_d$ is the dissociation constant.

In Vitro RNase L Oligomerization. To a solution of RNase L (3 μM) in 1× RNase L Buffer (add components) was added $MgCl_2$, fresh β-mercaptoethanol, and ATP to final concentrations of 10 mM, 7 mM, and 50 μM respectively. The oligomerization of RNase L induced by small molecules was assessed as previously reported[6]. The monomeric and oligomeric RNase L protein was resolved by Western blot and detected using an RNase L primary antibody (1:6000 dilution; Cell Signaling Technology, D4B4J). The blot was incubated with the antibody in 1×TBST (Tris-buffered saline supplemented with 0.1% (v/v) Tween-20) and 5% (w/v) nonfat dry milk at 4° C. overnight. After washing, the blot was incubated with 1:12000 anti-rabbit IgG, HRP-linked Antibody (Cell Signaling Technology, 7074S) in 1×TBST with 5% (w/v) nonfat dry milk for 1 h at room temperature. After washing with 1×TBST for 10 min three times, monomeric and oligomerized RNase L protein was detected by using SuperSignal West Pico Chemiluminescent Substrate (Pierce Biotechnology). ImageJ software was used for quantification.

In vitro Dicer Processing. The pre-miR-21 WT RNA or pre-miR-21 base pair mutant were 5'-end labeled with T4 polynucleotide kinase and [γ-$^{32}$P] ATP as described previously[7]. The RNA was folded in 1× Reaction Buffer (Genlantis) by heating at 55° C. for 5 min and cooling slowly to room temperature on the benchtop. The mixture was then supplemented with 2.5 mM $MgCl_2$ and 1 mM ATP. The Dicer processing reaction was performed as described previously[6]. The cleavage products were resolved on a 15% polyacrylamide denaturing gel and imaged using a Molecular Dynamics Typhoon phosphorimager and quantified with QuantityOne software from Bio-Rad.

In Vitro Chemical Cross-linking and Isolation by Pull Down (Chem-CLIP) and Competitive Chem-CLIP (C-Chem-CLIP). Growth medium [RMPI 1640 medium with L-glutamine & 25 mM HEPES (Corning)] was inactivated by heating at 95° C. to for 15 min and slowly cooling to room temperature at benchtop. Pre-miR-21 labeled with $^{32}P$ at the 5'-end (~10,000 counts) was folded in growth medium by heating at 95° C. for 1 min and slowly cooling to room temperature. To the samples was added Chem-CLIP probe 4 (1, 5, 20 or 100 μM) or negative control probe 5 (1, 5, 20 or 100 μM), and the mixtures were incubated at 37° C. for 1 h. The samples were then cross-linked by irradiation with 365 nm light for 10 min. The Chem-CLIP probe 4 or control probe 5, whether or not cross-linked to the RNA, was then clicked to disulfide biotin azide (10 mM in DMSO; 10 μL per sample; 1168-10, Click Chemistry Tools) by incubating in a solution containing 1×HEPES buffer (25 mM, pH 7), sodium ascorbate (10 μL/sample, 250 mM in $H_2O$), $CuSO_4$ (10 μL/sample, 50 mM in $H_2O$), THPTA (10 μL/sample, 50 mM in $H_2O$) for 2 h at 37° C. Streptavidin beads (Invitrogen; loading; 10 μL per sample) were then added to the samples to pull-down the cross-linked RNA, and the samples were shaken for 20 min at room temperature. The samples were washed with three times with 1×PBST (phosphate buffered saline containing 0.1% (v/v) Tween-20). The wash steps were collected and pooled. The radioactive signal from bound RNAs (on the beads) and unbound RNAs (from the wash steps) were measured by using a Beckman Coulter LS6500 Liquid Scintillation Counter. Enrichment of pre-miR-21 was calculated as previously described[6]. In vitro C-Chem-CLIP was completed by pre-treatment of the RNA with 1 (1, 5, 20 or 100 μM). Sample preparation and data analysis were completed as described above for in vitro Chem-CLIP.

Cell Culture. Cells were cultured at 37° C. and 5% $CO_2$. MDA-MB-231 cells (HTB-26, ATCC) were cultured in RMPI 1640 medium with L-glutamine & 25 mM HEPES supplemented with 1× Antibiotic/Antimycotic solution (Corning) and 10% FBS. MCF-10A cells (CRL-10317, ATCC) were cultured in 1×DMEM/F12 50/50 with L-glutamine & 15 mM HEPES (Corning) supplemented with 20% FBS, 1× Antibiotic/Antimycotic solution, 20 ng/mL human epidermal growth factor (Pepro Tech, Inc.), 10 μg/mL insulin (Sigma-Aldrich), and 0.5 mg/mL hydrocortisone (Pfaltz & Bauer). For compound treatment, compound stocks either in DMSO or water were diluted in growth medium and added to cells for the indicated time. Plasmid DNA to overexpress pre-miR-21 in pcDNA 3.1 (Addgene 21114) or a plasmid DNA encoding the pre-miR-21 mutant (custom purchased from GenScript USA, Inc.) was transfected with jetPRIME per the manufacturer's protocol. After transfection, the medium was replaced with growth medium containing the compound of interest, prepared as described above. The RNase L-targeting siRNA or a control siRNA was transfected with Lipofectamine RNAiMAX reagent (Invitrogen) per the manufacturer's protocol.

RNA Isolation and Quantitative Real-Time PCR (RT-qPCR). After treatment, total RNA was extracted and purified by using the Zymo Quick-RNA mini prep kit per the manufacturer's protocol. Reverse Transcription (RT) for mature miRNAs as well as pri- and pre-miR-21 was completed on 200 ng of RNA by using a miScript 11 RT kit (QIAGEN) according to manufacturer's protocol. RT of mRNAs was performed by using QScript kit (Quanta Bio). An Applied Biosystems QS5 384-well PCR system was used to complete qPCR experiments using Power Sybr Green Mater Mix (Life Technologies) as described previously[6].

Western Blotting. MDA-MB-231 cells were plated in 6-well plates. When they reached ~50% confluency, they were treated with vehicle (DMSO) or 4. After 48 h, the medium was removed, and the cells were washed with 1×DPBS. The cells were harvested by trypsinization, and total protein was extracted with MPER (Mammalian Protein Extraction Reagent, Thermo Scientific) as previously described[6]. Protein concentrations were determined by using a Pierce Micro BCA Protein Assay kit (Fisher Scientific). Approximately 10 μg of total protein from each sample obtained above was resolved on a SDS-polyacrylamide gel (10%), and the protein were transferred to a PVDF (0.45 μM) membrane. After blocking the membrane in 1×TBST with 5% (w/v) nonfat milk for 60 min, the membrane was incubated with 1×TBST containing 5% milk and PDCD4 (Cell Signaling Technology, 9535S) primary antibody (1:1000 dilution) at 4° C. overnight. The membrane was washed with 1×TBST for 10 min three times and then incubated with 1:2000 anti-rabbit IgG horseradish-peroxidase secondary antibody conjugate (Cell Signaling Technology, 7074S) in 1× TBST containing 5% (w/v) milk for about 2 h. After washing with 1×TBST for 10 min three times, PDCD4 protein was detected by using SuperSignal West Pico Chemiluminescent Substrate (Pierce Biotechnology). After imaging, the membrane was stripped with 1× Stripping Buffer (200 mM glycine with 0.1% SDS, pH 2.2) for 120 min at RT, and β-actin level was detected as described for PDCD4 except using β-actin (Cell Signaling Technology, 3700S) primary antibody (1:5000 dilution). ImageJ software was used for quantification of the protein bands.

Western blots for pERK, ERK, FLT3, PPARα and β-actin were performed as described for PDCD4 with pERK (Cell Signaling Technology, 9101S) primary antibody (1:1000 dilution), ERK (Cell Signaling Technology, 9102S) primary antibody (1:2000 dilution), FLT3 (Cell Signaling Technology. 3462S) primary antibody (1:1000 dilution), PPARα (Abcam, ab215270) primary antibody (1:1000 dilution), and β-actin (Cell Signaling Technology, 3700S) primary antibody (1:10000 dilution), respectively. In each case, the secondary antibody was diluted two times more than the primary antibody.

Cellular Chem-CLIP and C-Chem-CLIP to Study Occupancy of pre-miR-2L MDA-MB-231 cells in 100 mm dishes (~90% confluency) were treated with 4 or 5 for 6 h at 37° C. Then the cells were washed with 1×DPBS and cross-linked under 365 nm light for 10 min in ice cold 1×DPBS. The cells were harvested by scraping and pelleted by centrifugation. Total RNA was extracted by using the miRNeasy mini kit (Qiagen) per the manufacturer's protocol. Approximately 50 μg of total RNA was clicked to disulfide biotin azide as described in the "In Vitro Chem-CLIP and Competitive Chem-CLIP (C-Chem-CLIP)" section. Streptavidin beads (10 μL) were added, and the samples were incubated, with shaking, for 2 h at 37° C. The beads were then washed with 1× Wash Buffer (10 mM Tris-HCl, pH 7.0, 4 M NaCl, 1 mM EDTA) three times and then once with nanopure water. Bound RNAs were eluted from the beads by incubating with 200 μL of 1:1 TCEP (200 mM) pre-reduced with 600 mM of $K_2CO_3$ for 30 min at 37° C. The reaction was quenched by treatment with an equal volume of 400 mM of iodoacetamide for 30 min at room temperature. The supernatant was collected, and the beads were washed once with nanopure water: the water was added to the eluant. The combined eluant was cleaned up using RNAClean XP beads according to the manufacturer's protocol. The obtained RNA was then subjected to RT-qPCR. Enrichment of pre-miR-21 was calculated as previously described[6]. Cellular C-Chem-CLIP was completed by pre-treating with 1 (1 or 5 μM) or 3 (1 or 5 μM) for 6 h, followed by dosing with 4 (5 μM) for 6 h. Sample preparation and data analysis were completed as described above for cellular Chem-CLIP studies.

Cellular Chem-CLIP/C-Chem-CLIP to Study Occupancy of an RTK. Compound treatment and isolation of cells was completed as described for cellular occupancy studies of pre-miR-21. Total protein was extracted and concentration determined as described in the "Western Blotting" section. Approximately 1 mg of total protein was used for following pull-down experiments, using a protocol adapted from a previously published method 8. Protein cross-linked to the probe were clicked to disulfide biotin azide as described above except the amount of each reagents was doubled (20 μL/sample). Then, to the mixture was added ice-cold, 4:1 mixture of methanol/chloroform (2.5 mL) followed by 1 mL of ice-cold 1×DPBS. The mixture was centrifuged at 5000×g for 10 min at 4° C. to fractionate a protein interphase between organic and aqueous layers. After carefully removing the two layers, the protein disc was collected and washed with an ice-cold mixture of 1:1 methanol/chloroform (1 mL) three times, followed by sonication in an ice-cold mixture of 4:1 methanol/chloroform (3 mL). The washed protein mixture was centrifuged at 5000×g for 10 min at 4° C. to pellet the protein. The pellet was dissolved in $H_2O$, and to this solution was added 20 μLL streptavidin beads for 30 min at room temperature. The solution was removed, and the beads were washed once with 0.2% SDS in 1×DPBS, twice with detergent-free 1×DPBS and twice with nanopure water. After these washing steps, protein was cleaved as described above. The supernatant was collected, and protein concentration was determined with Pierce Micro BCA Protein Assay kit. Cellular C-Chem-CLIP was completed by pre-treating cells with 1, 2, 7 and 8 at 0.01, 0.1, 1 or 10 μM, respectively for 6 h, followed by dosing with 4 (1 μM) for 1 h. Sample preparation was completed as described above for cellular Chem-CLIP studies. Western blotting was performed on total protein (10 μg) before or after pull-down, indicated as "Input" or "Output", as described in Western Blotting.

PTEN Luciferase Assay. To study de-repression of PTEN, a luciferase-based cellular assay was performed as previously described[6]. Briefly, MDA-MB-231 cells (~60% confluency) in 48-well plates were co-transfected with plasmids encoding *Renilla luciferase* (for normalization) and firefly luciferase fused to the 3' UTR of PTEN by using Lipofectamine 2000 according to the manufacturer's protocol. After 5 h, the cells were treated with the compounds diluted in growth medium. Luciferase assay were then completed as previously described[4, 9].

Boyden Chamber Invasion Assay. MDA-MB-231 or MCF-10A cells ($5\times10^4$) in serum free growth medium with or without compound treatment were seeded into hanging cell culture inserts (for 24-well plates) pre-coated with Matrigel. Complete growth medium was added to the bottom well. After 16-24 h, the medium was removed, and the hanging inserts were washed with 1×DPBS twice and then fixed with 4% paraformaldehyde in 1×DPBS at room temperature for 20 min. Then the inserts were washed twice with 1×DPBS and stained with 0.1% (w/v) crystal violet 1×DPBS for 20 min. The inserts were washed twice with nanopure water and once with 1×DPBS. Cells on the surface of the Matrigel (non-invasive) were removed with cotton swabs and invading cells were counted and imaged under a microscope.

RNase L Immunoprecipitation. MDA-MB-231 cells were seed in 6-well plates and were treated with vehicle, 4 (1 μM) or 5 (1 μM) when the cells reached ~70% confluency. After 48 h, the cells were harvested and lysed in 100 μL of M-PER buffer containing protease inhibitor and RNaseOUT recombinant Ribonuclease Inhibitor (Invitrogen) on ice for 20 min. The lysate was centrifuged at 13,000×g for 15 min, and the supernatants were incubated with Dynabeads Protein A (Life Technologies) bound to RNase L mouse primary antibody or β-actin mouse primary antibody overnight at 4° C. After incubation, the beads were washed with 1×DPBS containing 0.02% (v/v) Tween-20, and RNA was extracted by using a miRNeasy Mini Kit (Qiagen) per the manufacturer's instructions. RT-qPCR was performed as described above. Relative RNA levels were determined by $\Delta\Delta C_t$ method by normalizing to 18S rRNA levels. Normalized fold change was calculated as previously described[6].

Global Proteomics Profiling by Using LC-MS/MS. MDA-MB-231 cells (~60% confluency) were treated with 1 (1 μM), 2 (1 μM), LNA-21 (0.1 μM), or vehicle for 48 h. After washing with 1×DPBS, the cells were harvested by scraping and resuspended in 1×DPBS. They were lysed by sonication and centrifuged at 14,000×g for 15 min. Protein concentrations were determined by a Bradford assay (Bio-Rad). Protein samples (340 μg) were denatured with 6 M urea in 50 mM $NH_4HCO_3$, pH 8, reduced with 10 mM TCEP (tris(2-carboxyethyl)phosphine hydrochloride) for 30 min, and alkylated with 25 mM iodoacetamide for 30 min in the dark. The samples were diluted to a final concentration of 2 M urea with 50 mM $NH_4HCO_3$, pH 8, and $CaCl_2$) was added to a final concentration of 1 mM. The protein mixture was digested with tiypsin (1.5 μL of 0.5 μg/μL) overnight at 37° C. The digested protein samples were acidified with acetic acid and desalted over a self-packed C18 spin column. After lyophilization, the samples were analyzed by LC-MS/MS as described below.

LC-MS/MS Analysis and MaxQuant Analysis. The lyophilized protein obtained above was resuspended in 0.1% formic acid in water and analyzed by using an EASY-nLC 1200 nano-UHPLC coupled to Q Exactive HF-X Quadrupole-Orbitrap mass spectrometer (Thermo Scientific) as previously reported[6]. Obtained spectra were then analyzed with MaxQuant (V1.6.1.0). Spectra were searched against the human proteome (Uniprot) and common contaminants. The search tolerance was set to 20 ppm for the first peptide search and 10 ppm for the main peptide search. The false discovery rate (FDR) for proteins, peptides and sites identification was set at 5%. All the parameters were set as previously reported[6].

Principal Component Analysis. Principal component analysis (PCA) was completed on the proteomics data that included 2,315 proteins that were detected in all samples after the technical replications were averaged, to visualize overall differences across the samples. R build in package prcomp[10] was used to perform the analysis, where scale was set to TRUE.

Quantitation of 1 and 2 in mouse plasma and tissue. Male C57BL/6 mice (n=3 per dose; 5-7 weeks) were intraperitoneally (i.p.) injected with 1 (24, 49 or 81 mg/kg) or 2 (17, 34 or 56 mg/kg) in a formulation of DMSO/Tween-80/$H_2O$ (10/10/80). After 48 h, mice were euthanized, and blood, lung and kidney were collected. Tissues were immediately frozen. Blood was centrifuged to generate plasma and immediately frozen. On the day of analysis, tissues were homogenized, mixed with 5-times volume of acetonitrile, and filtered. Drug levels were determined by mass spectrometry using an ABSciex 5500 mass spectrometer using multiple reaction monitoring. Compound 1 was detected using the mass transition 393 □322, and 2 was detected using the mass transition 1006□559.

In Vivo Studies to Assess Metastasis of Breast Cancer to the Lung. Female NOD/SCID mice (n=10; 5-7 weeks) were used for in vivo breast cancer metastasis studies as previously reported[6]. Briefly, mice purchased from Jackson Laboratory were intravenously injected (tail vein) with MDA-MB-231-Luc cells ($0.8\times10^6$ cells/mice). Luciferase activity was monitored every other day to determine when to initiate treatment [averaged luciferase signal from mice is ten times higher than the background as measured by LagoX (Spectral Instruments)]. After 5 days, the mice were split into three groups, with each group having the same luciferase signal. The mice in vehicle group were i.p. injected with DMSO/Tween-80/$H_2O$ (10:10:80) while treated groups were i.p. injected with 83 mg/kg of 1 or 56 mg/kg of 2 in the same formulation every other day (q.o.d.). After 30 days, lungs were harvested and immediately fixed in Bouin's solution (Sigma, HT10132-1L) for 24 h to image nodules. After counting the nodules, the fixed lungs were washed in 60 mL of 10% formalin solution four times over 48 h to remove Bouin's solution. Paraffin-embedded sections of the lungs were then generated by the Histology Core at Scripps Research Florida for further staining.

Lung Tissue Histology. All histological analyses were performed as previously reported[6]. The slides were stained on a Leica BondMax Immunostaining platform by using a DAB refine kit. H&E staining and PDCD4, pERK and ERK IHC were performed by the Histology Core at Scripps Research Florida. All antibodies were used at a 1:100 dilution: anti-PDCD4 (Abcam, ab51495); anti-pERK (Cell Signaling Technology, 4370S); and ERK (Cell Signaling Technology, 9102S). The primary antibodies were detected using a DAB Substrate Kit (Vector Laboratories, Inc.) per the manufacturer's protocol.

To visualize miR-21 and pre-miR-21 by fluorescence in situ hybridization (FISH), the paraffin-embedded sections were incubated at 56° C. overnight and cleaned with xylene three times, followed by washing with serially diluted concentrations of ethanol (100%, 95%, 90%, and 85%). The slides were then washed with MilliQ water three times and immersed in 0.3% (v/v) $H_2O_2$ for 30 min at room temperature. The slides were then washed with MilliQ water three times and digested with proteinase K (QIAGEN) at 37° C. for 15 min. After washing three times with MilliQ water, the slides were dehydrated with 95% ethanol and air-dried completely at room temperature. The slides were then hybridized with FITC-labeled LNA probes[6] complementary to mature (CAACATCAGTCTGATAAGCT*/36-FAM SEQ ID NO: 16) or pre-miR-21 (ATTCAACAGTCAACATCAGTCT/36-FAM SEQ ID NO: 17) at 37° C. C overnight. After hybridization, the slides were washed with 2×SSC (saline sodium citrate buffer) three times and then 1×DPBS three times, all at room temperature. The slides were then incubated with an anti-FITC horseradish peroxidase-conjugated antibody (Abcam) for 2 h at room temperature. The slides were washed with 1×TBST three times.

After staining of interest was completed, the slides were dehydrated, cover-slipped with Cytoseal 60, and imaged with a Leica DM13000 B upright fluorescent microscope.

Alport Mice Studies. Alport mice ($Col4a3^{-/-}$) and wild type (WT) mice ($Col4a3^{+/+}$) were obtained from the breeding of heterozygous ($Col4a3^{+/+}$). Urine was collected 1 day before the treatment, considered as Day 1. The treatment started at Day 2, at around 4 weeks of age. Alport mice were treated with vehicle or 2 as described for NOD/SCID mice in the "In Vivo Studies to Assess Metastasis of Breast Cancer to the Lung" section. Urine was collected every other day for analysis of albumin or creatine levels. After 6 weeks of treatment, the mice were euthanized on Day 43. One kidney was frozen in −80° C. for Western blot and RT-qPCR analyses. The other kidney was fixed in formalin for paraffin-embedding sectioning and further staining.

Evaluation of Kidney Function. The concentration of urine albumin was determined by using a Mouse Albumin ELISA Kit (Bethyl Laboratories Inc, E99-134) per the manufacturer's protocol. Urine creatinine level was measured by using a Urinary Creatinine Assay Kit (Fisher Scientific, 50-673-569) per the manufacturer's protocol.

Kidney Tissue Histology. Silver staining, PAS staining, and PPARα staining were performed by Histology Core at Scripps Research Florida. The anti-PPARα (Abcam, ab215270) was used at 1:1000 dilution. FISH imaging of miR-21 and pre-miR-21 were completed as described in "Lung Tissue Histology".

Computational Methods. The three-dimensional structures of Dovitinib with ionization states at pH 7.0±2.0 in FIG. 1B were generated with LigPrep (Schrodinger, Inc.). A model of pre-miR-21 bound to a previously reported compound[6] was processed and minimized using the Protein Preparation Wizard (Schrodinger, Inc.) to assign bond orders and add missing hydrogens. Docking was carried out with Induced Fit Docking (Schrodinger, Inc.), where the ligand and receptor are flexible, and no imposed constraints. Docking poses were ranked by Prime energy.

Statistical Analysis. All plots show means of data with error bar representing SD, unless otherwise dictated. Data were plotted and analyzed using commercially available software (Perseus, GraphPad prism, lmageJ). Comparisons of two groups were made with the statistical test indicated in each figure caption, typically a two-tailed Student t test. Perseus was used to calculate the FDR rate for the Volcano plots of global miRNA profiling and proteomics data. A two-tailed Kolmogorov-Smirnov test was used to calculate the p value between distributions. Unless otherwise specified, significance was accepted at $p<0.05$.

Synthetic Experimental Procedures

General Methods.

Ethyl 3-ethoxy-3-iminopropionate hydrochloride salt, 1((-2-N-Boc-ainino)ethyl)piperazine, and 2-Amino-6-fiuorobenzonitrile were purchased from Combi-Blocks. Potassium carbonate was purchased from EMD Millipore Corporation. N,N'-Disuccinimidyl carbonate, Fmoc-15-amino-4,7,10,13-tetraoxapentadecanoic acid, and piperidine, were purchased from Chem Impex Intl, Inc. N,N-Diisopropylethylamine, and 3-(3-(But-3-yn-1-yl)-3H-diazirin-3-yl)propanoic acid were purchased from Sigma-Aldrich. Dimethylformamide were purchased from Fisher Chemical. HATU was purchased from Oakwood Products, Inc. Acetic acid was purchased from Avantor Performance Materials. Propylamine, and lithium bis(trimethylsilyl)amide were purchased from Alfa Aesar. Lastly, 5-Chloro-2- nitroaniline was purchased from Acros Organics. Reagents and solvents purchased commercial suppliers were directly used without further purification.

Reactions were monitored with thin layer chromatography (TLC, Agela Technologies) or by LC-MS. Bands on TLC were visualized under UV light (254 nm). Products were purified by silica gel column chromatography or by HPLC (waters 2487 and 1525) equipped with a SunFire® Prep C18 OBDTM 5 μm column (19×150 mm) with a flow rate of 5 mL/min. Product purities were analyzed by HPLC (Waters 2487 and 1525) equipped with a SunFire® C18 3.5 μm column (4.6×150 mm) with a flow rate of 1 mL/min. The gradient used for purification and purity analysis is from 100% of $H_2O$ (containing 0.1% TFA) to 100% MeOH (containing 0.1% TFA) in 60 min.

NMR spectra were measured using an Ascend™ 600 (Bruker) (600 MHz for $^1H$ and 150 MHz for $^{13}C$) or a 400 UltraShield™ (Bruker) (400 MHz for $^1H$ and 100 MHz for $^{13}C$). Chemical shifts are reported in ppm by using residual solvent as internal standards. Coupling constants (J values) are reported in hertz.

Mass spectrometry was completed by using an Agilent 1260 Infinity LC system coupled to an Agilent 6230 TOF (HR-ESI) equipped with a Poroshell 120 EC-C18 column (Agilent, 50 mm×4.6 mm, 2.7 μm) or by using 4800 Plus MALDI TOF/TOF Analyzer.

Synthetic Schemes and Methods

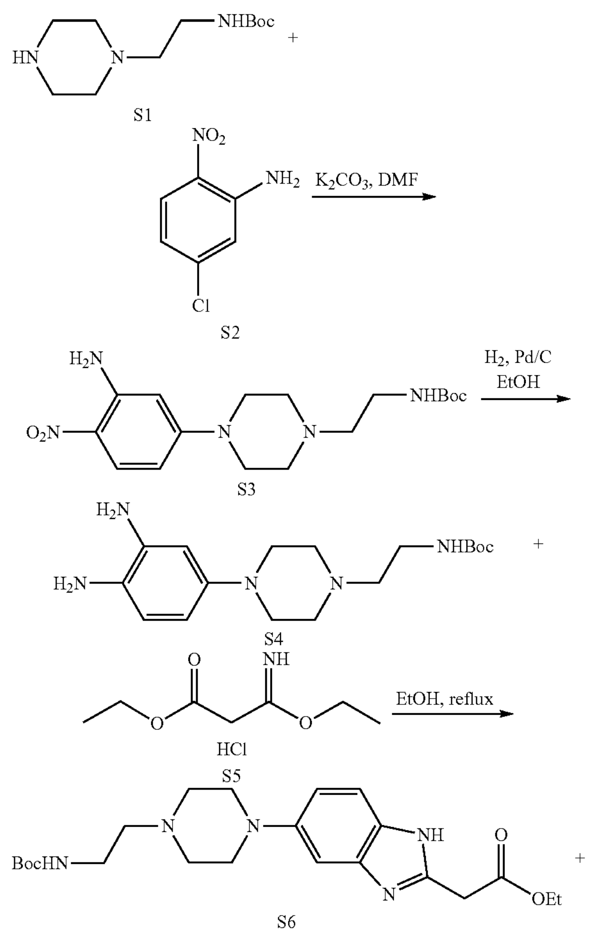

S1 + S2

S3

S4 + S5

S6 +

-continued

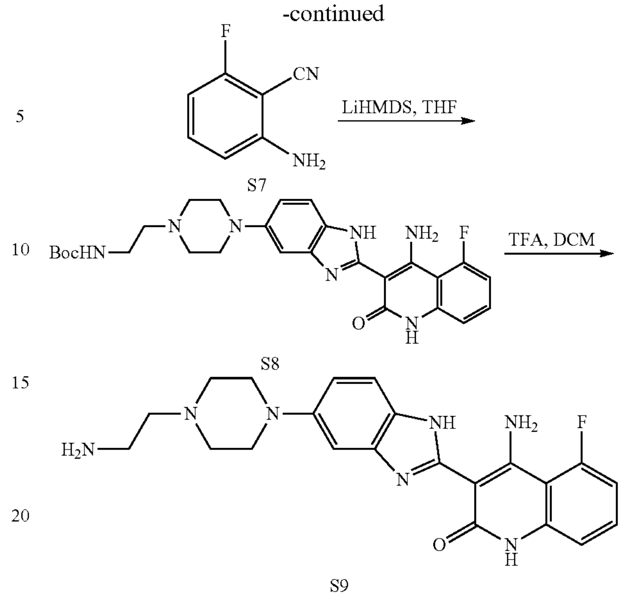

S7

S8

S9

Compound S3. A solution of the amine S1 (998 mg, 4.36 mmol), aniline S2 (500 mg, 2.90 mmol), and $K_2CO_3$ (1.91 g, 14.5 mmol) in 5 mL of DMF was refluxed with stirring for 24 h. The reaction mixture was then diluted with ethyl acetate and extracted with $H_2O$. The combined organic layers were washed with brine, dried over anhydrous $Na_2SO_4$ and concentrated in vacuo. The residue was purified by column chromatography to give S3 as a yellow solid (550 mg, 1.51 mmol, 52.3%). $^1H$ NMR (400 MHz, $CD_3OD$) δ (ppm) 7.92 (d, J=9.8 Hz, 1H), 6.36 (dd, J=9.8, 2.7 Hz, 1H), 6.17 (d, J=2.6 Hz, 1H), 3.41-3.38 (m, 4H), 3.23 (t, J=6.7 Hz, 2H), 2.62-2.60 (m, 4H), 2.50 (t, J=6.7 Hz, 2H), 1.44 (s, 9H). $^{13}C$ NMR (100 MHz, $CD_3OD$) δ (ppm) 158.4, 157.1, 149.9, 128.6, 125.1, 106.7, 99.1, 80.1, 58.7, 53.8, 47.6, 38.4, 28.8. HRMS (m/z): calculated for $C_{17}H_{28}N_5O_4$ $[M+H]^+$ 366.2136, found: 366.2074.

Compound S6. A solution of S3 (500 mg. 1.37 mmol) and 50 mg of 10% Pd/C in 30 mL of ethanol (EtOH) was stirred at room temperature (r.t.) under an atmosphere of $H_2$ overnight and then the Pd/C was filtered off. The filtrate was concentrated in vacuo to ~20 mL, and to the mixture was added the amidate S5 (1.34 g, 6.85 mmol). The final solution was then stirred under reflux for 1 h. After cooling down to room temperature, the mixture was quenched with saturated $NH_4Cl$ and extracted with ethyl acetate. The combined organic layer was washed with brine, dried over anhydrous $Na_2SO_4$ and concentrated in vacuo. The residue was purified by column chromatography to give S6 as a grey solid (300 mg, 0.7 mmol, 51%). $^1H$ NMR (400 MHz, DMSO-$d^6$) δ (ppm) 12.05 (br, 1H), 7.34 (d, J=8.7 Hz, 1H), 6.93 (s, 1H), 6.89 (d, J=8.8 Hz, 1H), 6.70 (m, 1H), 4.11 (q, J=7.1 Hz, 2H), 3.89 (s, 2H), 3.08 (m, 6H), 2.57 (m, 4H), 2.39 (m, 2H), 1.38 (s, 9H), 1.22 (t, J=7.1 Hz 3H). $^{13}C$ NMR (150 MHz, DMSO-$d^6$) δ (ppm) 168.9, 155.6, 147.6, 146.4, 137.1, 135.3, 118.4, 113.0, 97.5, 77.5, 60.8, 57.4, 52.9, 50.2, 37.4, 35.1, 28.3, 14.1. HRMS (m/z): calculated for $C_{22}H_{34}N_5O_4$ $[M+H]^+$ 432.2605, found: 432.2563.

Compound S8. To a solution of S6 (1 g, 2.32 mmol) and S7 (473 mg, 3.48 mmol) in 10 mL of tetrahydrofuran (THF) was added a solution of lithium bis(trimethylsilyl)amide (LiHMDS; 1.0 M in THF, 11.6 mL) dropwise at 0° C. The mixture was stirred at r.t. overnight. To the reaction mixture was added saturated $NH_4Cl$. The mixture was extracted with ethyl acetate, washed with brine and concentrated in vacuo. The residue was purified by column chromatography to give S8 as a brown solid (560 mg, 1.07 mmol, 46%). $^1$H NMR (400 MHz, DMSO-d$^6$) δ (ppm) 12.74 (m, 1H), 11.61 (s, 1H), 11.38 (m, 1H), 7.74 (m, 2H), 7.18 (m, 1H), 7.43 2-7.60 (m, 2H), 7.06-7.25 (m, 2H), 7.04 (dd, J=14, 8 Hz, 1H), 6.94 (m, 11H), 3.08 (m, 6H), 2.57 (m, 4H), 2.39 (t, J=6.4 Hz, 2H), 1.39 (s, 9H). $^{13}$C NMR (100 MHz, DMSO-d$^6$) δ (ppm) 161.9, 161.9, 160.2 (d, J=248.3 Hz), 151.7, 151.4, 151.3, 150.5, 147.7, 147.4, 141.9, 139.6, 135.3, 132.7, 132.2, 132.0, 126.2, 117.2, 114.1, 113.0, 112.3, 111.9, 107.9 (d, J=23.6 Hz), 103.5, 102.7 (d, J=10.14 Hz), 98.2, 91.0, 90.9, 77.6, 57.4, 53.0, 52.9, 50.3, 49.4, 37.4, 28.3. FIRMS (m/z): calculated for $C_{27}H_{33}FN_7O_3$ $[M+H]^+$ 522.2623, found: 522.2543.

Compound S9. A solution of S8 (1 g, 1.91 mmol) in 5 mL of trifluoracetic acid/dichloromethane (TFA/DCM; 30/70) was stirred at r.t. for 1 h, and the solution was concentration in vacuo to give compound S9 without further purification.

RIBOTAC 2. To a solution of S9 (168 mg, 0.4 mmol) and N,N'-disuccinimidyl carbonate (DSC; 123 mg, 0.48 mmol) in 3 mL of N,N-dimethylformamide (DMF) was added N,N-diisopropylethylamine (DIPEA; 198 μL, 1.2 mmol), and the mixture was stirred at r.t. After 20 min, compound S10[6] (268 mg, 0.48 mmol) was added to the solution, and the mixture was stirred at r.t. until S9 was consumed completely, as determined by LC-MS. The final reaction mixture was concentrated in vacuo and purified by HPLC to give 2 as a TFA salt (168 mg, 0.167 mmol, 42%). $^1$H NMR (400 MHz, $CD_3OD$) δ (ppm) 7.50-7.65 (m, 51), 7.40-7.45 (m, 311), 7.16-7.20 (m, 311), 6.96-7.05 (m, 1H), 6.87-6.95 (m, 3H), 4.28 (q, J=7.0 Hz, 2H), 4.13-4.20 (m, 2H), 3.82-3.88 (m, 2H), 3.48-3.80 (m, 1611), 3.29-3.31 (m, 2H), 3.27 (t, J=5.1 Hz, 21), 2.98-3.26 (m, 411), 1.33 (t, J=7.1 Hz, 311). $^{13}$C NMR (100 MHz, $CD_3OD$) δ (ppm) 184.2, 177.6, 166.8, 162.9, 162.2 (d, J=249.2 Hz), 161.2, 161.9, 150.1, 149.2, 148.2, 141.9, 138.7, 134.5 (d, J=12.8 Hz), 132.8, 130.9, 129.4, 128.4, 126.1, 125.9, 124.9, 117.8, 117.6, 115.6, 114.2, 113.8, 109.8 (d, J=24.2 Hz), 101.5, 98.8, 71.6, 71.4, 71.2, 70.5, 69.3, 61.4, 59.9, 53.5, 36.6, 14.8. MALDI (m/z): calculated for $C_{51}H_{57}FN_9O_{10}S$ $[M+H]^{30}$ 1006.3928, found: 1006.3757.

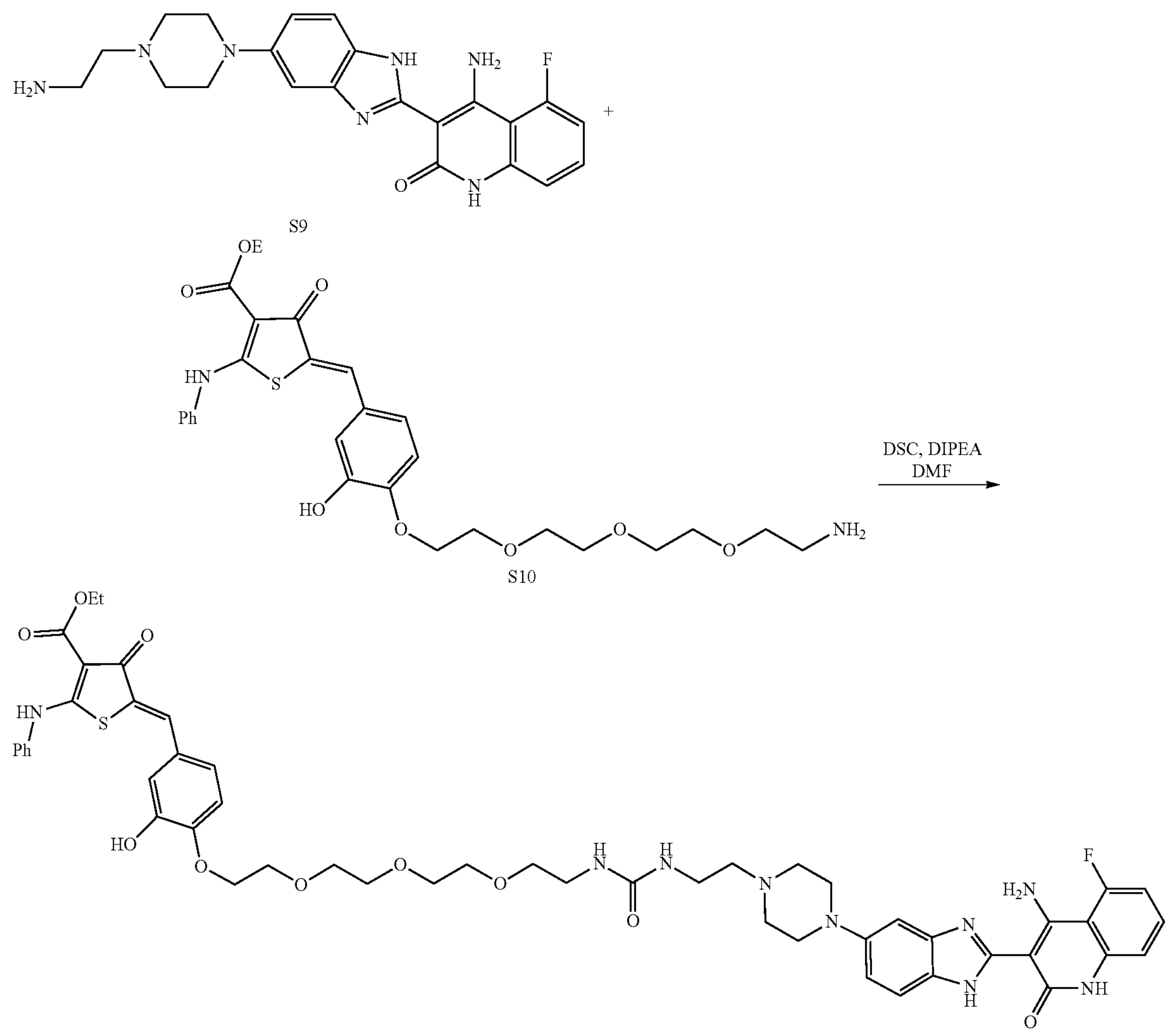

S9

+

S10

2

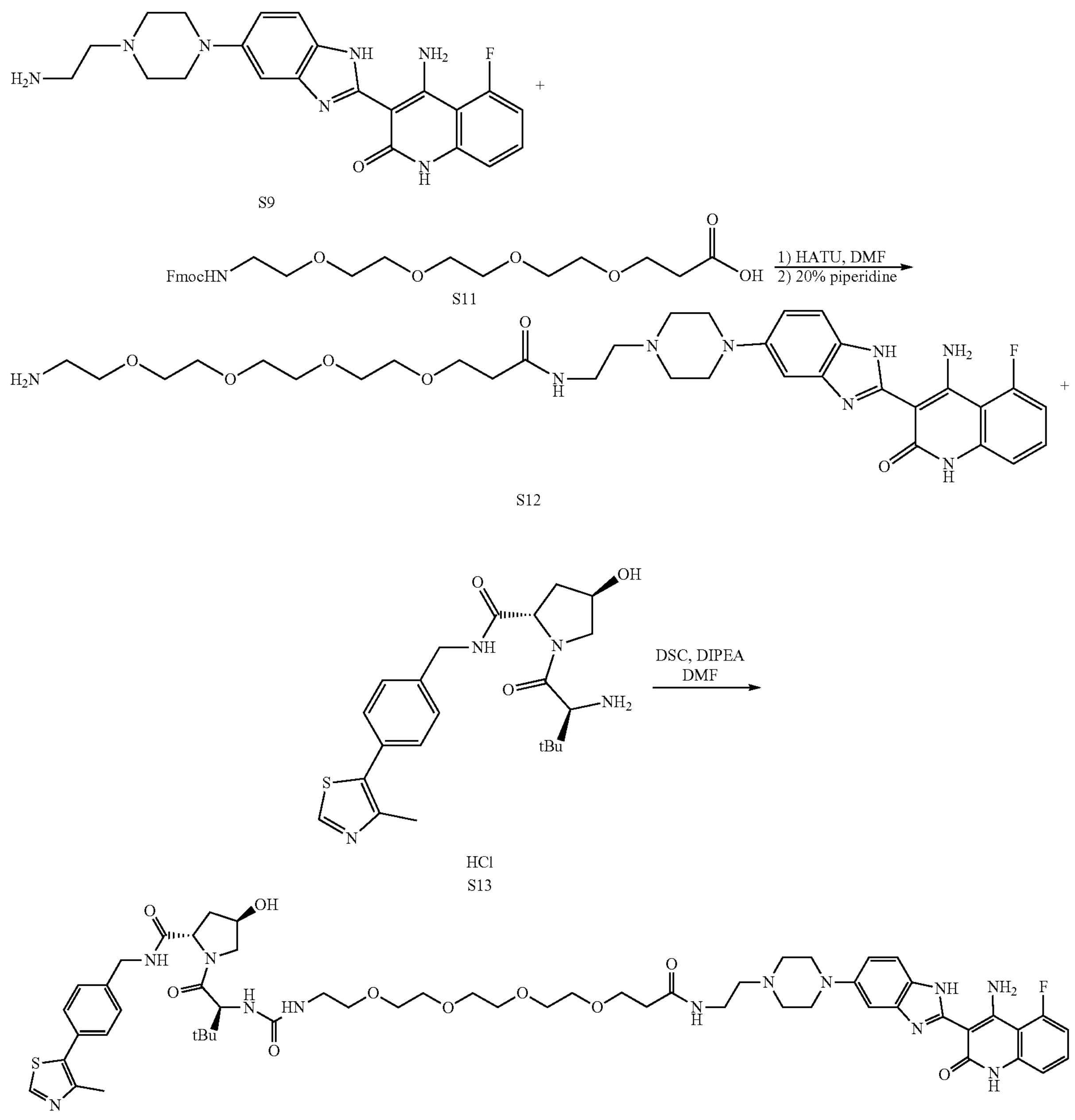

PROTAC 3. A solution of S9 (14 mg. 0.33 mmol), S11 (16 mg, 0.033 mmol), and 1-[bis(dimethylamino)methylene]-1H-1,2,3-triazolo[4,5-b]pyridinium 3-oxid hexafluorophosphate (HATU; 15.2 mg, 0.04 mmol) in 0.5 mL of DMF was stirred at r.t. for 30 min. Then, 0.1 mL of piperidine was added to the mixture. The mixture was stirred at r.t. for another 30 min and then concentrated in vacuo. To the final slurry was added DSC (9.2 mg, 0.036 mmol) and DIPEA (55 µL, 0.3 mmol), and the mixture was stirred at r.t. for 20 min, followed by the addition of S13 (17 mg, 0.036 mmol). The mixture was stirred at r.t. for 24 h. The final mixture was purified by J-IPLC to give PROTAC 3 as a TFA salt (2.3 mg, 0.002 mmol, 6%). $^1$H NMR (600 MHz, $CD_3OD$) δ (ppm) 8.94 (s, 1H), 7.64 (d, J=8.9 Hz, 11-1), 7.55-7.63 (m, 111), 7.44 (d, J=8.9 Hz, 2H), 7.37 (d, J=8.4 Hz, 2H), 7.28 (d, J=2.0 Hz, 1H), 7.25 (dd, J=8.9 Hz, 2.2 Hz, 1H), 7.18 (d., J=8.3 Hz, 1H), 6.99-7.05 (m, 1H), 4.58 (t, J=7.7 Hz, 2H), 4.47-4.53 (m, 2H), 4.43 (s, 1H), 4.36 (d, J=15.5 Hz, 1H), 3.72-4.00 (m, 7H), 3.52-3.70 (m, 15H), 3.47 (m, 2H), 3.40 (m, 2H), 3.27 (m, 2H), 2.52 (t, J=5.7 Hz, 2H), 2.45 (s, 3H), 2.22 (m, 1H), 2.08 (m, 1H), 1.03 (s, 9H). $^{13}$C NMR (150 MHz, $CD_3OD$) δ (ppm) 176.1, 174.5, 173.7, 162.2 (d, J=248.6 Hz), 160.8, 160.5, 155.3, 153.1, 149.1, 148.5, 140.4, 134.5 (d., J=12.0 Hz), 133.7, 131.2, 130.3, 129.0, 117.7, 115.9, 113.8, 109.8 (d, J=23.8 Hz), 104.3, 101.9, 90.9, 71.5, 71.4, 71.3, 71.1, 67.9, 60.9, 59.6, 58.5, 58.0, 53.7, 43.7, 41.0, 39.0, 37.3, 36.6, 35.8, 27.0, 15.6. MALDI (m/z): calculated for $C_{56}H_{74}FN_{12}O_{10}S$ $[M+H]^+$ 1125.5350, found: 1125.7637.

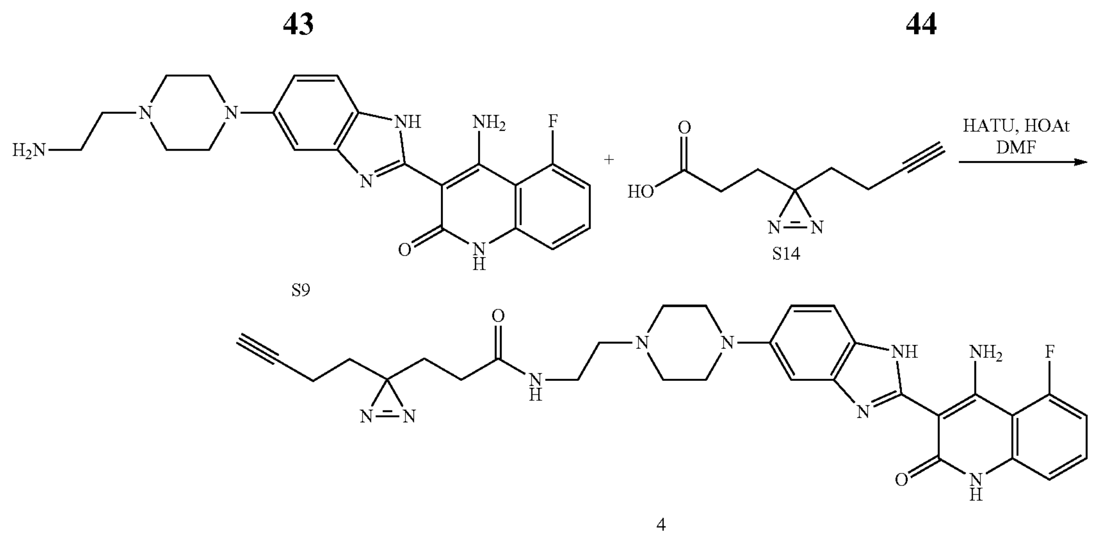

S9

S14

4

Chem-CLIP Probe 4. A solution of S9 (2.1 mg, 0.005 mmol), S14 (1.2 mg, 0.0075 mmol), HATU (2.9 mg, 0.0075 mmol), I-hydroxy-7-azabenzotriazole (HOAt; 1 mg, 0.0075 mmol) and triethylamine (TEA: 1.52 mg, 0.015 mmol) in 0.2 ML of DMF was stirred at r.t. for 2 h in dark. The reaction mixture was then purified by HPLC to afford 4 as a TFA salt. $^{1}H$ NMR (400 MHz, $CD_3OD$) δ (ppm) 7.53-7.62 (m, 2H), 7.26 (s, 11H), 7.13-7.22 (m, 2H), 6.97-7.05 (m, 1H), 3.55-3.98 (m, 6H), 3.00-3.40 (m, 6H), 2.30 (t, J=2.7 Hz, 1H), 2.10 (t, J=7.2 Hz, 2H), 2.04 (td, J=7.4 Hz, 2.6 Hz, 2H), 1.81 (t, J=7.2 Hz, 2H), 1.64 (t, J=7.4 Hz, 2H). $^{13}C$ NMR (150 MHz, $CD_3OD$) δ (ppm) 176.4, 163.6, 162.3 (d. J=248.3 Hz), 154.9, 150.6, 148.5, 141.5, 136.4, 132.0, 134.1 (d, J=12.0 Hz), 117.1, 116.0, 113.6, 109.7 (d, J=24.3 Hz), 104.4, 102.5, 91.4, 83.6, 70.4, 58.1, 53.7, 49.5, 35.6, 33.3, 30.7, 29.3, 29.0, 13.8. HRMS (m/z): calculated for $C_{56}H_{74}FN_{12}O_{10}S$ $[M+H]^+$ 570.2736, found: 570.2655.

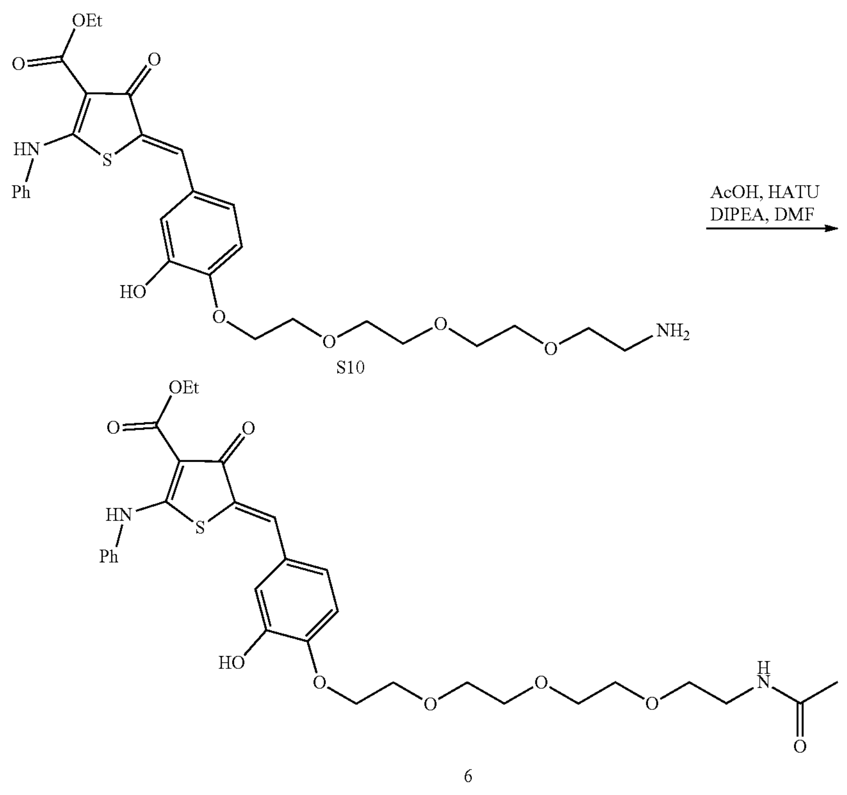

S10

6

Compound 6. To a solution of HATU (5.7 mg, 0.015 mmol) and DIPEA (5 μL, 0.03 mmol) in 0.5 mL of DMF was added 10 μL of acetic acid solution (AcOH; 1 M in DMF). The mixture was stirred at r.t. for 10 min, followed by the addition of S10 (5.6 mg, 0.01 mmol). After stirring at r.t. overnight, the reaction was purified by HPLC to afford 6 as a TFA salt (3.4 mg, 0.0056 mmol, 56%). $^{1}H$ NMR (600

MHz, $CD_3OD$) 7.66 (s, 1H), 7.53-7.58 (m, 2H), 7.44-7.53 (m, 3H), 6.99-7.07 (m, 3H), 4.38 (q, J=7.1 Hz, 2H), 4.18-4.23 (m, 2H), 3.82-3.90 (m, 2H), 3.69-3.74 (m, 2H), 3.65-3.68 (m, 2H), 3.56-3.60 (m, 2H), 3.50 (t, J=5.6 Hz, 2H), 1.91 (s, 3H), 1.39 (t, J=7.1 Hz, 3H). $^{13}C$ NMR (150 MHz, $CD_3OD$) δ (ppm) 183.1, 176.9, 172.0, 148.8, 147.1, 137.4, 131.7, 129.6, 128.1, 127, 1, 125.0, 124.9, 123.4, 116.1, 113.0, 97.5, 70.2, 70.1, 69.8, 69.2, 69.1, 67.9, 60.0, 39.1, 21.1, 13.4. HRMS (m/z): calculated for $C_{30}H_{37}N_2O_9S$ $[M+H]^+$ 601.2214, found: 601.2119.

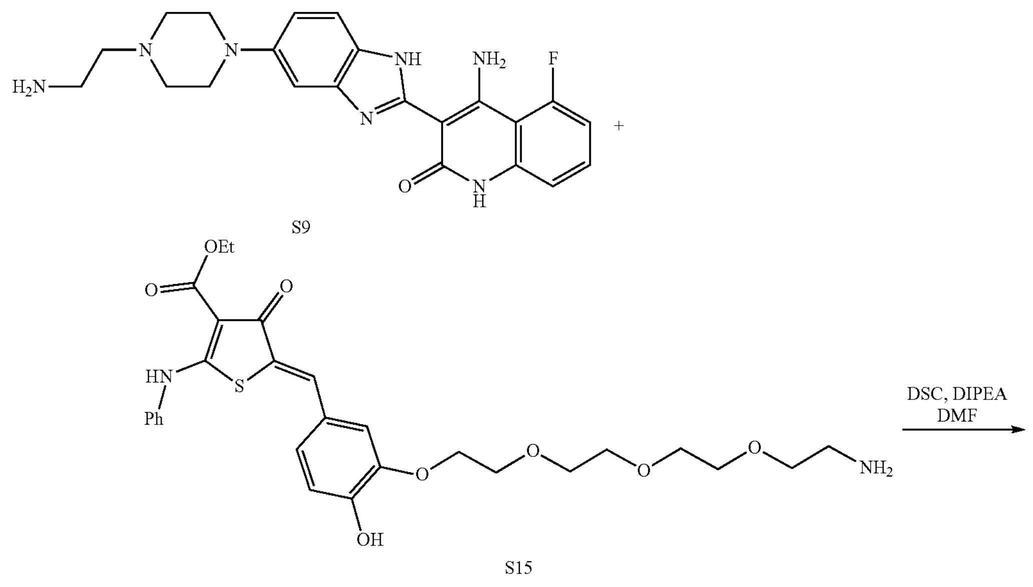

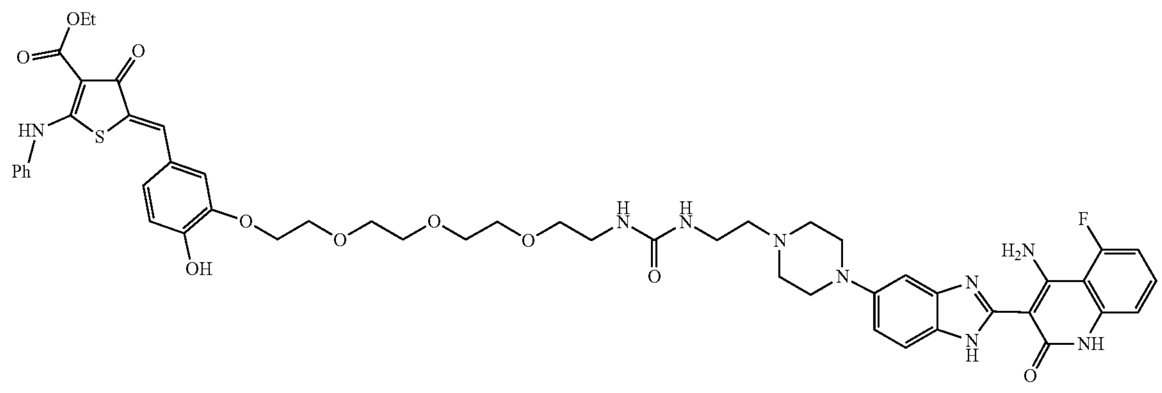

7

Compound 7. To a solution of S9 (2.1 mg, 0.005 mmol) and DSC (3.8 mg, 0.015 mmol) in 0.2 mL of DMF was added DIPEA (2.5 μL, 0.015 mmol), and the mixture was stirred at r.t. After 20 min, compound S15[6] (5.6 mg, 0.01 mmol) was added to the solution, and the mixture was stirred at r.t. overnight. The final reaction mixture was concentrated in vacuo and purified by HPLC to give 6 as a TFA salt (1.0 mg, 0.001 mmol, 20%). $^1H$ NMR (400 MHz, $CD_3OD$) δ (ppm) 7.48-7.63 (m, 5H), 7.38-7.45 (m, 3H), 7.06-7.16 (m, 3H), 6.95-7.05 (m, 3H), 6.81 (d, J=8.3 Hz, 1H), 4.31 (q, J=7.1 Hz, 2H), 4.08-4.14 (m, 21H), 3.57-3.86 (m, 14H), 3.50-3.56 (m, 4H), 3.0-3.3 (m, 8H), 1.35 (t, J=7.1 Hz, 3H). $^{13}C$ NMR (150 MHz, $CD_3OD$) δ (ppm) 184.4, 171.5, 166.9, 163.5, 162.4 (d, J=248.4 Hz), 162.2, 154.9, 150.7, 148.5, 148.3, 141.5, 138.7, 134.1 (d, J=12.0 Hz), 133.2, 130.9, 129.3, 126.9, 125.8, 125.6, 125.5, 117.2, 117.1, 113.6, 109.7 (d, J=24.0 Hz), 104.4, 102.2, 98.9, 91.3, 71.6, 71.4, 71.3, 71.2, 70.7, 69.6, 61.4, 60.0, 53.6, 49.6, 41.2, 36.6, 14.8. MALDI (m/z): calculated for $C_{51}H_{57}FN_9O_{10}S$ $[M+H]^+$ 1006.3928, found: 1006.3607.

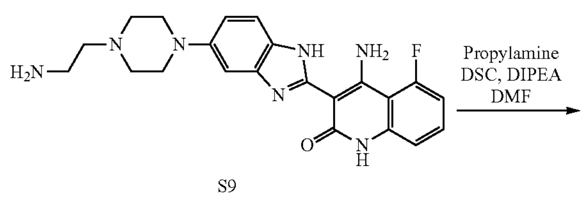

-continued

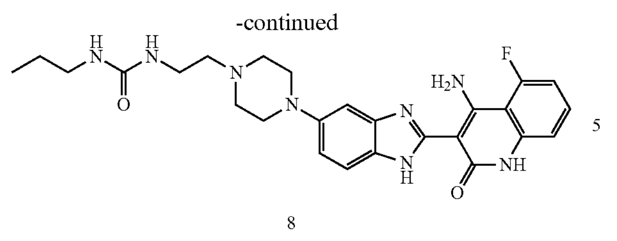

8

Compound 8. A solution of S9 (12.8 mg, 0.03 mmol), DSC (8.4 mg, 0.033 mmol) and DIPEA (15 μL, 0.09 mmol) was stirred at r.t. for 10 min, followed by the addition of propylamine (1.8 mg, 0.03 nmol). The mixture was stirred at r.t. overnight and then purified by HPLC to give 8 as a TFA salt (3.1 mg, 0.006 mmol, 20%). $^1$H NMR (400 MHz, $CD_3OD$) 7.55-7.78 (m, 2H), 7.22-7.28 (m, 2H), 7.14 (d, J=8.4 Hz, 1H), 6.96-7.05 (m, 1H), 3.68-4.02 (m, 4H), 3.56 (m, 2H), 3.33 (m, 2H), 3.14-3.31 (m, 4H), 3.10 (t, J=7.0 Hz, 2H), 1.45-1.58 (m, 2H), 0.93 (t, J=7.4 Hz, 3H). $^{13}$C NMR (100 MHz, $CD_3OD$) δ (ppm) 161.7, 160.8 (d, J=248.8 Hz), 160.7, 154.0, 148.1, 146.9, 140.5, 133.7, 133.2 (d, J=12.0 Hz), 128.4, 116.6, 114.3, 112.4, 108.4 (d, J=24.1 Hz.), 102.8 (d, J=10.7 Hz), 100.3, 89.3, 58.4, 52.1, 41.7, 35.1, 22.9, 10.2. HRMS (m/z): calculated for $C_{26}H_{32}FN_8O_2$ $[M+H]^+$ 507.2627, found: 507.2566.

TABLE S1

Sequences of oligonucleotide primers used in these studies.

| Name of Oligonucleotide | Sequence (5' → 3') | Experiment | Supplier | SEQ ID NO: |
|---|---|---|---|---|
| RNU6 | ACACGCAAATTCGTGAAGCGT TC | RT-qPCR | IDT | 1 |
| Universal Reverse | GAATCGAGCACCAGTTACGC | RT-qPCR | IDT | 2 |
| hsa-miR-21 forward | TAGCTTATCAGACTGATGTTGA | RT-PCR | IDT | 3 |
| pre-miR-21 template | TAGCTTATCAGACTGATGTTGACTGT TGAATCTCATGGCAACACCAGTCGAT GGGCTG | RT-PCR | IDT | 4 |
| pre-miR-21 template forward | TAATACGACTCACTATAGTAGC TTATCAGACTG | RT-PCR | IDT | 5 |
| pre-miR-21 template reverse | CAGCCCATCGACTGG | RT-PCR | IDT | 6 |
| RNase L F | GACACCTCTGCATAACGCAGT | RT-PCR | IDT | 7 |
| RNase L F | AGGGCTTTGACCTTACCATACA | RT-PCR | IDT | 8 |
| 18S Fwd. | GTAACCCGTTGAACCCCATT | RT-qPCR | IDT | 9 |
| 18S Rev. | CCATCCAATCGGTAGTAGCG | RT-qPCR | IDT | 10 |
| GAPDH Fwd. | GTTCGACAGTCAGCCGCATC | RT-qPCR | IDT | 11 |
| GAPDH Rev | GGAATTTGCCATGGGTGGA | RT-qPCR | IDT | 12 |

Sequences for Global miRNA profiling primers were previously described[6].

REFERENCES FOR SPECIFICATION

1. Janes, J.; Young, M. E.; Chen, E.; Rogers, N. H.; Burgstaller-Muehlbacher, S.; Hughes, L. D.; Love, M. S.: Hull, M. V.; Kuhen, K. L.; Woods, A. K.; Joseph, S. B.; Petrassi, H. M.; McNamara, C. W.; Tremblay, M. S.; Su, A. L; Schultz, P. G.; Chatterjee, A. K., The ReFRAME library as a comprehensive drug repurposing library and its application to the treatment of cryptosporidiosis. *Proc Nat Acad Sci USA* 2018, 115 (42), 10750-10755.
2. Tran, T.; Disney, M. D., Identifying the preferred RNA motifs and chemotypes that interact by probing millions of combinations. *Nat Commun* 2012, 3, 1125.
3. Zhang, J. H.; Chung, T. D.: Oldenburg, K. R., A simple statistical parameter for use in evaluation and validation of high throughput screening assays. *J Biomol Screen* 1999, 4 (2), 67-73.
4. Velagapudi, S. P.; Costales, M. G.; Vummidi, B. R.; Nakai, Y.; Angelbello, A. J.; Tran, T.; Haniff, H. S.; Matsumoto, Y.; Wang, Z. F.; Chatterjee, A. K.; Childs-Disney, J. L.; Disney, M. D., Approved Anti-cancer Drugs Target Oncogenic Non-coding RNAs. *Cell Chem Biol* 2018, 25 (9), 1086-1094 e7.
5. Velagapudi, S. P.; Luo, Y.; Tran, T.; Haniff, H. S.; Nakai, Y.; Fallahi, M.; Martinez, G. J.; Childs-Disney, J. L.; Disney, M. D., Defining RNA-small molecule affinity landscapes enables design of a small molecule inhibitor of an oncogenic noncoding RNA. *ACS Cent Sci* 2017, 3 (3), 205-216.
6. Costales, M. G.; Aikawa, H.; Li, Y.; Childs-Disney, J. L.; Abegg, D.; Hoch, D. G.; Pradeep Velagapudi, S.; Nakai, Y.; Khan, T.; Wang, K. W.; Yildirim, I.; Adibekian, A.; Wang, E. T.; Disney, M. D., Small-molecule targeted recruitment of a nuclease to cleave an oncogenic RNA in a mouse model of metastatic cancer. *Proc Natl Acad Sci USA* 2020, 117 (5), 2406-2411.

7. Disney, M. D.; Labuda, L. P.; Paul, D. J.; Poplawski, S. G.; Pushechnikov, A.; Tran, T.; Velagapudi, S. P.; Wu, M.; Childs-Disney, J. L., Two-dimensional combinatorial screening identifies specific aminoglycoside-RNA internal loop partners. *J Am Chem Soc* 2008, 130 (33), 11185-11194.

8. Parker, C. G.; Galmozzi, A.; Wang, Y.; Correia, B. E.; Sasaki, K.; Joslyn, C. M.; Kim, A. S.; Cavallaro, C. L.; Lawrence, R. M.; Johnson, S. R.; Narvaiza, I.; Saez, E.; Cravatt, B. F., Ligand and Target Discovery by Fragment-Based Screening in Human Cells. *Cell* 2017, 168 (3), 527-541 e29.

9. Hampf, M.; Gossen, M., A protocol for combined *Photinus* and *Renilla luciferase* quantification compatible with protein assays. *Anal Biochem* 2006, 356 (1), 94-99.

10. Team, R. C., R: A language and environment for statistical computing. 2013.

11. Velagapudi, S. P.: Gallo, S. M.; Disney, M. D., Sequence-based design of bioactive small molecules that target precursor microRNAs. *Nat Chem Biol* 2014, 10 (4), 291-297.

12. Yang, S.; Zhang, J. J.; Huang. X. Y., Mouse models for tumor metastasis. *Methods Mol Biol* 2012, 928, 221-228.

13. Gomez, L. G.; MacKenna, D. A.; Johnson, B. G.; Kaimal, V.; Roach, A. M.: Ren, S.; Nakagawa, N.; Xin, C.; Newitt, R.; Pandya, S.; Xia, T. H.; Liu, X.; Borza, D. B.; Grafals, M.; Shankland, S. J.; Himmelfarb, J.; Portilla. D.; Liu, S.; Chau. B. N.; Duffield, J. S., Anti-microRNA-21 oligonucleotides prevent Alport nephropathy progression by stimulating metabolic pathways. *J Clin Invest* 2015, 125 (1), 141-156.

REFERENCES FOR FIGURES

1. Pushpakom, S.; Iorio, F.; Eyers, P. A.: Escott, K. J.; Hopper, S.; Wells, A.; Doig, A.; Guilliams, T.; Latimer, J.; McNamee, C.; Norris, A.; Sanseau, P.; Cavalla, D.; Pirmohamed, M., Drug repurposing: progress, challenges and recommendations. *Nat Rev Drug Discov,* 2019, 18 (1), 41-58.

2. Janes, J.; Young, M. E.; Chen, E.; Rogers, N. H.; Burgstaller-Muehlbacher, S.; Hughes, L. D.; Love, M. S.; Hull, M. V.; Kuhen, K. L.; Woods, A. K.; Joseph, S. B.; Petrassi, H. M.: McNamara, C. W.; Tremblay. M. S.: Su, A. I.; Schultz, P. G.; Chatterjee, A. K., The ReFRAME library as a comprehensive drug repurposing library and its application to the treatment of cryptosporidiosis. *Proc Natl Acad Sci USA* 2018, 115 (42), 10750-10755.

3. Tran, T.; Disney, M. D., Identifying the preferred RNA motifs and chemotypes that interact by probing millions of combinations. *Nat Commun* 2012, 3, 1125.

4. Velagapudi, S. P.: Costales, M. G.; Vummidi, B. R.; Nakai, Y.; Angelbello, A. J.; Tran, T.; Haniff, H. S.; Matsumoto, Y.; Wang, Z. F.; Chatterjee, A. K.; Childs-Disney, J. L.; Disney, M. D., Approved anti-cancer drugs target oncogenic non-coding RNAs. *Cell Chem Bio* 2018, 25 (9), 1086-1094.e7.

5. Velagapudi, S. P.; Luo, Y.; Tran, T.; Haniff, H. S.: Nakai, Y.: Fallahi, M.; Martinez, G. J.; Childs-Disney, J. L.; Disney, M. D., Defining RNA-small molecule affinity landscapes enables design of a small molecule inhibitor of an oncogenic noncoding RNA. *ACS Cent Sci* 2017, 3 (3), 205-216.

6. Velagapudi, S. P.: Gallo, S. M.; Disney, M. D., Sequence-based design of bioactive small molecules that target precursor microRNAs. *Nat Chem Biol* 2014, 10 (4), 291-297.

7. Choi, Y J.; Kim, H. S.; Park, S. H.; Kim, B. S.; Kim, K. H.; Lee, H. J; Song, H. S.; Shin, D. Y.; Lee, H. Y.; Kim, H. G.; Lee, K. H.; Lee, J. L.; Park, K. H., Phase II Study of Dovitinib in Patients with Castration-Resistant Prostate Cancer (KCSG-GUi1-05). *Cancer Res Treat* 2018, 50 (4). 1252-1259.

8. Krichevsky, A. M.; Gabriely, G., miR-21: a small multi-faceted RNA. *J Cell Mol Med* 2009, 13 (1), 39-53.

9. Esquela-Kerscher, A.; Slack, F. J., Oncomirs—microRNAs with a role in cancer. *Nat Rev Cancer* 2006, 6 (4), 259-269.

10. Gomez., I. G.; MacKenna, D. A.; Johnson, B. G.; Kaimal, V.; Roach, A. M.; Ren, S.; Nakagawa, N.; Xin, C.; Newitt, R.; Pandya, S.: Xia, T. H.: Liu, X.; Borza, D. B.: Grafals, M.; Shankland, S. J.; Himmelfarb, J.; Portilla, D.: Liu, S.; Chau, B. N.; Duffield, J. S., Anti-microRNA-21 oligonucleotides prevent Alport nephropathy progression by stimulating metabolic pathways. *J Clin Invest* 2015, 125 (1), 141-156.

11. Bartel, D. P., MicroRNAs: genomics, biogenesis, mechanism, and function. *Cell* 2004, 116 (2), 281-297.

12. Bartel, D. P., MicroRNAs: target recognition and regulatory functions. *Cell* 2009, 136 (2), 215-233.

13. Renhowe, P. A.; Pecchi, S.; Shafer, C. M.; Machajewski, T. D.; Jazan, E. M.; Taylor, C.: Antonios-McCrea, W.; McBride, C. M.; Frazier, K.; Wiesmann, M.; Lapointe, G. R.; Feucht, P. H.; Warne, R. L.; Heise, C. C.; Menezes, D.; Aardalen, K.; Ye, H.: He, M.; Le, V.; Vora, J.; Jansen, J. M.; Wernette-Hammond, M. E.: Harris, A. L., Design, structure-activity relationships and in vivo characterization of 4-amino-3-benzimidazol-2-ylhydroquinolin-2-ones: a novel class of receptor tyrosine kinase inhibitors. *J Med Chem* 2009, 52 (2), 278-292.

14. Velagapudi, S. P.: Li, Y.; Disney, M. D., A cross-linking approach to map small molecule-RNA binding sites in cells. *Bioorg Med Them Lett* 2019, 29 (12), 1532-1536.

15. Trudel, S.: Li, Z. H.; Wei, E.; Wiesmann, M.; Chang, H.; Chen, C.; Reece, D.; Heise, C.: Stewart, A. K., CHIR-258, a novel, multitargeted tyrosine kinase inhibitor for the potential treatment of t(4; 14) multiple myeloma. *Blood* 2005, 105 (7), 2941-2948.

16. Costales, M. G.; Matsumoto, Y.; Velagapudi, S. P.; Disney, M. D., Small molecule targeted recruitment of a nuclease to RNA. *J Am Chem Soc* 2018, 140 (22), 6741-6744.

17. Sakamoto, K. M.; Kim, K. B.; Kumagai. A.; Mercurio, F.; Crews, C. M.; Deshaies, R. J., Protacs: chimeric molecules that target proteins to the Skp1-Cullin-F box complex for ubiquitination and degradation. *Proc Natl Acad Sci USA* 2001, 98 (15), 8554-8559.

18. Costales, M. G.; Aikawa, H.: Li, Y.; Childs-Disney, J. L.; Abegg, D.; Hoch, D. G.; Pradeep Velagapudi, S.; Nakai, Y.; Khan, T.; Wang, K. W.; Yildirim, I.; Adibekian, A.; Wang, E. T.; Disney, M. D., Small-molecule targeted recruitment of a nuclease to cleave an oncogenic RNA in a mouse model of metastatic cancer. *Proc Natl Acad Sci USA* 2020, 117 (5), 2406-2411.

19. Crews, C. M., Feeding the machine: mechanisms of proteasome-catalyzed degradation of ubiquitinated proteins. *Curr Opin Chem Biol* 2003, 7 (5), 534-539.

20. Costales, M. G.: Suresh, B.; Vishnu, K.; Disney, M. D., Targeted degradation of a hypoxia-associated non-coding RNA enhances the selectivity of a small molecule interacting with RNA. *Cell Chem Bio* 2019, 26 (8), 1180-1186.e5.

21. Yang, S.; Zhang, J. J.; Huang, X. Y., Mouse models for tumor metastasis. *Methods Mol Biol* 2012, 928, 221-228.

22. Hudson, B. G.; Tryggvason, K.; Sundaramoorthy, M.; Neilson, E. G., Alport's syndrome, Goodpasture's syndrome, and type IV collagen. *N Engl J Med* 2003, 348 (25), 2543-2556.

23. Cosgrove, D.; Meehan, D. T.; Grunkemeyer, J. A.; Kornak, J. M.; Sayers, R.: Hunter, W. J.; Samuelson, G. C., Collagen COL4A3 knockout: a mouse model for autosomal Alport syndrome. *Genes Dev* 1996, 10 (23), 2981-2992.

SUMMARY STATEMENTS

The inventions, examples, biological assays and results described and claimed herein have may attributes and embodiments include, but hot limited to, those set forth or described or referenced in this application.

All patents, publications, scientific articles, web sites and other documents and material references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such paten, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporated into the written description or any other portion of the application any and all such claims. Thus, for example, tinder no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred nonlimiting embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising" "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, for example, the term "X and/or Y" " means "X" or "Y" or both "X" and "Y" and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and the right is reserved to revise the application or claims to refer specifically to any individual member or any subgroup of members of the Markush group.

What is claimed is:

1. A method for targeting an RNA entity comprising contacting the RNA entity with a binding composition wherein the RNA entity is (1) pre-miR-21, (2) an oncogenic cell line containing pre-miR-21, the cell line being a TNBC breast cancer cell line, MDA-MD-231 breast cancer cell line, prostate cancer cell line, or non-small-cell lung carcinoma cell line, (3) an animal host having an oncogenic cell line associated with pre-miR-21, (4) a human having an oncogenic malignancy associated with pre-miR-21, (5) an animal host having Alport Syndrome kidney disease, (6) a human having Alport Syndrome kidney disease or any disease in which pre-miR-21 is causative or contributive; and, the binding composition comprises at least a Ribotac-Dovitinib having a formula of Compound 2 or a Protac-Dovitinib having a formula of Compound 3

Compound 2

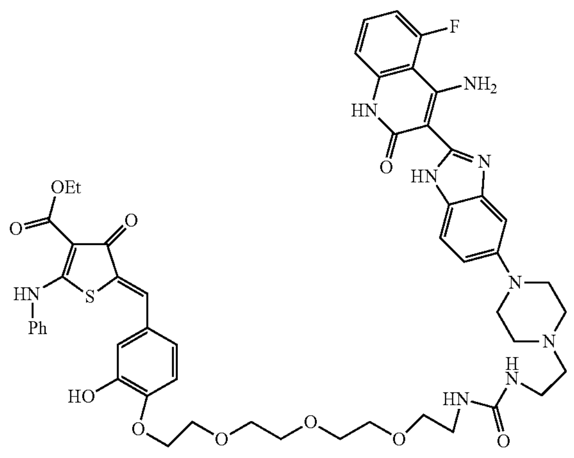

-continued

Compound 3

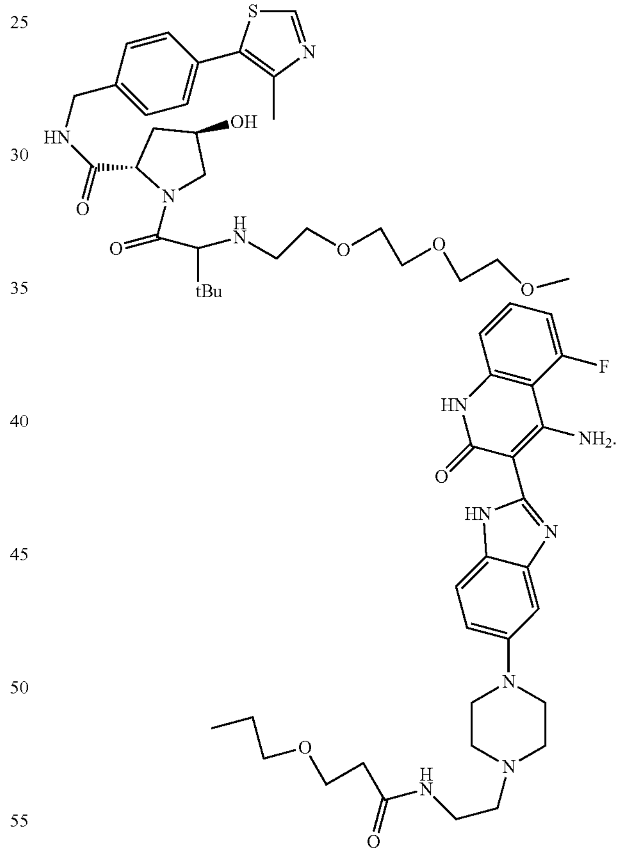

2. The method according to claim 1 wherein the contacting comprises contacting a TNBC breast cancer cell line, MDA-MD-231 breast cancer cell line, or anon-small-cell lung carcinoma cell line with the binding composition.

3. The method according to claim 1 wherein the RNA entity is an animal host having Alport Syndrome kidney disease, wherein the animal host having Alport Syndrome kidney disease is an Alport Syndrome mouse model; or the RNA entity is a human having Alport Syndrome kidney disease.

4. The method according to claim 1 wherein the contacting comprises contacting a TNBC breast cell cancer line with a binding composition comprising Compound 2 or Compound 3.

5. The method according to claim 1 wherein the contacting comprises contacting an MDA-MB-231 breast cancer cell line with a binding composition comprising Compound 2 or Compound 3.

6. The method according to claim 1 wherein the contacting comprising contacting a prostate cancer cell line with a binding composition comprising Compound 2 or Compound 3.

7. The method according to claim 1 wherein the RNA entity is a breast cancer cell line or prostate cancer cell line present in an animal or human host.

8. A composition comprising Compound 2 or Compound 3 or any combination thereof wherein

9. The composition of claim 8 comprising Compound 2.

10. The composition of claim 8 comprising Compound 3.

11. A pharmaceutical composition comprising a composition of claim 8 and a pharmaceutically acceptable carrier.

12. A method for treatment of breast cancer cells, prostate cancer cells, non-small cell lung cancer cells or Alport Syndrome kidney cells comprising contacting the cells with a pharmaceutical composition of claim 11.

13. The method according to claim 12 wherein the cancer cells are present in an animal host.

14. The method according to claim 12 wherein the cancer cells are human cells and are present in a laboratory animal or human.

15. The method according to claim 14 wherein the cancer cells are human cells and are present in a human.

16. A method for determining a binding site on a pre-miRNA for Dovitinib comprising contacting the pre-miRNA Compound 2 is

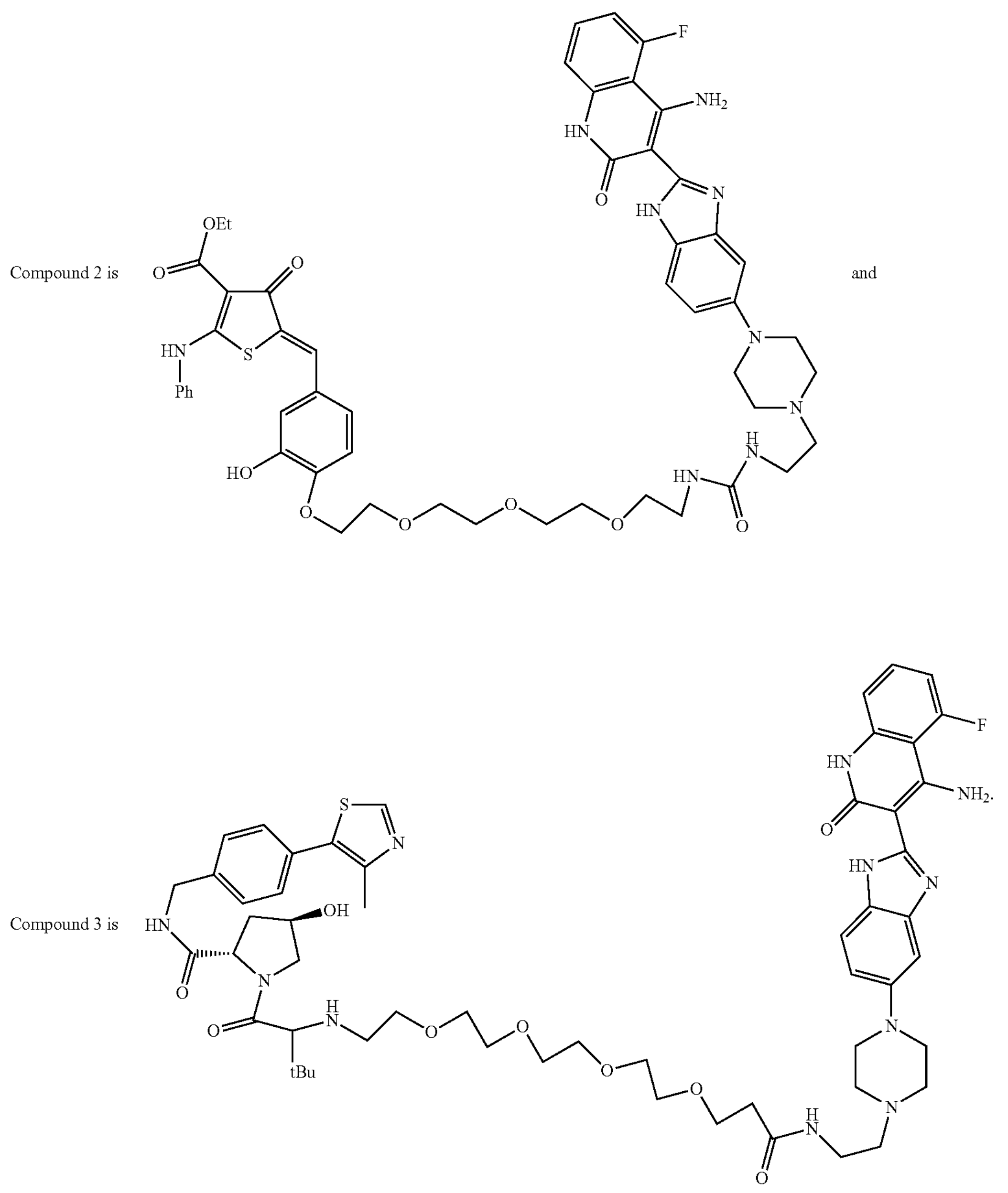 [SMILES: CCOC(=O)C1=C(Nc2ccccc2)S/C(=C\c2ccc(OCCOCCOCCOCCNC(=O)NCCN3CCN(c4ccc5[nH]c(-c6c(N)c7c(F)cccc7[nH]c6=O)nc5c4)CC3)c(O)c2)C1=O ; Cc1ncsc1-c1ccc(CNC(=O)[C@@H]2C[C@@H](O)CN2C(=O)C(NCCOCCOCCOCCOCCC(=O)NCCN2CCN(c3ccc4[nH]c(-c5c(N)c6c(F)cccc6[nH]c5=O)nc4c3)CC2)C(C)(C)C)cc1]

and

Compound 3 is with Compound 4 to form a complex, irradiating the complex, contacting the complex with a biotin azide to form a biotin-triazolyl-complex, and isolating the biotin-triazolyl complex with a streptavidin substance, wherein Compound 4 has the formula:

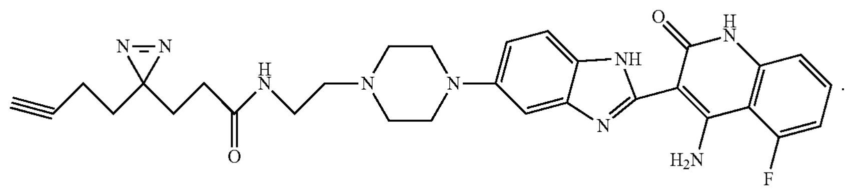 [SMILES: C#CCCC1(CCC(=O)NCCN2CCN(c3ccc4[nH]c(-c5c(N)c6c(F)cccc6[nH]c5=O)nc4c3)CC2)N=N1]

17. The method of claim 1, wherein the RNA entity is a human having a disease in which pre-miR-21 is causative or contributive.

18. The method of claim 17, wherein the disease is breast cancer, prostate cancer, or non-small cell lung cancer disease.

19. The method of claim 12, wherein the pharmaceutical composition comprises Compound 2.

20. The method of claim 12, wherein the pharmaceutical composition comprises Compound 3.

21. The method of claim 1, wherein the binding composition comprises Compound 2.

22. The method of claim 1, wherein the binding composition comprises Compound 3.

* * * * *

SEQUENCE LISTING

```
<160> NUMBER OF SEQ ID NOS: 22

<210> SEQ ID NO 1
<211> LENGTH: 23
<212> TYPE: DNA
<213> ORGANISM: Artificial sequence
<220> FEATURE:
<223> OTHER INFORMATION: Synthetic sequence

<400> SEQUENCE: 1
```

-continued acacgcaaat tcgtgaagcg ttc 23

<210> SEQ ID NO 2
<211> LENGTH: 20
<212> TYPE: DNA
<213> ORGANISM: Artificial sequence
<220> FEATURE:
<223> OTHER INFORMATION: Synthetic sequence

<400> SEQUENCE: 2
gaatcgagca ccagttacgc 20

<210> SEQ ID NO 3
<211> LENGTH: 22
<212> TYPE: DNA
<213> ORGANISM: Artificial sequence
<220> FEATURE:
<223> OTHER INFORMATION: Synthetic sequence

<400> SEQUENCE: 3
tagcttatca gactgatgtt ga 22

<210> SEQ ID NO 4
<211> LENGTH: 58
<212> TYPE: DNA
<213> ORGANISM: Artificial sequence
<220> FEATURE:
<223> OTHER INFORMATION: Synthetic sequence

<400> SEQUENCE: 4
tagcttatca gactgatgtt gactgttgaa tctcatggca acaccagtcg atgggctg 58

<210> SEQ ID NO 5
<211> LENGTH: 33
<212> TYPE: DNA
<213> ORGANISM: Artificial sequence
<220> FEATURE:
<223> OTHER INFORMATION: Synthetic sequence

<400> SEQUENCE: 5
taatacgact cactatagta gcttatcaga ctg 33

<210> SEQ ID NO 6
<211> LENGTH: 15
<212> TYPE: DNA
<213> ORGANISM: Artificial sequence
<220> FEATURE:
<223> OTHER INFORMATION: Synthetic sequence

<400> SEQUENCE: 6
cagcccatcg actgg 15

<210> SEQ ID NO 7
<211> LENGTH: 21
<212> TYPE: DNA
<213> ORGANISM: Artificial sequence
<220> FEATURE:
<223> OTHER INFORMATION: Synthetic sequence

<400> SEQUENCE: 7
gacacctctg cataacgcag t 21

<210> SEQ ID NO 8
<211> LENGTH: 22
<212> TYPE: DNA

```
<213> ORGANISM: Artificial sequence
<220> FEATURE:
<223> OTHER INFORMATION: Synthetic sequence

<400> SEQUENCE: 8

agggctttga ccttaccata ca                                              22


<210> SEQ ID NO 9
<211> LENGTH: 20
<212> TYPE: DNA
<213> ORGANISM: Artificial sequence
<220> FEATURE:
<223> OTHER INFORMATION: Synthetic sequence

<400> SEQUENCE: 9

gtaacccgtt gaaccccatt                                                 20


<210> SEQ ID NO 10
<211> LENGTH: 20
<212> TYPE: DNA
<213> ORGANISM: Artificial sequence
<220> FEATURE:
<223> OTHER INFORMATION: Synthetic sequence

<400> SEQUENCE: 10

ccatccaatc ggtagtagcg                                                 20


<210> SEQ ID NO 11
<211> LENGTH: 20
<212> TYPE: DNA
<213> ORGANISM: Artificial sequence
<220> FEATURE:
<223> OTHER INFORMATION: Synthetic sequence

<400> SEQUENCE: 11

gttcgacagt cagccgcatc                                                 20


<210> SEQ ID NO 12
<211> LENGTH: 19
<212> TYPE: DNA
<213> ORGANISM: Artificial sequence
<220> FEATURE:
<223> OTHER INFORMATION: Synthetic sequence

<400> SEQUENCE: 12

ggaatttgcc atgggtgga                                                  19


<210> SEQ ID NO 13
<211> LENGTH: 59
<212> TYPE: RNA
<213> ORGANISM: Homo sapiens

<400> SEQUENCE: 13

uagcuuauca gacugauguu gacuguugaa ucucauggca acaccagucg augggcugu      59


<210> SEQ ID NO 14
<211> LENGTH: 60
<212> TYPE: RNA
<213> ORGANISM: Artificial Sequence
<220> FEATURE:
<223> OTHER INFORMATION: Synthetic sequence

<400> SEQUENCE: 14

uagcuuauca gacugauguu gacuguugaa ucucaugguc aacaccaguc gaugggcugu     60
```

<210> SEQ ID NO 15
<211> LENGTH: 59
<212> TYPE: RNA
<213> ORGANISM: Homo sapiens

<400> SEQUENCE: 15
uagcuuauca gacugauguu gacuguugaa ucucauggca acaccagucg augggcugu 59

<210> SEQ ID NO 16
<211> LENGTH: 20
<212> TYPE: DNA
<213> ORGANISM: Artificial sequence
<220> FEATURE:
<223> OTHER INFORMATION: Synthetic sequence

<400> SEQUENCE: 16
caacatcagt ctgataagct 20

<210> SEQ ID NO 17
<211> LENGTH: 22
<212> TYPE: DNA
<213> ORGANISM: Artificial sequence
<220> FEATURE:
<223> OTHER INFORMATION: Synthetic sequence

<400> SEQUENCE: 17
attcaacagt caacatcagt ct 22

<210> SEQ ID NO 18
<211> LENGTH: 45
<212> TYPE: RNA
<213> ORGANISM: Artificial sequence
<220> FEATURE:
<223> OTHER INFORMATION: Synthetic sequence
<220> FEATURE:
<221> NAME/KEY: misc_difference
<222> LOCATION: (16)..(18)
<223> OTHER INFORMATION: n is a, c, g, or u
<220> FEATURE:
<221> NAME/KEY: misc_difference
<222> LOCATION: (29)..(30)
<223> OTHER INFORMATION: n is a, c, g, or u

<400> SEQUENCE: 18
gggagagggu uuaaunnnua cgaaaguann auuggauccg caagg 45

<210> SEQ ID NO 19
<211> LENGTH: 22
<212> TYPE: RNA
<213> ORGANISM: Artificial sequence
<220> FEATURE:
<223> OTHER INFORMATION: Synthetic sequence

<400> SEQUENCE: 19
uagcuuauca gacugauguu ga 22

<210> SEQ ID NO 20
<211> LENGTH: 23
<212> TYPE: RNA
<213> ORGANISM: Artificial sequence
<220> FEATURE:
<223> OTHER INFORMATION: Synthetic sequence

<400> SEQUENCE: 20
uaguacucug guuguuaagc uag 23

<210> SEQ ID NO 21

-continued

```
<211> LENGTH: 45
<212> TYPE: RNA
<213> ORGANISM: Artificial sequence
<220> FEATURE:
<223> OTHER INFORMATION: Synthetic sequence

<400> SEQUENCE: 21

gggagagggu uuaaugacua cgaaaguagc auuggauccg caagg                45


<210> SEQ ID NO 22
<211> LENGTH: 46
<212> TYPE: RNA
<213> ORGANISM: Artificial sequence
<220> FEATURE:
<223> OTHER INFORMATION: Synthetic sequence

<400> SEQUENCE: 22

gggagagggu uuaaugacua cgaaaguagu cauuggaucc gcaagg               46
```